(12) United States Patent
O'Toole et al.

(10) Patent No.: US 7,667,020 B2
(45) Date of Patent: Feb. 23, 2010

(54) COMPOSITION AND METHOD FOR TREATING LUPUS NEPHRITIS

(75) Inventors: Margot O'Toole, Newton, MA (US); William Martin Mounts, Andover, MA (US); Negin Shojaee, San Jose, CA (US)

(73) Assignee: Wyeth, Madison, NJ (US)

( * ) Notice: Subject to any disclaimer, the term of this patent is extended or adjusted under 35 U.S.C. 154(b) by 225 days.

(21) Appl. No.: 11/787,715

(22) Filed: Apr. 17, 2007

(65) Prior Publication Data
US 2008/0009008 A1    Jan. 10, 2008

Related U.S. Application Data

(62) Division of application No. 10/718,834, filed on Nov. 21, 2003, now abandoned.

(60) Provisional application No. 60/428,065, filed on Nov. 21, 2002.

(51) Int. Cl.
*C07H 21/00* (2006.01)
*C12Q 1/68* (2006.01)
*C12P 21/06* (2006.01)

(52) U.S. Cl. .................. 536/23.5; 435/6; 435/69.1

(58) Field of Classification Search .................. None
See application file for complete search history.

(56) References Cited

FOREIGN PATENT DOCUMENTS

WO    WO 02/059260    8/2002

OTHER PUBLICATIONS

PCT International Search Report; PCT/US03/37317; mailed Jan. 6, 2005, 6 pages.

Balow et al., *New Prospects For Treatment of Lupus Nephritis*, Seminars in Nephrology, vol. 20, No. 1, pp. 32-39, 2000.
Davis et al., *Lupus Nephritis*, Current Opinion in Rheumatology, vol. 8, No. 5, pp. 415-423, 1996.
Mercadal et al., *Lupus Nephritis, A Review of the Current Pharmacological Treatments*, Expert Opinion Pharmacother., vol. 5, No. 11, pp. 2263-2277, 2004.
Rahman et al., *A Novel Susceptibility Locus On Chromosone 2 in the (New Zealand Black x New Zealand White) $F_1$ Hybrid Mouse Model of Systematic Lupus Erythematosus*, The Journal of Immunology, vol. 168, No. 6, pp. 3042-3049, 2002.
BP Tsao, *Genetic Susceptibility of Lupus Nephritis*, Lupus, vol. 7, No. 9, pp. 585-590, 1998.
Database Geneseq Online Feb. 25, 2003, "Human protein SEQ ID 521," XP002350892, retrieved from EBI accession No. GSN: ABP64861 Database accesion No. ABP64861.
Database UniProt Online May 1, 2000, XP002350893 retrieved from EBI Database accession No. Q9VFS6.
Database UniProt Online Mar. 1, 2003, XP002350894 retrieved from EBI Database accession No. Q8CHT3.
European Search Report for Application No. 03786989.8 (PCT/US03/37317) dated Nov. 11, 2005, 5 pages.
Vilella-Bach et al., "The FKBP12-Rapamycin-binding Domain Is Required for FKBP12-Rapamycin-associated Protein Kinase Activity and G1 Progression," *Journal of Biological Chemistry*, 274(7):4266-4272 (1999).

*Primary Examiner*—Daniel C Gamett
(74) *Attorney, Agent, or Firm*—Maria Restrepo-Hartwig; Elizabeth A. Hurley

(57) ABSTRACT

The present invention provides novel isolated BFLP1698 polynucleotides and polypeptides encoded by the BFLP1698 polynucleotides. Also provided are the antibodies that immunospecifically bind to a BFLP1698 polypeptide or any derivative (including fusion derivative), variant, mutant or fragment of the BFLP1698 polypeptide, polynucleotide or antibody. The invention additionally provides methods in which the BFLP1698 polypeptide, polynucleotide and antibody are utilized in the detection and treatment of a broad range of pathological states, as well as to other uses.

9 Claims, 2 Drawing Sheets

Gene Expression Levels in (NZB x NZW)F1 Kidneys of Mouse Ortholog of Human Gene BFLP1698 and the Effect of Therapy on Gene Expression Levels

COMPOSITION AND METHOD FOR TREATING LUPUS NEPHRITIS

RELATED APPLICATIONS

This application is a divisional application of U.S. patent application Ser. No. 10/718,834, filed Nov. 21, 2003 now abandoned, which claims priority to U.S. provisional patent application 60/428,065 filed Nov. 21, 2002. The entire contents of these applications are incorporated herein by reference in their entireties.

FIELD OF THE INVENTION

The invention relates generally to nucleic acids and polypeptides and more specifically to nucleic acids and polypeptides encoding polypeptides useful for detecting and treating lupus nephritis, as well as for identifying therapeutic agents for treating the same.

BACKGROUND OF THE INVENTION

Lupus nephritis is an example of a "classical" auto-immune disease in which the patient's immune system attacks his/her own organs. It has been estimated that 45-75% of lupus patients eventually suffer from some form or other of kidney damage. Lupus varies greatly in severity from mild cases requiring minimal intervention to those in which significant damage occurs to vital organs such as lungs, kidneys, heart and brain, and which ultimately can be fatal. Lupus is predominantly a female disease, with an approximate female to male ratio being 9:1. In North America, it is estimated to affect 1 in 500 females mainly between the age of 20 to 40 years.

There is no known cure for lupus. Treatment is typically directed at controlling the symptoms with the hope of putting the disease into remission. Recently, the antibiotic rapamycin has been demonstrated to be an effective therapy in treating lupus nephritis in a murine model of the disease.

SUMMARY OF THE INVENTION

The invention is based, in part, upon the discovery of a gene, named BFLP1698, whose expression is increased in kidney tissue in mice with lupus nephritis; however, the expression level of the gene does not decrease markedly in response to treatment with rapamycin. This expression profile indicates that the product of the BFLP1698 gene interacts with rapamycin when this antibiotic is administered to ameliorate the symptoms of lupus nephritis. In the absence of rapamycin, the gene product is free to bring about the diseased state, and its effects can include the activation of genes required to bring about the diseased state. In the presence of rapamycin, the BFLP1698 gene product is inactive and the disease state diminishes. Accordingly, the BFLP1698 protein is useful as a target for identifying agents that, like rapamycin, are useful in treating symptoms of lupus nephritis.

In one aspect, the invention provides an isolated nucleic acid molecule that includes the sequence of a nucleotide sequence encoding a BFLP1698 gene product. In a preferred embodiment, the nucleotide sequence includes the sequence of SEQ ID NO:1, or a fragment, homolog, analog or derivative thereof. The nucleic acid can include, e.g., a nucleic acid sequence encoding a polypeptide at least 70%, e.g., 80%, 85%, 90%, 95%, 98%, or even 99% or more identical to a polypeptide that includes the amino acid sequences of SEQ ID NO:2. The nucleic acid can be, e.g., a genomic DNA fragment, or a cDNA molecule.

Also included in the invention is a vector containing one or more of the nucleic acids described herein, and a cell containing the vectors or nucleic acids described herein.

The invention is also directed to host cells transformed with a vector comprising any of the nucleic acid molecules described above.

In another aspect, the invention includes a pharmaceutical composition that includes a BFLP1698 nucleic acid and a pharmaceutically acceptable carrier or diluent.

In a further aspect, the invention includes a substantially purified BFLP1698 polypeptide, e.g., any of the BFLP1698 polypeptides encoded by a BFLP1698 nucleic acid, and fragments, homologs, analogs, and derivatives thereof. The invention also includes a pharmaceutical composition that includes a BFLP1698 polypeptide and a pharmaceutically acceptable carrier or diluent.

In a still further aspect, the invention provides an antibody that binds specifically to a BFLP1698 polypeptide. The antibody can be, e.g., a monoclonal or polyclonal antibody, and fragments, homologs, analogs, and derivatives thereof. The invention also includes a pharmaceutical composition including BFLP1698 antibody and a pharmaceutically acceptable carrier or diluent. The invention is also directed to isolated antibodies that bind to an epitope on a polypeptide encoded by any of the nucleic acid molecules described above.

The invention also includes kits comprising in one or more containers one or more of a compound that is a BFLP1698 nucleic acid, a BFLP1698 polypeptide and/or an antibody to a BFLP1698 polypeptide. The kit is preferably provided with instructions for use. If desired, the compounds in the kits are provided along with a pharmaceutically acceptable carrier.

The invention further provides a method for producing a BFLP1698 polypeptide by providing a cell containing a BFLP1698 nucleic acid, e.g., a vector that includes a BFLP1698 nucleic acid, and culturing the cell under conditions sufficient to express the BFLP1698 polypeptide encoded by the nucleic acid. The expressed BFLP1698 polypeptide is then recovered from the cell. Preferably, the cell produces little or no endogenous BFLP1698 polypeptide. The cell can be, e.g., a prokaryotic cell or eukaryotic cell.

The invention is also directed to methods of identifying a BFLP1698 polypeptide or nucleic acid in a sample by contacting the sample with a compound that specifically binds to the polypeptide or nucleic acid, and detecting complex formation, if present.

The invention further provides methods of identifying a compound that modulates the activity of a BFLP1698 polypeptide by contacting a BFLP1698 polypeptide with a compound and determining whether the BFLP1698 polypeptide activity is modified.

The invention is also directed to compounds that modulate BFLP1698 polypeptide activity identified by contacting a BFLP1698 polypeptide with the compound and determining whether the compound modifies activity of the BFLP1698 polypeptide, binds to the BFLP1698 polypeptide, or binds to a nucleic acid molecule encoding a BFLP1698 polypeptide.

In another aspect, the invention provides a method of determining the presence of or predisposition of a BFLP1698-associated disorder in a subject. The method includes providing a sample from the subject and measuring the amount of BFLP1698 polypeptide in the subject sample. The amount of BFLP1698 polypeptide in the subject sample is then compared to the amount of BFLP1698 polypeptide in a control sample. An alteration in the amount of BFLP1698 polypeptide in the subject protein sample relative to the amount of BFLP1698 polypeptide in the control protein sample indicates the subject has a tissue proliferation-associated condition. A control sample is preferably taken from a matched individual, i.e., an individual of similar age, sex, or other general condition but who is not suspected of having a tissue proliferation-associated condition. Alternatively, the control sample may be taken from the subject at a time when the subject is not suspected of having a tissue proliferation-associated disorder. In some embodiments, the BFLP1698 is detected using a BFLP1698 antibody.

In a further aspect, the invention provides a method of determining the presence of or predisposition of a BFLP1698-associated disorder in a subject. The method includes providing a nucleic acid sample, e.g., RNA or DNA, or both, from the subject and measuring the amount of the BFLP1698 nucleic acid in the subject nucleic acid sample. The amount of BFLP1698 nucleic acid sample in the subject nucleic acid sample is then compared to the amount of a BFLP1698 nucleic acid in a control sample. An alteration in the amount of BFLP1698 nucleic acid in the sample relative to the amount of BFLP1698 in the control sample indicates the subject has a tissue proliferation-associated disorder.

In a still further aspect, the invention provides a method of treating or preventing or delaying a BFLP1698-associated disorder. The method includes administering to a subject in which such treatment or prevention or delay is desired a BFLP1698 nucleic acid, a BFLP1698 polypeptide, or a BFLP1698 antibody in an amount sufficient to treat, prevent, or delay a tissue proliferation-associated disorder in the subject. Examples of such disorders include rheumatoid arthritis and multiple sclerosis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
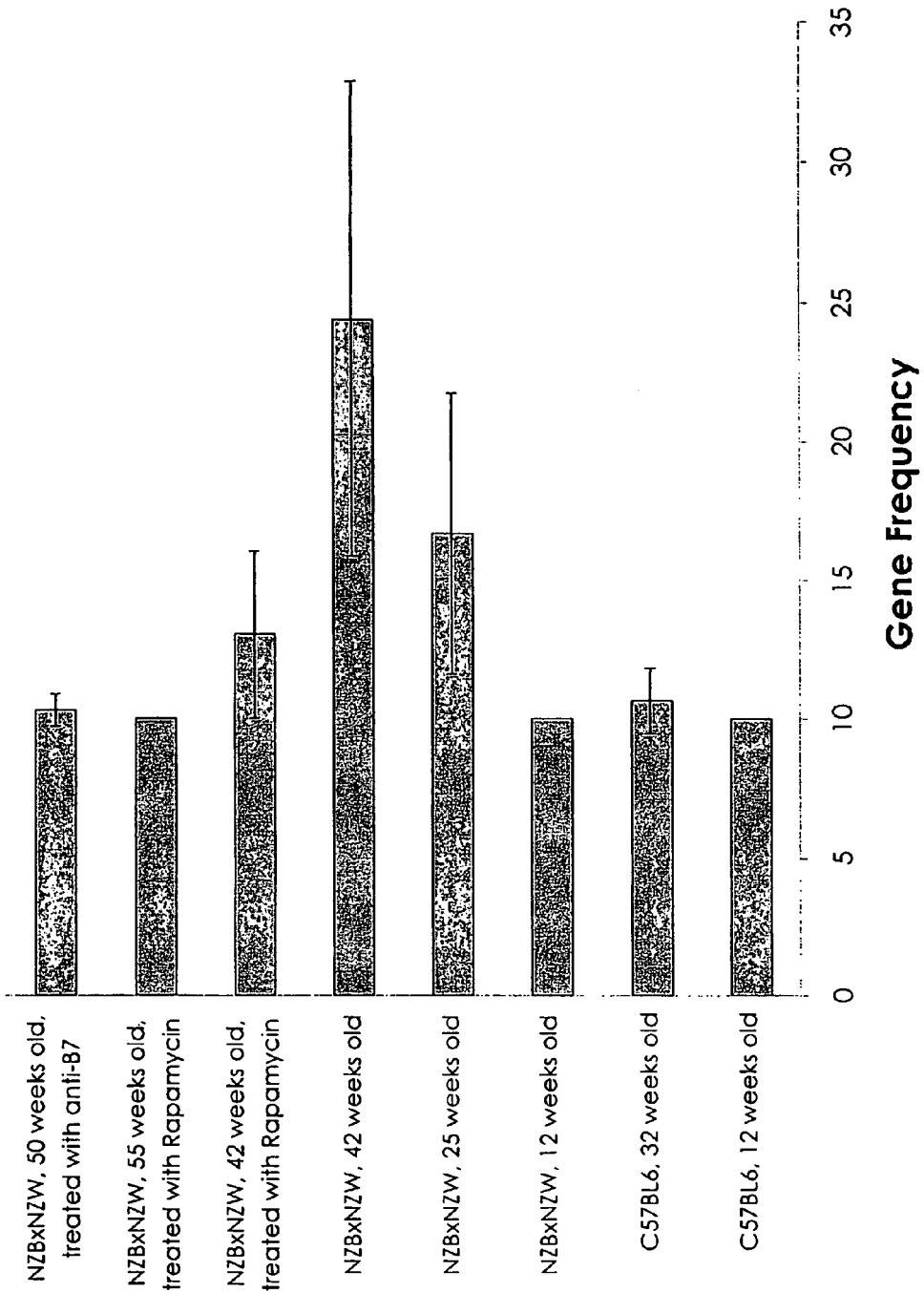
FIG. 1 is a histogram showing relative levels of gene expression in the mouse ortholog of the human BFLP1698 gene in NZB×NZWF1 kidneys before, during, and after rapamycin treatment, as well as in various control mouse strains and conditions.

The BFLP1698 nucleic acid sequences disclosed herein were identified based on changes in expression of the gene in kidneys of a lupus nephritis model mouse as compared to expression of the gene in kidneys from non-diseased mice. More particularly, the gene is expressed at relatively low levels in young mice and mice that do not show symptoms of lupus nephritis. Gene expression is elevated in mice with lupus nephritis, and is lower in mice that have been successfully treated with rapamycin or anti-B7 antibodies. The observation that expression levels return to normal when kidney function is normal indicates that elevated levels are related to, and diagnostic of, disease progression. Blocking the function of these genes may inhibit or retard disease progression. Expression levels can also to used to assess and compare effectiveness of various therapeutic interventions.

Accordingly, the BFLP1698 nucleic acid sequences are useful for detecting the presence of lupus nephritis in a subject. Elevated levels of BFLP01698 transcripts or polypeptides relative to levels in control samples indicate the presence of lupus nephritis in the subject. BFLP1698 nucleic acid sequences can also be used to monitor the effectiveness of treatments for lupus nephritis: a decrease in expression of BFLP1698 genes relative to levels in diseased treatments demonstrates that the treatment is effective.

The BFLP1698 sequences can additionally be used to identify therapeutic agents for treating or preventing lupus nephritis in a subject. For example, a BFLP1698 polypeptide can be contacted with a test agent. Binding of the BFLP1698 polypeptide to the test agent reveals that the test agent modulates BFLP1698 activity. The BFLP1698-binding agent can be further tested to determine if it acts to promote or inhibit lupus symptoms in a test organism (e.g., a NZB×NZW mouse). Inhibition of lupus symptoms reveals that the agent is useful for treating or preventing lupus nephritis, or symptoms associated with lupus nephritis. Additional utilities are disclosed herein.

A 3652 nucleotide sequence that includes a human BFLP1698 nucleic acid is shown in Table 1 (SEQ ID NO:1). The human sequence was identified as the human ortholog of a murine gene whose expression is increased in a NZB×NZW mouse with lupus nephritis-like symptoms.

Nucleotides 1-3486 of the sequence shown in Table 1 encode a polypeptide of 1162 amino acids, whose sequence is shown in Table 2 (SEQ ID NO:2).

TABLE 1

(SEQ ID NO: 1)
ATGGCCCTTGTGCCAGGGAGAAGCAAGGAGGATGGGCTTTGG
ACTAGAAATAGCCCAGGCTCCTCCCAGCATCCAGAAAGTCCCAGGCTGCC
CAACCCTCTCTGGGACAGAGGAAAAATTGGCAAGGTTGAAGGTCACCAGC
ACATTCAGGATTTCTCTCAAAAGTCCCATCTGCCGTCTATTGTGGTGGAA
TCCAGTGAGGTGAATGAAGAGAGTGGGGATCTCCATTTGCCCCATGAGGA
GCTGCTGCTGCTCACTGATGGTGAGGAAGAGGATGCTGAGGCCTTCTTCC
AAGACCAAAGTGAAGAGCCAGGGGCGGCACGTCCCCATCATCAGGCTCGG
CAAGTGGAGCATTCGACGCAGCGCGGCCATCTGGAGATTCGGGAGCTGAA
GAAGAAGCTGTTCAAACGCCGGCGGGTGTTGAATCGGGAGCGGCGTCTGA
GGCACCGGGTGGTCGGGGCTGTGATAGACCAAGGGCTGATCACGCGGCAC
CACCTCAAGAAGCGGGCTGCTCAGGAGCTGTCCCAGGAAATCAAGGCTTT
TCTGACTGGCGTAGACCCCATTCTGGGCCACCAACTCTCAGCCCGGGAAC
ATGCTCGCTGTGGTCTTCTCCTGCTCCGTTCTTTGCCACCTGCTCGGGCT
GCTGTGCTTGACCACTTGAGAGGTGTCTTTGATGAGAGTGTCCGGGCCCA
CCTGGCTGCCCTGGATGAAACCCCTGTGGCTGGTCCACCTCACCTCCGTC
CACCTCCACCCTCTCATGTCCCTGCTGGTGGACCTGGTCTAGAGGATGTG
GTTCAGGAAGTGCAGCAGGTGCTGTCTGAGTTTATCCGGGCCAACCCAAA
GGCCTGGGCACCTGTGATTAGTGCATGGTCCATTGACCTCATGGGGCAAC
TGAGCAGCACGTACTCAGGCCAGCACCAGCGTGTTCCCCACGCTACTGGC
GCTCTTAATGAACTGCTACAGCTGTGGATGGGTTGTAGGGCCACGCGTAC
ATTAATGGACATCTATGTGCAGTGCCTCTCGGCTCTCATTGGTAGCTGCC
CAGATGCGTGTGTGGATGCCTTGCTGGATACCTCTGTTCAGCATTCTCCA
CACTTTGACTGGGTTGTGGCACATATTGGCTCCTCTTTTCCTGGCACCAT
CATTTCCCGGGTTCTCTCCTGTGGCCTTAAGGACTTTTGTGTCCATGGTG
GGGCTGGAGGTGGAGCTGGCAGTAGTGGTGGAAGCTCTTCTCAGACCCCC
TCTACAGACCCCTTCCCTGGATCTCCTGCCATTCCTGCGGAGAAACGGGT
GCCCAAGATTGCCTCAGTTGTAGGCATCCTAGGTCACCTGGCCTCCCGCC
ACGGAGATAGCATCCGACGGGAGCTCCTGCGAATGTTCCATGATAGCCTG
GCAGGGGATCTGGAGGCCGCAGTGGGACCCCTCCCTTCAGGCCACGGT
TCCGTTCCTACTGCAGCTGGCAGTCATGTCACCAGCTTTGCTGGGCACTG
TCTCTGGAGAGCTTGTGGATTGCCTCAAGCCCCCAGCTGTGCTGAGCCAG
CTGCAGCAACACCTTCAAGGATTCCCCCGAGAGGAGCTGGACAACATGTT
GAACCTGGCTGTGCACCTGGTGAGCCAGGCCTCTGGGGCAGGTGCCTACC
GCTTGCTGCAGTTCCTGGTGGACACAGCTATGCCTGCTTCGGTCATTACC
ACCCAGGGCCTGGCTGTGCCAGACACCGTGCGTGAGGCTTGTGACCGGCT
AATCCAGCTGCTGCTGCTGCACCTGCAAAAACTGGTTCATCACCGGGGAG
GGTCTCCTGGGGAAGGGGTGCTAGGCCCGCCCCCACCTCCCCGCTTGGTG
CCCTTTTTAGATGCGCTCAAAAACCATGTTGGAGAGCTGTGTGGAGAGAC
GTTACGATTGGAACGGAAGCGCTTCCTCTGGCAGCACCAGCTCTTGGGCC

TGCTGTCTGTCTATACCCGGCCTAGCTGTGGACCTGAGGCCTTGGGCCAT
CTGCTGAGCCGAGCCCGAAGCCCTGAAGAGTTGAGTTTGGCCACCCAGTT
ATATGCAGGGCTAGTGGTCAGCCTCTCTGGCCTCCTGCCCCTGGCTTTCC
GAAGCTGTCTGGCTCGGGTGCATGCAGGGACATTACAGCCTCCCTTCACG
GCCCGGTTCCTGCGCAACTTGGCACTGCTAGTAGGGTGGGAACAGCAGGG
TGGCAGGGCCCTGCAGCCCTAGGGGCGCACTTTGGGGAATCTGCCTCAG
CCCATCTGTCTGACCTGGCTCCTCTCCTGCTACATCCTGAGGAGGAAGTA
GCTGAAGCTGCTGCCTCTCTCCTGGCCATTTGTCCCTTTCCTTCTGAAGC
CTTATCCCCCTCCCAGCTCCTGGGACTGGTAAGGGCTGGGGTGCACCGCT
TCTTTGCCTCTCTGAGGCTGCATGGACCCCCAGGTGTGGCCTCAGCCTGT
CAGCTTCTCACCCGCCTGTCTCAGACATCCCCAGCTGGGCTCAAGGCTGT
CCTGCAGCTGCTGGTTGAAGGAGCCTTACATCGAGGCAACACAGAACTGT
TTGGTGGGCAAGTAGATGGGGACAATGAGACTCTCTCAGTTGTTTCAGCT
TCTTTGGCTTCTGCCTCCCTGTTGGACACTAACCGGAGGCACACTGCAGC
TGTGCCAGGTCCTGGAGGGATTTGGTCAGTTTTCCATGCTGGAGTCATCG
GCCGTGGCTTAAAGCCACCCAAGTTTGTCCAGTCACGAAATCAGCAGGAA
GTGATCTATAACACCCAGAGCCTCCTCAGCCTCCTGGTTCACTGCTGCAG
TGCCCCAGGGGGCACTGAATGTGGGGAATGCTGGGGGGCACCCATCTTGA
GTCCAGAGGCAGCCAAAGCAGTGGCAGTGACCTTGGTGGAGAGTGTGTGT
CCCGATGCAGCTGGTGCAGAGCTGGCCTGGCCCCCCGAGGAACACGCCCG
GGCCACCGTGGAGCGGGATCTCCGCATTGGCCGGCGCTTCCGCGAACAGC
CCCTGCTCTTTGAGCTGTTAAAGCTGGTAGCAGCTGCACCCCCAGCCCTG
TGCTACTGTTCCGTGCTGCTTCGGGGCTGCTGGCCGCCCTCTTGGGCCA
TTGGGAAGCCTCTCGCCACCCTGACACGACCCACTCCCCCTGGCACCTGG
AGGCATCCTGCACCTTAGTGGCTGTCATGGCTGAGGGAAGCCTCCTGCCT
CCGGCCCTGGGTAATATGCATGAAGTATTTAGCCAACTGGCACCTTTCGA
GGTGCGTCTGCTGCTGCTCAGTGTCTGGGGTTTTCTCCGGGAGCATGGGC
CCTTGCCTCAGAAGTTCATCTTCCAATCAGAGCGGGGTCGCTTCATTCGG
GACTTCTCCAGGGAGGGTGGAGGTGAGGGTGGACCCCATCTGGCTGTGCT
GCACAGTGTCCTCCACCGCAACATCGACCGCCTAGGTCTTTTCTCTGGCC
GTTTCCAGGCACCTTCACCGTCCACTCTCCTTCGACAGGGGACGTAGCCT
TTTCTTGCTCTGGAAGCCCAGGGAGGTTGAGCAGTGAGAGAGGGAAGGGA
CTAACGTGCTCCGGAAGGGTGGAGGTTTCTCTTCTAAGTCCTTGGTCTAA
AGAGCGCTGTCACTTTTTTCTCTCCCACTTTTTTTTTTCTAAATAAATT
TGCCAACTTG

TABLE 2

(SEQ ID NO: 2)
MALVPGRSKEDGLWTRNSPGSSQHPESPRLPNPLWDRGKIGK

VEGHQHIQDFSQKSHLPSIVVESSEVNEESGDLHLPHEELLLLTDGEEED

AEAFFQDQSEEPGAARPHHQARQVEHSTQRGHLEIRELKKKLFKRRRVLN

RERRLRHRVVGAVIDQGLITRHHLKKRAAQELSQEIKAFLTGVDPILGHQ

LSAREHARCGLLLLRSLPPARAAVLDHLRGVFDESVRAHLAALDETPVAG

PPHLRPPPPSHVPAGGPGLEDVVQEVQQVLSEFIRANPKAWAPVISAWSI

DLMGQLSSTYSGQHQRVPHATGALNELLQLWMGCRATRTLMDIYVQCLSA

LIGSCPDACVDALLDTSVQHSPHFDWVVAHIGSSFPGTIISRVLSCGLKD

FCVHGGAGGGAGSSGGSSSQTPSTDPFPGSPAIPAEKRVPKIASVVGILG

HLASRHGDSIRRELLRMFHDSLAGGSGGRSGDPSLQATVPFLLQLAVMSP

ALLGTVSGELVDCLKPPAVLSQLQQHLQGFPREELDNMLNLAVHLVSQAS

GAGAYRLLQFLVDTAMPASVITTQGLAVPDTVREACDRLIQLLLLHLQKL

VHHRGGSPGEGVLGPPPPPRLVPFLDALKNHVGELCGETLRLERKRFLWQ

HQLLGLLSVYTRPSCGPEALGHLLSRARSPEELSLATQLYAGLVVSLSGL

LPLAFRSCLARVHAGTLQPPFTARFLRNLALLVGWEQQGGEGPAALGAHF

GESASAHLSDLAPLLLHPEEEVAEAAASLLAICPFPSEALSPSQLLGLVR

TABLE 2-continued

AGVHRFFASLRLHGPPGVASACQLLTRLSQTSPAGLKAVLQLLVEGALHR

GNTELFGGQVDGDNETLSVVSASLASASLLDTNRRHTAAVPGPGGIWSVF

HAGVIGRGLKPPKFVQSRNQQEVIYNTQSLLSLLVHCCSAPGGTECGECW

GAPILSPEAAKAVAVTLVESVCPDAAGAELAWPPEEHARATVERDLRIGR

RFREQPLLFELLKLVAAAPPALCYCSVLLRGLLAALLGHWEASRHPDTTH

SPWHLEASCTLVAVMAEGSLLPPALGNMHEVFSQLAPFEVRLLLLSVWGF

LREHGPLPQKFIFQSERGRFIRDFSREGGGEGGPHLAVLHSVLHRNIDRL

GLFSGRFQAPSPSTLLRQGT

BFLP1698-like nucleic acids and polypeptides of the invention (including those shown in Table 1) are referred to herein as "BFLP1698" nucleic acids and polypeptides.

A BFLP1698 nucleic acid, and the encoded polypeptide, according to the invention are useful in a variety of applications and contexts.

BFLP1698 shows homology to other proteins as shown in the BLAST results described in Table 3. KIAA0169, IMAGE: 3461492, and 3598686, and cDNA: FLJ21639 are all proteins encoded from partial reading frames (expressed sequence tags (ESTs)) found in genomic DNA. Because BFLP1698 has homology to these proteins, it is also encoded from either an entire open reading frame, or part of a larger open reading frame (EST).

TABLE 3

BLAST RESULTS FOR KIAA1698

| Gene Index/Identifier | Protein/Organism | Length (aa) | Identity (%) | Positives (%) | Expect |
|---|---|---|---|---|---|
| gi\|20480454\|ref\|XP_167747.1\| (XM_167747) | similar to KIAA1698 protein [Homo sapiens] | 1019 | 823/993 (82%) | 824/993 (82%) | 0.0 |
| gi\|12697941\|dbj\|BAB21789.1\| (AB051485) | KIAA1698 protein [Homo sapiens] | 908 | 770/902 (85%) | 770/902 (85%) | 0.0 |
| gi\|20380408\|gb\|AAH28025.1\| (BC028025) | Similar to KIAA1698 protein [Homo sapiens] | 833 | 705/829 (85%) | 705/829 (85%) | 0.0 |
| gi\|20849521\|ref\|XP_144111.1\| (XM_144111) | similar to KIAA1698 protein [Homo sapiens] [Mus musculus] | 963 | 169/229 (73%) | 175/229 (75%) | 3e-87 |
| gi\|21296297\|gb\|EAA08442.1\| (AAAB01008879) | agCP2919 [Anopheles gambiae str. PEST] | 900 | 80/292 (27%) | 121/292 (41%) | 1e-16 |

Table 4 shows a ClustalW alignment of BFLP1698 (SEQ ID NO:2) against the proteins described above in Table 3.

TABLE 4

CLUSTALW ANALYSIS OF SEQ ID NO: 2

```
1) SEQ ID NO: 2
2) gi| 20480454|ref|XP_167747.1| (XM_167747)   (SEQ ID NO: 16)
3) gi| 12697941|dbj|BAB21789.1| (AB051485)     (SEQ ID NO: 17)
4) gi| 20380408|gb|AAH28025.1| (BC028025)      (SEQ ID NO: 18)
5) gi| 20849521|ref|XP_144111.1| (XM_144111)   (SEQ ID NO: 19)
6) gi| 21296297|gb|EAA08442.1| (AAAB01008879)  (SEQ ID NO: 20)
                        10        20        30        40        50        60
                ....|....|....|....|....|....|....|....|....|....|....|....|
SEQ ID NO: 2    MALVPGRSKEDGLWTRNSPGSSQHPESPRLPNPLWDRGKIGKVEGHQHIQDFSQKSHLPS  60
gi|20480454|ref  ------------------------------------------------------------   1
gi|12697941|dbj  ------------------------------------------------------------   1
gi|20380408|gb|  ------------------------------------------------------------   1
gi|20849521|ref  ---------MILMITLFTTATFLVLGVSVWVLIKEILTVHVPPPIPQRVKFHMLHYFFQ  50
gi|21296297|gb|  ------------------------------------------------------------   1
```

TABLE 4-continued

CLUSTALW ANALYSIS OF SEQ ID NO: 2

```
                     70        80        90       100       110       120
                ....|....|....|....|....|....|....|....|....|....|....|....|
SEQ ID NO: 2    IVVESSEVNEESGDLHLPHEELLLLTDGEEEDAEAFFQDQSEEPGAARPHHQARQVEHST 120
gi|20480454|ref -------------------------------------MSALCDPPGAPGPPGPAPATHG--  22
gi|12697941|dbj ------------------------------------------------------------   1
gi|20380408|gb| ------------------------------------------------------------   1
gi|20849521|ref LTIALGNVLEKMKICPMPRFFCFIQDLLVSKNNFGVLVKNMHFGTIPVRLFQPKATSSGP 110
gi|21296297|gb| ------------------------------------------------------------   1

130       140       150       160       170       180
                ....|....|....|....|....|....|....|....|....|....|....|....|
SEQ ID NO: 2    QRGHLEIRELKKKLFKRRRVLNRERRLRHRVVGAVIDQGLITRHHLKKRAAQELSQEIKA 180
gi|20480454|ref ----------------------PAP--LS---------------------AQELSQEIKA  37
gi|12697941|dbj ------------------------------------------------------------   1
gi|20380408|gb| ------------------------------------------------------------   1
gi|20849521|ref RKGIIFYHGGGGVFGSLDSYHNTCSYLAHET-----------------DSVVMAVGYRK 152
gi|21296297|gb| ------------------------------------------------------------   1

190       200       210       220       230       240
                ....|....|....|....|....|....|....|....|....|....|....|....|
SEQ ID NO: 2    FLTGVDPILGHQLSAREHARCGLLLLRSLPPARAAVLDHLRGVFDESVRAHLAALDETPV 240
gi|20480454|ref FLTGVDPILGHQLSAREHARCGLLLLRSLPPARAAVLDHLRGVFDESVRAHLAALDETPV  97
gi|12697941|dbj ------------------------------------------------------------   1
gi|20380408|gb| ------------------------------------------------------------   1
gi|20849521|ref LPDHHHPTAYHDCLNATVHFLKELKTYGVDPARVVVSGESIGAGAAAIIAQVVLARKDLP 212
gi|21296297|gb| ------------------------------------------------------------   1

250       260       270       280       290       300
                ....|....|....|....|....|....|....|....|....|....|....|....|
SEQ ID NO: 2    AGPPHLRPPPPSHVPAGGPGLKKVQEVQKKLSEFIRANPKAWAPVISAWSIDLKG---- 296
gi|20480454|ref AGPPHLRPPPPSHVPAGGPGLKKVQEVQKKLSEFIRANPKAWAPVISAWSIDLKG---- 153
gi|12697941|dbj ---------------PAGGPGLKKVQEVQKKLSEFIRANPKAWAPVISAWSIDLKG----  42
gi|20380408|gb| ------------------------------------------------------------   1
gi|20849521|ref QFRAQVLINPVVQGVNFQLPSYQQYSKAVPFKSRKKMTCACKKLAKDQKWKDAMKGTFI 272
gi|21296297|gb| ------------KNLPDPSVDKAVQEKHKALERLVTVGPTAWCPVLSKWCEKIEG----  44

310       320       330       340       350       360
                ....|....|....|....|....|....|....|....|....|....|....|....|
SEQ ID NO: 2    --KSSTMGGQHQR--VPHATGALNELLQLWDGGRATKTLKDIYVQCLSALIGSCPDACV 352
gi|20480454|ref --KSSTMGGQHQR--VPHATGALNELLQLWDGGRATKTLKDIYVQCLSALIGSCPDACV 209
gi|12697941|dbj --KSSTMGGQHQR--VPHATGALNELLQLWDGGRATKTLKDIYVQCLSALIGSCPDACV  98
gi|20380408|gb| ---------------------------------PRVRDIYVQCLSALIGSCPDACV  23
gi|20849521|ref PPDHWKKMAKWLSSDNKKQRFKKGRQPKFPGPFNEKAYLETNKKFSLETSPLLADDKIK 332
gi|21296297|gb| --KKCKKKCRKRPP-----DIRG---ACNLWKGGSAIRYIKSKSALCFEKLDQREMDECK  94

370       380       390       400       410       420
                ....|....|....|....|....|....|....|....|....|....|....|....|
SEQ ID NO: 2    DALLDT---SVQHSPHFDWVVAHIGSSFPGTIISRVLSCGLKDFCVHGGAGGGAGSSGGS 409
gi|20480454|ref DALLDT---SVQHSPHFDWVVAHIGSSFPGTIISRVLSCGLKDFCVHGGAGGGAGSSGGS 266
gi|12697941|dbj DALLDT---SVQHSPHFDWVVAHIGSSFPGTIISRVLSCGLKDFCVHGGAGGGAGSSGGS 155
gi|20380408|gb| DALLDT---SVQHSPHFDWVVAHIGSSFPGTIISRVLSCGLKDFCVHGGAGGGAGSSGGS  80
gi|20849521|ref AQLPKTFLVSSKDVLRDDTKLKKKRLEEQGKPVTWLWVGLPDVRMVP-LSQGPRKPGPP 391
gi|21296297|gb| NEMLVIYG---THKEFKDWVVARKGGCFKLRKKSSMLKKGKARLTGDFDQPSEKEVELS 151

430       440       450       460       470       480
                ....|....|....|....|....|....|....|....|....|....|....|....|
SEQ ID NO: 2    SSQTPSTDPFPGSPAIPAEKRVPKIASVVGILGH-LASRHGDSIRRELLRMFHDSLAGGS 468
gi|20480454|ref SSQTPSTDPFPGSPAIPAEKRVPKIASVVGILGH-LASRHGDSIRRELLRMFHDSLAGGS 325
gi|12697941|dbj SSQTPSTDPFPGSPAIPAEKRVPKIASVVGILGH-LASRHGDSIRRELLRMFHDSLAGGS 214
gi|20380408|gb| SSQTPSTDPFPGSPAIPAEKRVPKIASVVGILGH-LASRHGDSIRRELLRMFHDSLAGGS 139
gi|20849521|ref GPAPAKHGPVPLSAQELKKIKAPFTGMDPILGHQLSAREHAQCGLLLRSLPPKQAAVL 451
gi|21296297|gb| YLGLAHESDLRKKLKSTLEHVASYKQPKPYKL---KLKKASKKTSQAKKAKELKLHD- 205

490       500       510       520       530       540
                ....|....|....|....|....|....|....|....|....|....|....|....|
SEQ ID NO: 2    GGRSG--DPSLQATVPFLLQLAVMSPALLGTVSGELVDCLKP--PAVLSQLQQHLQGFPR 524
gi|20480454|ref GGRSG--DPSLQATVPFLLQLAVMSPALLGTVSGELVDCLKP--PAVLSQLQQHLQGFPR 381
gi|12697941|dbj GGRSG--DPSLQATVPFLLQLAVMSPALLGTVSGELVDCLKP--PAVLSQLQQHLQGFPR 270
gi|20380408|gb| GGRSG--DPSLQATVPFLLQLAVMSPALLGTVSGELVDCLKP--PAVLSQLQQHLQGFPR 195
gi|20849521|ref DHLRGVFDESKKQAHKAALEKSPVAGPHLRPPSPSHVPTGGPGLEDVKHKKQVLCEFIR 511
gi|21296297|gb| EN-----RLPTLTVKPKNWPANKGLPYKLHTVSGLLKMKKKHAIRVTLILAKMSTQHSWC 260

550       560       570       580       590       600
                ....|....|....|....|....|....|....|....|....|....|....|....|
SEQ ID NO: 2    E----------------ELDNMLNLAVHLVSQASGAG-------------------- 545
gi|20480454|ref E----------------ELDNMLNLAVHLVSQASGAG-------------------- 402
gi|12697941|dbj E----------------ELDNMLNLAVHLVSQASGAG-------------------- 291
gi|20380408|gb| E----------------ELDNMLNLAVHLVSQASGAG-------------------- 216
gi|20849521|ref ANPKVWAPVISAWSIDLMGQLSKTYKGQHQRVPHAKGKRNELLQLWMSCRDTRTLMDIYV 571
gi|21296297|gb| K----------------ELLEMMFKEKETKVLDKHTA-------------------- 281
```

TABLE 4-continued

CLUSTALW ANALYSIS OF SEQ ID NO: 2

```
                        610        620        630        640        650        660
                   ....|....|....|....|....|....|....|....|....|....|....|....|
SEQ ID NO: 2       ------------AYRLL--------------------------------------------  550
gi|20480454|ref    ------------AYRLL--------------------------------------------  407
gi|12697941|dbj    ------------AYRLL--------------------------------------------  296
gi|20380408|gb|    ------------AYRLL--------------------------------------------  221
gi|20849521|ref    QCLSALIGSCPDAYSFPGFPAIPGEKRVPKIASAVGIQVTWLSAMETASDGNCCACFMIV  631
gi|21296297|gb|    -------------ALL---------------------------------------------  284

670        680        690        700        710        720
                   ....|....|....|....|....|....|....|....|....|....|....|....|
SEQ ID NO: 2       --QFLVDTAMPASVITTQGLAVPDTVREACDRLIQLLLLHLQKLVHHRGGSPGEGVLGPP  608
gi|20480454|ref    --QFLVDTAMPASVITTQGLAVPDTVREACDRLIQLLLLHLQKLVHHRGGSPGEGVLGPP  465
gi|12697941|dbj    --QFLVDTAMPASVITTQGLAVPDTVREACDRLIQLLLLHLQKLVHHRGGSPGEGVLGPP  354
gi|20380408|gb|    --QFLVDTAMPASVITTQGLAVPDTVREACDRLIQLLLLHLQKLVHHRGGSPGEGVLGPP  279
gi|20849521|ref    WQQFLVDTAMPAAVITTQGLAVPDTVREAYDRLIQLLLLHLQKLVHHRGGSPGEGVLGPP  691
gi|21296297|gb|    --SDSSRDGVREMSWNSCTSDVEYLQSVEVR--SILLASFKSNSVFHSTIVYLLSVSEEA  340

730        740        750        760        770        780
                   ....|....|....|....|....|....|....|....|....|....|....|....|
SEQ ID NO: 2       PPPRLVPFLDALKNHVGELCGETLRLERKRFLWQHQLLGLLSVYTRPSCG--PEALGHLL  666
gi|20480454|ref    PPPRLVPFLDALKNHVGELCGETLRLERKRFLWQHQLLGLLSVYTRPSCG--PEALGHLL  523
gi|12697941|dbj    PPPRLVPFLDALKNHVGELCGETLRLERKRFLWQHGLLGLLSVYTRPSCG--PEALGHLL  412
gi|20380408|gb|    PPPRLVPFLDALKNHVGELCGETLRLERKRFLWQHQLLGLLSVYTRPSCG--PEALGHLL  337
gi|20849521|ref    SPELPVPFLDALKNHVGELCGSTLRLERKRFLWQHQLLAYS-------------------  732
gi|21296297|gb|    LAVSTKPHLSALVRVSGGPHGTVDVPSVKPAFETAFEKIDSSPCKRVEQWNILHNLVELL  400

790        800        810        820        830        840
                   ....|....|....|....|....|....|....|....|....|....|....|....|
SEQ ID NO: 2       SRARSPEELSLATQI-YAGLVVSLSGLLPLAFRSCLARVHAGTLQPPFTARFLRNLALLV  725
gi|20480454|ref    SRARSPEELSLATQI-YAGLVVSLSGLLPLAFRSCLARVHAGTLQPPFTARFLRNLALLV  582
gi|12697941|dbj    SRARSPEELSLATQI-YAGLVVSLSGLLPLAFRSCLARVHAGTLQPPFTARFLRNLALLV  471
gi|20380408|gb|    SRARSPEELSLATQI-YAGLVVSLSGLLPLAFRSCLARVHAGTLQPPFTARFLRNLALLV  396
gi|20849521|ref    -----------------------------------------------WELSKLALLV  742
gi|21296297|gb|    KLERSTAILGSTLRKSNCTGSMHELSLDRSLKINENPSSSRERQDDTQG--GGCTSRATQESQ  458

850        860        870        880        890        900
                   ....|....|....|....|....|....|....|....|....|....|....|....|
SEQ ID NO: 2       GWEQQGGEGPAALGAHFGESASAHLSDLAPLLLHPEEVAEAAASLLAICPFPSEALSPS  785
gi|20480454|ref    GWEQQGGEGPAALGAHFGESASAHLSDLAPLLLHPEEVAEAAASLLAICPFPSEALSPS  642
gi|12697941|dbj    GWEQQGGEGPAALGAHFGESASAHLSDLAPLLLHPEEVAEAAASLLAICPFPSEALSPS  531
gi|20380408|gb|    GWEQQGGEGPAALGAHFGESASAHLSDLAPLLLHPEEVAEAAASLLAICPFPSEALSPS  456
gi|20849521|ref    GWEQQGDEGPSALGARFGESASAHLSDLAPLLLHPEEVAEAAASLLAVCPFPSEALSPS  802
gi|21296297|gb|    ENANSPGSRVKNERPEPMESDEQHRLGTGSRTVTYSSLIHETVRLSECSDLGKSVTSGTS  518

910        920        930        940        950        960
                   ....|....|....|....|....|....|....|....|....|....|....|....|
SEQ ID NO: 2       QLLGLVRAGVHRFFASLRLHGPPGVASACQLLTRLSQTS---------PAGLKAVLQLLV  836
gi|20480454|ref    QLLGLVRAGVHRFFASLRLHGPPGVASACQLLTRLSQTS---------PAGLKAVLQLLV  693
gi|12697941|dbj    QLLGLVRAGVHRFFASLRLHGPPGVASACQLLTRLSQTS---------PAGLKAVLQLLV  582
gi|20380408|gb|    QLLGLVRAGVHRFFASLRLHGPPGVASACQLLTRLSQTS---------PAGLKAVLQLLV  507
gi|20849521|ref    QLLGLVRAGVHHFFNSLRLHGPPGVASASQLLTRLSQTS---------PAGLKAVLQLLV  853
gi|21296297|gb|    QTLKLSSLLMKYFHYQLSLSTAGTSVPSGTSPESLDSSLNRVYSLLSKHCGHRKAASTAA  578

970        980        990       1000       1010       1020
                   ....|....|....|....|....|....|....|....|....|....|....|....|
SEQ ID NO: 2       EGALHRGNTELFGGQVDGDNETLSVVSASLASASLLDTNRRHTAAVPGPGGIWSVFHAGV  896
gi|20480454|ref    EGALHRGNTELFGGQVDGDNETLSVVSASLASASLLDTNRRHTAAVPGPGGIWSVFHAGV  753
gi|12697941|dbj    EGALHRGNTELFGGQVDGDNETLSVVSASLASASLLDTNRRHTAAVPGPGGIWSVFHAGV  642
gi|20380408|gb|    EGALHRGNTELFGGQVDGDNETLSVVSASLASASLLDTNRRHTAAVPGPGGIWSVFHAGV  567
gi|20849521|ref    EVALHRGNTELFGESNVGDNETLSSVSTPLASASLLDINRRHTAAVPGPGGIWSVFHAGV  913
gi|21296297|gb|    LRETLEGALFLSG-DEFGSQAESQAYSFDKPDDLISRLNSSQGIASNASR--ASVLHAGS  635

1030       1040       1050       1060       1070       1080
                   ....|....|....|....|....|....|....|....|....|....|....|....|
SEQ ID NO: 2       IGRGLKPPKFVQSRNQQEVIYNTQSLLSLLVHCCSAPGGTECGECWGAPILSPEAAKAVA  956
gi|20480454|ref    IGRGLKPPKFVQSRNQQEVIYNTQSLLSLLVHCCSAPGGTECGECWGAPILSPEAAKAVA  813
gi|12697941|dbj    IGRGLKPPKFVQSRNQQEVIYNTQSLLSLLVHCCSAPGGTECGECWGAPILSPEAAKAVA  702
gi|20380408|gb|    IGRGLKPPKFVQSRNQQEVIYNTQSLLSLLVHCCSAPGGTECGECWGAPILSPEAAKAVA  627
gi|20849521|ref    IGRGLKSPKIVQSRNHQEVIYNTQSLSSLLVHCCSASGSSEHKGYWGAFT----------  963
gi|21296297|gb|    IGSCPKIESKKAVGPASEQN--H-LLSASSVACCQDVNDHSATIDG---------FSYVS  683

1090       1100       1110       1120       1130       1140
                   ....|....|....|....|....|....|....|....|....|....|....|....|
SEQ ID NO: 2       VTLVESVCPDAAGAELAWPPEEHARATVERDLRIGRRFREQPLLFELLKLVAAAPPALCY 1016
gi|20480454|ref    VTLVESVCPDAAGAELAWPPEEHARATVERDLRIGRRFREQPLLFELLKLVAAAPPALCY  873
gi|12697941|dbj    VTLVESVCPDAAGAELAWPPEEHARATVERDLRIGRRFREQPLLFELLKLVAAAPPALCY  762
gi|20380408|gb|    VTLVESVCPDAAGAELAWPPEEHARATVERDLRIGRRFREQPLLFELLKLVAAAPPALCY  687
gi|20849521|ref    ------------------------------------------------------------  963
gi|21296297|gb|    SSLVEMSSPDVMYNGLPWBEESFIRVTSERDLSITQFTFHHSPSLSSSLGLVSCYRESLCY  743
```

TABLE 4-continued

CLUSTALW ANALYSIS OF SEQ ID NO: 2

```
                          1150       1160       1170       1180       1190       1200
                     ....|....|....|....|....|....|....|....|....|....|....|....|
SEQ ID NO: 2         CSVLLRGLLAALLGHWEASRHPDTT-HSPWHLEASCTLVAVMAEGSLLPPALGNMHEVFS 1075
gi|20480454|ref      CSVLLRGLLAALLGHWEASRHPDTT-HSPWHLEASCTLVAVMAEGSLLPPALGNMHEVFS  932
gi|12697941|dbj      CSVLLRGLLAALLGHWEASRHPDTT-HSPWHLEASCTLVAVMAEGSLLPPALGNMHEVFS  821
gi|20380408|gb|      CSVLLRGLLAALLGHWEASRHPDTT-HSPWHLEASCTLVAVMAEGSLLPPALGNMHEVFS  746
gi|20849521|ref      ------------------------------------------------------------  963
gi|21296297|gb|      CSVLLRALCASALHQWRSKTAETLNGQKTDLLYMSTKLSESMLLAQLLPPPLSYSHIVLE  803

1210       1220       1230       1240       1250       1260
                     ....|....|....|....|....|....|....|....|....|....|....|....|
SEQ ID NO: 2         QLAPFEVR-LLLLSVWGFLREHGPLPQKFIFQSERGRFIRDFS-REGGGEGGPHLAVLHS 1133
gi|20480454|ref      QLAPFEVR-LLLLSVWGFLREHGPLPQKFIFQSERGRFIRDFS-REGGGEGGPHLAVLHS  990
gi|12697941|dbj      QLAPFEVR-LLLLSVWGFLREHGPLPQKFIFQSERGRFIRDFS-REGGGEGGPHLAVLHS  879
gi|20380408|gb|      QLAPFEVR-LLLLSVWGFLREHGPLPQKFIFQSERGRFIRDFS-REGGGEGGPHLAVLHS  804
gi|20849521|ref      ------------------------------------------------------------  963
gi|21296297|gb|      YFDGPESAYSLKECVWNSSSSEVESPVLSCDPTGFHSRDPLSSRPPLQYTNPLRNTSQK  863

1270       1280       1290
                     ....|....|....|....|....|....|..
SEQ ID NO: 2         VLHRN--IDRLGLFSGRFQAPSPSTLLRQGT------ 1162
gi|20480454|ref      VLHRN--IDRLGLFSGRFQAPSPSTLLRQGT------ 1019
gi|12697941|dbj      VLHRN--IDRLGLFSGRFQAPSPSTLLRQGT------  908
gi|20380408|gb|      VLHRN--IDRLGLFSGRFQAPSPSTLLRQGT------  833
gi|20849521|ref      -------------------------------------  963
gi|21296297|gb|      KITSVGHSYHQMFVGPELSNPSASNSGSPTQQPLVQG  900
```

Residues 1-170 of SEQ ID NO:2 are referred to herein as SEQ ID NO:15. The fragment of SEQ ID NO:16 that includes amino acids 1-27 is referred to herein as SEQ ID NO:21.

BFLP1698 Nucleic Acids

The nucleic acids of the invention include those that encode a BFLP1698 polypeptide or protein. As used herein, the terms polypeptide and protein are interchangeable.

In some embodiments, a BFLP1698 nucleic acid encodes a mature BFLP1698 polypeptide. As used herein, a "mature" form of a polypeptide or protein described herein relates to the product of a naturally occurring polypeptide or precursor form or proprotein. The naturally occurring polypeptide, precursor or proprotein includes, by way of nonlimiting example, the full length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps that may take place within the cell in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

The invention includes mutant or variant nucleic acids of SEQ ID NO:1, or a fragment thereof, any of whose bases may be changed from the corresponding bases shown in SEQ ID NO:1, while still encoding a protein that maintains at least one of its BFLP1698-like activities and physiological functions (i.e., modulating angiogenesis, neuronal development). The invention further includes the complement of the nucleic acid sequence of SEQ ID NO:1, including fragments, derivatives, analogs and homologs thereof. The invention additionally includes nucleic acids or nucleic acid fragments, or complements thereto, whose structures include chemical modifications.

One aspect of the invention pertains to isolated nucleic acid molecules that encode BFLP1698 proteins or biologically active portions thereof. Also included are nucleic acid fragments sufficient for use as hybridization probes to identify BFLP1698-encoding nucleic acids (e.g., BFLP1698 mRNA) and fragments for use as polymerase chain reaction (PCR) primers for the amplification or mutation of BFLP1698 nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated BFLP1698 nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of SEQ ID NO:1, or a complement thereof, can be isolated using standard molecular biology techniques and the sequence information provided herein. Using all or a portion of the nucleic acid sequence of SEQ ID NO:1 as a hybridization probe, BFLP1698 nucleic acid sequences can be isolated using standard hybridization and cloning techniques (e.g., as described in Sambrook et al., eds., MOLECULAR CLONING: A LABORATORY MANUAL 2$^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to BFLP1698 nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO:1, or a complement thereof. Oligonucleotides may be chemically synthesized and may be used as probes.

In another embodiment, an isolated nucleic acid molecule of the invention comprises a nucleic acid molecule that is a complement of the nucleotide sequence shown in SEQ ID NO:1, or a portion of this nucleotide sequence. A nucleic acid molecule that is complementary to the nucleotide sequence shown in SEQ ID NO:1 is one that is sufficiently complementary to the nucleotide sequence shown in SEQ ID NO:1 that it can hydrogen bond with little or no mismatches to the nucleotide sequence shown in SEQ ID NO:1, thereby forming a stable duplex.

As used herein, the term "complementary" refers to Watson-Crick or Hoogsteen base pairing between nucleotide units of a nucleic acid molecule, and the term "binding" means the physical or chemical interaction between two polypeptides or compounds or associated polypeptides or compounds or combinations thereof. Binding includes ionic, non-ionic, Van der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NO:1, e.g., a fragment that can be used as a probe or primer, or a fragment encoding a biologically active portion of BFLP1698. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Fragments can include as many as 4, 5, 6, 7, 8, 9, 10, 11, 12, 13, 14, 15, 16, 17, 18, 19, or 20 amino acids. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98%, or even 99% identity (with a preferred identity of 80-99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of a BFLP1698 polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a BFLP1698 polypeptide of species other than humans, including, but not limited to, mammals, and thus can include, e.g., mouse, rat, rabbit, dog, cat, cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding human BFLP1698 protein. Homologous nucleic acid sequences include those nucleic acid sequences that encode conservative amino acid substitutions (see below) in SEQ ID NO:2, as well as a polypeptide having BFLP1698 activity. Biological activities of the BFLP1698 proteins are described below. A homologous amino acid sequence does not encode the amino acid sequence of a human BFLP1698 polypeptide.

The nucleotide sequence determined from the cloning of the human BFLP1698 gene allows for the generation of probes and primers designed for use in identifying and/or cloning BFLP1698 homologues in other cell types, e.g., from other tissues, as well as BFLP1698 homologues from other mammals. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 or more consecutive sense strand nucleotide sequence of SEQ ID NO:1; or an anti-sense strand nucleotide sequence of SEQ ID NO:1; or of a naturally occurring mutant of SEQ ID NO:1.

Probes based on the human BFLP1698 nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a BFLP1698 protein, such as by measuring a level of a BFLP1698-encoding nucleic acid in a sample of cells from a subject e.g., detecting BFLP1698 mRNA levels or determining whether a genomic BFLP1698 gene has been mutated or deleted.

A "polypeptide having a biologically active portion of BFLP1698" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of BFLP1698" can be prepared by isolating a portion of SEQ ID NO:1 that encodes a polypeptide having a BFLP1698 biological activity (biological activities of the BFLP1698 proteins are described below), expressing the encoded portion of BFLP1698 protein (e.g., by recombinant expression in vitro) and assessing the activity of the encoded portion of BFLP1698.

The invention also provides polymorphic forms of BFLP1698 nucleic acid sequences as well as methods of detecting polymorphic sequences in BFLP1698 sequences The polymorphic forms include genomic sequences corresponding to exons and/or introns associated with BFLP1698.

Individuals carrying polymorphic alleles of the invention may be detected at either the DNA, the RNA, or the protein level using a variety of techniques that are well known in the art. The present methods usually employ pre-characterized polymorphisms. That is, the genotyping location and nature of polymorphic forms present at a site have already been determined. The availability of this information allows sets of probes to be designed for specific identification of the known polymorphic forms.

The genomic DNA used for the diagnosis may be obtained from any nucleated cells of the body, such as those present in peripheral blood, urine, saliva, buccal samples, surgical specimen, and autopsy specimens. The DNA may be used directly or may be amplified enzymatically in vitro through use of PCR or other in vitro amplification methods such as the ligase chain reaction (LCR), strand displacement amplification (SDA), self-sustained sequence replication (3SR), prior to mutation analysis.

The detection of polymorphisms in specific DNA sequences, can be accomplished by a variety of methods including, but not limited to, restriction-fragment-length-polymorphism detection based on allele-specific restriction-endonuclease cleavage, hybridization with allele-specific oligonucleotide probes, including immobilized oligonucleotides or oligonucleotide arrays, allele-specific PCR, mismatch-repair detection (MRD), binding of MutS protein, denaturing-gradient gel electrophoresis (DGGE), single-strand-conformation-polymorphism detection, RNAase cleavage at mismatched base-pairs, chemical or enzymatic cleavage of heteroduplex DNA, methods based on allele specific primer_extension, genetic bit analysis (GBA), the oligonucleotide-ligation assay (OLA), the allele-specific ligation chain reaction (LCR), gap-LCR, radioactive and/or fluorescent DNA sequencing using standard procedures well known in the art, and peptide nucleic acid (PNA) assays.

BFLP1698 Variants

The invention further encompasses nucleic acid molecules that differ from the nucleotide sequences shown in SEQ ID NO:1 due to the degeneracy of the genetic code. These nucleic acids thus encode the same BFLP1698 protein as that encoded by the nucleotide sequence shown in SEQ ID NO:1, e.g., the polypeptide of SEQ ID NO:2. In another embodiment, an isolated nucleic acid molecule of the invention has a nucleotide sequence encoding a protein having an amino acid sequence shown in SEQ ID NO:2.

In addition to the human BFLP1698 nucleotide sequence shown in SEQ ID NO:1, it will be appreciated by those skilled in the art that DNA sequence polymorphisms that lead to changes in the amino acid sequences of BFLP1698 may exist within a population (e.g., the human population). Such genetic polymorphism in the BFLP1698 gene may exist among individuals within a population due to natural allelic variation. As used herein, the terms "gene" and "recombinant gene" refer to nucleic acid molecules comprising an open reading frame encoding a BFLP1698 protein, preferably a mammalian BFLP1698 protein. Such natural allelic variations can typically result in 1-5% variance in the nucleotide sequence of the BFLP1698 gene. Any and all such nucleotide variations and resulting amino acid polymorphisms in BFLP1698 that are the result of natural allelic variation and that do not alter the functional activity of BFLP1698 are intended to be within the scope of the invention.

Moreover, nucleic acid molecules encoding BFLP1698 proteins from other species, and thus that have a nucleotide sequence that differs from the human sequence of SEQ ID NO:1 are intended to be within the scope of the invention. Nucleic acid molecules corresponding to natural allelic variants and homologues of the BFLP1698 cDNAs of the invention can be isolated based on their homology to the human BFLP1698 nucleic acids disclosed herein using the human cDNAs, or a portion thereof, as a hybridization probe according to standard hybridization techniques under stringent hybridization conditions. For example, a soluble human BFLP1698 cDNA can be isolated based on its homology to human membrane-bound BFLP1698. Likewise, a membrane-bound human BFLP1698 cDNA can be isolated based on its homology to soluble human BFLP1698.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:1. In another embodiment, the nucleic acid is at least 10, 25, 50, 100, 250, 500 or 750 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding BFLP1698 proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

Thus, the present invention also includes polynucleotides capable of hybridizing under reduced stringency conditions, more preferably stringent conditions, and most preferably highly stringent conditions, to polynucleotides described herein. Examples of stringency conditions are shown in table 4A below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 4A

STRINGENCY CONDITIONS

| Stringency Condition | Polynucleotide Hybrid | Hybrid Length (bp)[1] | Hybridization Temperature and Buffer[H] | Wash Temperature and Buffer[H] |
|---|---|---|---|---|
| A | DNA:DNA | ≥50 | 65° C.; 1xSSC -or- 42° C.; 1xSSC, 50% formamide | 65° C.; 0.3xSSC |
| B | DNA:DNA | <50 | $T_B$*; 1xSSC | $T_B$*; 1xSSC 67° C.; 0.3xSSC |
| C | DNA:RNA | ≥50 | 67° C.; 1xSSC -or- 45° C.; 1xSSC, 50% formamide | |
| D | DNA:RNA | <50 | $T_D$*; 1xSSC | $T_D$*; 1xSSC 70° C.; 0.3xSSC |
| E | RNA:RNA | ≥50 | 70° C.; 1xSSC -or- 50° C.; 1xSSC, 50% formamide | |
| F | RNA:RNA | <50 | $T_F$*; 1xSSC | $T_F$*; 1xSSC 65° C.; 1xSSC |
| G | DNA:DNA | ≥50 | 65° C.; 4xSSC -or- 42° C.; 4xSSC, 50% formamide | |
| H | DNA:DNA | <50 | $T_H$*; 4xSSC | $T_H$*; 4xSSC 67° C.; 1xSSC |
| I | DNA:RNA | ≥50 | 67° C.; 4xSSC -or- 45° C.; 4xSSC, 50% formamide | |
| J | DNA:RNA | <50 | $T_J$*; 4xSSC | $T_J$*; 4xSSC 67° C.; 1xSSC |
| K | RNA:RNA | ≥50 | 70° C.; 4xSSC -or- 50° C.; 4xSSC, 50% formamide | |
| L | RNA:RNA | <50 | $T_L$*; 2xSSC | $T_L$*; 2xSSC 50° C.; 2xSSC |
| M | DNA:DNA | >50 | 50° C.; 4xSSC -or- 40° C.; 6xSSC, 50% formamide | |
| N | DNA:DNA | <50 | $T_N$*; 6xSSC | $T_N$*; 6xSSC 55° C.; 2xSSC |
| O | DNA:RNA | >50 | 55° C.; 4xSSC -or- 42° C.; 6xSSC, 50% formamide | |
| P | DNA:RNA | <50 | $T_P$*; 6xSSC | $T_P$*; 6xSSC 60° C.; 2xSSC |
| Q | RNA:RNA | >50 | 60° C.; 4xSSC -or- 45° C.; 6xSSC, 50% formamide | |
| R | RNA:RNA | <50 | $T_R$*; 4xSSC | $T_R$*; 4xSSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[H]SSPE (1xSSPE is 0.15M NaCl, 10 mM NaH$_2$PO$_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.
$T_B$*-$T_R$*The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + Tbases) + 4(# of G + C bases). For hybrids between 18 and 49 base pairs in length, $T_m$(° C.) = 81.5 + 16.6($\log_{10}$Na$^+$) + 0.41(% G + C) − (600/N), where N is the number of bases in the hybrid, and Na$^+$ is the concentration of sodium ions in the hybridization buffer (Na$^+$ for 1xSSC = 0.165 M).

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NO:1 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO:1, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C.

In a third embodiment, a nucleic acid that is hybridizable to the nucleic acid molecule comprising the nucleotide sequence of SEQ ID NO:1, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C.

Conservative Mutations

In addition to naturally-occurring allelic variants of the BFLP1698 sequence that may exist in the population, the skilled artisan will further appreciate that changes can be introduced by mutation into the nucleotide sequence of SEQ ID NO:1, thereby leading to changes in the amino acid sequence of the encoded BFLP1698 protein, without altering the functional ability of the BFLP1698 protein. For example, nucleotide substitutions leading to amino acid substitutions at "non-essential" amino acid residues can be made in the sequence of SEQ ID NO:1. A "non-essential" amino acid residue is a residue that can be altered from the wild-type sequence of BFLP1698 without altering the biological activity, whereas an "essential" amino acid residue is required for biological activity. For example, altering amino acid residues that are conserved among the BFLP1698 proteins of the present invention, is likely to result in loss of activity of the BFLP1698 protein.

Another aspect of the invention pertains to nucleic acid molecules encoding BFLP1698 proteins that contain changes in amino acid residues that are not essential for activity. Such BFLP1698 proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 75% homologous to the amino acid sequence of SEQ ID NO:2. Preferably, the protein encoded by the nucleic acid is at least about 80% homologous to SEQ ID NO:2, more preferably at least about 90%, 95%, 98%, and most preferably at least about 99% homologous to SEQ ID NO:2.

An isolated nucleic acid molecule encoding a BFLP1698 protein homologous to the protein of SEQ ID NO:2 can be created by introducing one or more nucleotide substitutions, additions or deletions into the nucleotide sequence of SEQ ID NO:1, such that one or more amino acid substitutions, additions or deletions are introduced into the encoded protein.

Mutations can be introduced into the nucleotide sequence of SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in BFLP1698 is replaced with another amino acid residue from the same side chain family. Alternatively, in another embodiment, mutations can be introduced randomly along all or part of a BFLP1698 coding sequence, such as by saturation mutagenesis, and the resultant mutants can be screened for BFLP1698 biological activity to identify mutants that retain activity. Following mutagenesis of SEQ ID NO:1 the encoded protein can be expressed by any recombinant technology known in the art and the activity of the protein can be determined.

In one embodiment, a mutant BFLP1698 protein can be assayed for (1) the ability to form protein:protein interactions with other BFLP1698 proteins, other cell-surface proteins, or biologically active portions thereof, (2) complex formation between a mutant BFLP1698 protein and a BFLP1698 receptor; (3) the ability of a mutant BFLP1698 protein to bind to an intracellular target protein or biologically active portion thereof; (e.g., avidin proteins); (4) the ability to bind BFLP1698 protein; or (5) the ability to specifically bind an anti-BFLP1698 protein antibody.

Antisense BFLP1698 Nucleic Acids

Another aspect of the invention pertains to isolated antisense nucleic acid molecules that are hybridizable to or complementary to the nucleic acid molecule comprising the nucleotide sequence of SEQ ID NO:1, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire BFLP1698 coding strand, or to only a portion thereof. Nucleic acid molecules encoding fragments, homologs, derivatives and analogs of a BFLP1698 protein of SEQ ID NO:2, or antisense nucleic acids complementary to a BFLP1698 nucleic acid sequence of SEQ ID NO:1 are additionally provided.

In one embodiment, an antisense nucleic acid molecule is antisense to a "coding region" of the coding strand of a nucleotide sequence encoding BFLP1698. The term "coding region" refers to the region of the nucleotide sequence comprising codons which are translated into amino acid residues (e.g., the protein coding region of human BFLP1698 corresponds to SEQ ID NO:2). In another embodiment, the antisense nucleic acid molecule is antisense to a "noncoding region" of the coding strand of a nucleotide sequence encoding BFLP1698. The term "noncoding region" refers to 5' and 3' sequences which flank the coding region that are not translated into amino acids (i.e., also referred to as 5' and 3' untranslated regions).

Given the coding strand sequences encoding BFLP1698 disclosed herein (e.g., SEQ ID NO:1), antisense nucleic acids of the invention can be designed according to the rules of Watson and Crick or Hoogsteen base pairing. The antisense nucleic acid molecule can be complementary to the entire coding region of BFLP1698 mRNA, but more preferably is an oligonucleotide that is antisense to only a portion of the coding or noncoding region of BFLP1698 mRNA. For example, the antisense oligonucleotide can be complementary to the region surrounding the translation start site of BFLP1698 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a BFLP1698 protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other. The antisense nucleic acid molecule can also comprise a 2'-o-methylribonucleotide.

Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

BFLP1698 Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as a mRNA, to which they have a complementary region. Thus, ribozymes (e.g., hammerhead ribozymes) can be used to catalytically cleave BFLP1698 mRNA transcripts to thereby inhibit translation of BFLP1698 mRNA. A ribozyme having specificity for a BFLP1698-encoding nucleic acid can be designed based upon the nucleotide sequence of a BFLP1698 DNA disclosed herein (i.e., SEQ ID NO:1). For example, a derivative of a Tetrahymena L-19 IVS RNA can be constructed in which the nucleotide sequence of the active site is complementary to the nucleotide sequence to be cleaved in a BFLP1698-encoding mRNA. Alternatively, BFLP1698 mRNA can be used to select a catalytic RNA having a specific ribonuclease activity from a pool of RNA molecules.

Alternatively, BFLP1698 gene expression can be inhibited by targeting nucleotide sequences complementary to the regulatory region of the BFLP1698 (e.g., the BFLP1698 promoter and/or enhancers) to form triple helical structures that prevent transcription of the BFLP1698 gene in target cells.

In various embodiments, the nucleic acids of BFLP1698 can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols.

PNAs of BFLP1698 can be used in therapeutic and diagnostic applications. For example, PNAs can be used as antisense or antigene agents for sequence-specific modulation of gene expression by, e.g., inducing transcription or translation arrest or inhibiting replication. PNAs of BFLP1698 can also be used, e.g., in the analysis of single base pair mutations in a gene by, e.g., PNA directed PCR clamping; as artificial restriction enzymes when used in combination with other enzymes, e.g., S1 nucleases; or as probes or primers for DNA sequence and hybridization.

In another embodiment, PNAs of BFLP1698 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of BFLP1698 can be generated that may combine the advantageous properties of PNA and DNA.

The oligonucleotide may include other appended groups such as peptides (e.g., for targeting host cell receptors in vivo), or agents facilitating transport across the cell membrane or the blood-brain barrier. In addition, oligonucleotides can be modified with hybridization triggered cleavage agents or intercalating agents. To this end, the oligonucleotide may be conjugated to another molecule, e.g., a peptide, a hybridization triggered cross-linking agent, a transport agent, a hybridization-triggered cleavage agent, etc.

BFLP1698 Interfering Nucleic Acids

Also provided by the invention is an isolated double-stranded nucleic acid (DNA or RNA) that is capable of mediating specific inhibition of BFLP1698 gene expression. In preferred embodiments, one or both strands of the double-stranded molecule is an RNA molecule. Preferably, each RNA strand has a length from 19-25, particularly from 19-23 nucleotides, more particularly from 20-22 nucleotides, and is capable of mediating BFLP1698 target-specific nucleic acid modifications, particularly RNA interference and/or DNA methylation. The double-stranded BFLP1698 molecule may be double stranded or have an overhang at one or both the 5' and/or 3' terminus. For example, the molecule may have a 3' overhang. The length of the 3'-overhang can be, e.g., 1-6 nucleotides, 2-5 nucleotides, 3-4 nucleotides, or 2 nucleotides. The length of the overhang may be the same or different for each strand. In one embodiment, dsRNAs are composed of two 21 nucleotide strands that are paired such that 1, 2, or 3 nucleotide overhangs are present on both ends of the double-stranded RNA.

The RNA strands preferably have 3'-hydroxyl groups. The 5'-terminus preferably includes a phosphate, diphosphate, triphosphate or hydroxyl group. If desired, the 3'-overhangs may be stabilized against degradation. For example, they may be selected such that they consist of purine nucleotides, particularly adenosine or guanosine nucleotides. Alternatively, pyrimidine nucleotides may be replaced with modified analogues, e.g. substitution of uridine-2 nucleotide 3' overhangs by 2'-deoxythymidine is tolerated, and does not affect the efficiency of RNA interference. The RNA molecule may contain at least one modified nucleotide analogue. The nucleotide analogues may be located at positions where the target-specific activity, e.g. the RNAi mediating activity is not substantially affected. The modified nucleotide is preferably present in a region at the 5'-end and/or the 3'-end of the double-stranded RNA molecule. In some embodiments, overhangs are stabilized by incorporating modified nucleotide analogues.

Nucleotide analogues can include sugar- or backbone-modified ribonucleotides. Other suitable nucleotides include a non-naturally occurring nucleobase instead of a naturally occurring nucleobases. For example, analogues can include uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. In preferred sugar-modified ribonucleotides the 2' OH-group is replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. In a preferred embodiment, where backbone-modified ribonucleotides are used as the phosphoester group connecting to adjacent ribonucleotides, they are replaced by a modified group, e.g. a phosphothioate group. It should be noted that the above modifications may be combined.

The BFLP1698 interfering RNA molecule can be a naturally isolated RNA molecule or can be a synthetic RNA molecule. Preferably, the BFLP1698 interfering RNA molecule is substantially free from contaminants occurring in cell extracts, e.g. from *Drosophila* embryos. Further, the BFLP1698 interfering RNA molecule is preferably substantially free from any non-target-specific contaminants, particularly non-target-specific RNA molecules e.g. from contaminants occurring in cell extracts.

Isolated double-stranded BFLP1698 interfering molecules can be used for mediating BFLP1698 target-specific nucleic acid modifications, particularly RNAi, in mammalian cells, particularly in human cells.

The sequence of the double-stranded BFLP1698 interfering molecule of the present invention is of sufficient identity to a nucleic acid BFLP1698 target molecule in order to effect target-specific interference of BFLP1698 gene expression and/or DNA methylation. Preferably, the sequence has an identity of at least 50%, particularly of at least 70% to the desired target molecule in the double-stranded portion of the RNA molecule. More preferably, the identity is at least 85% and most preferably 100% in the double-stranded portion of the RNA molecule. The identity of a BFLP1698 double-stranded interfering RNA molecule to a predetermined nucleic acid target molecule, e.g. an BFLP1698 mRNA target molecule with the sequence shown in SEQ ID NO:1, may be determined using the equation: $I=(n/L) \times 100$, wherein I is the identity in percent, n is the number of identical nucleotides in the double-stranded portion of the ds RNA and the target and L is the length of the sequence overlap of the double-stranded portion of the dsRNA and the target.

Alternatively, the identity of the double-stranded RNA molecule relative to the target sequence may also be defined including the 3' overhang, particularly an overhang having a length from 1-3 nucleotides. In this case the sequence identity is preferably at least 50%, more preferably at least 70% and most preferably at least 85% to the target sequence. For example, the nucleotides from the 3' overhang and up to 2 nucleotides from the 5' and/or 3' terminus of the double strand may be modified without significant loss of activity.

A double-stranded BFLP1698 RNA molecule may be prepared by a method that includes synthesizing two RNA strands each having a length from 19-25, e.g. from 19-23 nucleotides, wherein said RNA strands are capable of forming a double-stranded RNA molecule, wherein preferably at least one strand has a 3'-overhang from 1-5 nucleotides, and (b) combining the synthesized RNA strands under conditions, wherein a double-stranded RNA molecule is formed. The double-stranded RNA molecule is capable of mediating target-specific nucleic acid modifications, particularly RNA interference and/or DNA methylation.

Methods of synthesizing RNA molecules are known in the art. The single-stranded RNAs can also be prepared by enzymatic transcription from synthetic DNA templates or from DNA plasmids isolated from recombinant bacteria. Typically, phage RNA polymerases are used such as T7, T3 or SP6 RNA polymerase.

A further aspect of the present invention relates to a method of mediating BFLP1698-specific nucleic acid modifications, particularly RNA interference and/or DNA methylation in a cell or an organism by contacting the cell or organism with the double-stranded RNA molecule of the invention under conditions wherein target-specific nucleic acid modifications may occur and mediating a target-specific nucleic acid modification effected by the double-stranded RNA towards a BFLP1698 target nucleic acid.

BFLP1698 Polypeptides

A BFLP1698 polypeptide of the invention includes the BFLP1698-like protein whose sequence is provided in SEQ ID NO:2. The invention also includes a mutant or variant form of the disclosed BFLP1698 polypeptide, or of any of the fragments of the herein disclosed BFLP1698 polypeptide sequences.

Thus, a BFLP1698 polypeptide includes one in which any residues may be changed from the corresponding residue shown in SEQ ID NO:2 while still encoding a protein that maintains its BFLP1698-like activities and physiological functions, or a functional fragment thereof. In some embodiments, up to 20% or more of the residues may be so changed in the mutant or variant protein. In some embodiments, the BFLP1698 polypeptide according to the invention is a mature polypeptide.

Rapamycin Binding Domains

To identify regions of a BFLP1698 polypeptide sequence (e.g., a polypeptide including all or a portion of SEQ ID NO:2) containing rapamycin binding domains, the entire coding sequence, or a fragment of a BFLP1698 polypeptide sequence, is tested for its ability to bind rapamycin. Any technique known in the art for determining binding of a polypeptide to a small molecule can be used. For example, rapamycin can be labeled (i.e., with a non-radioactive label or with a radiolabel (e.g., $^{14}C$, $^{32}P$, $^{3}H$, or $^{125}I$), and mixed with a polypeptide containing some or all of a BFLP1698 polypeptide sequence. The polypeptide optionally includes a moiety that facilitates detection, e.g., the polypeptide can be a fusion polypeptide that includes a BFLP1698 sequence and a non-BFLP1698 polypeptide sequence.

A reagent specific for the polypeptide containing the BFLP1698 polypeptide sequence (e.g., an antibody specific for BFLP1698 or a probe specific for the non-BFLP1698 polypeptide in the case of a fusion polypeptide) is added to the mixture. Complexes that bind to the reagent are isolated, and the presence of label, which reveals the presence of rapamycin, is determined.

In general, a BFLP1698-like variant that preserves BFLP1698-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated BFLP1698 proteins, and biologically active portions thereof, or derivatives, fragments, analogs or homologs thereof. Fragments can comprise contiguous stretches of SEQ ID NO:2, or interspersed segments of SEQ ID NO:2. Also provided are polypeptide fragments suitable for use as immunogens to raise anti-BFLP1698 antibodies. In one embodiment, native BFLP1698 proteins can be isolated from cells or tissue sources by an appropriate purification scheme using standard protein purification techniques. In another embodiment, BFLP1698 proteins are produced by recombinant DNA techniques. Alternative to recombinant expression, a BFLP1698 protein or polypeptide can be synthesized chemically using standard peptide synthesis techniques.

A "purified" protein or biologically active portion thereof is substantially free of cellular material or other contaminating proteins from the cell or tissue source from which the BFLP1698 protein is derived, or substantially free from chemical precursors or other chemicals when chemically synthesized. The language "substantially free of cellular material" includes preparations of BFLP1698 protein in which the protein is separated from cellular components of the cells from which it is isolated or recombinantly produced. In one embodiment, the language "substantially free of cellular material" includes preparations of BFLP1698 protein having less than about 30% (by dry weight) of non-BFLP1698 protein (also referred to herein as a "contaminating protein"), more preferably less than about 20% of non-BFLP1698 protein, still more preferably less than about 10% of non-BFLP1698 protein, and most preferably less than about 5% non-BFLP1698 protein. When the BFLP1698 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BFLP1698 protein in which the protein is separated from chemical precursors or other chemicals that are involved in the synthesis of the protein. In one embodiment, the language "substantially free of chemical precursors or other chemicals" includes preparations of BFLP1698 protein having less than about 30% (by dry weight) of chemical precursors or non-BFLP1698 chemicals, more preferably less than about 20% chemical precursors or non-BFLP1698 chemicals, still more preferably less than about 10% chemical precursors or non-BFLP1698 chemicals, and most preferably less than about 5% chemical precursors or non-BFLP1698 chemicals.

Biologically active portions of a BFLP1698 protein include peptides comprising amino acid sequences sufficiently homologous to or derived from the amino acid sequence of the BFLP1698 protein, e.g., the amino acid sequence shown in SEQ ID NO:2 that include fewer amino acids than the full length BFLP1698 proteins, and exhibit at least one activity of a BFLP1698 protein. Typically, biologically active portions comprise a domain or motif with at least one activity of the BFLP1698 protein. A biologically active portion of a BFLP1698 protein can be a polypeptide which is, for example, 10, 25, 50, 100 or more amino acids in length.

A biologically active portion of a BFLP1698 protein of the present invention may contain at least one of the above-identified domains conserved between the BFLP1698 proteins. Moreover, other biologically active portions, in which other regions of the protein are deleted, can be prepared by recombinant techniques and evaluated for one or more of the functional activities of a native BFLP1698 protein.

In an embodiment, the BFLP1698 protein has an amino acid sequence shown in SEQ ID NO:2. In other embodiments, the BFLP1698 protein is substantially homologous to SEQ ID NO:2 and retains the functional activity of the protein of SEQ ID NO:2, yet differs in amino acid sequence due to natural allelic variation or mutagenesis, as described in detail below. Accordingly, in another embodiment, the BFLP1698 protein is a protein that comprises an amino acid sequence at least about 45% homologous to the amino acid sequence of SEQ ID NO:2 and retains the functional activity of the BFLP1698 proteins of SEQ ID NO:2.

Determining Homology Between Two or More Sequences

To determine the percent homology of two amino acid sequences or of two nucleic acid sequences, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO:1.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Chimeric and Fusion Proteins

The invention also provides BFLP1698 chimeric or fusion proteins. As used herein, a BFLP1698 "chimeric protein" or "fusion protein" comprises a BFLP1698 polypeptide operatively linked to a non-BFLP1698 polypeptide. A "BFLP1698 polypeptide" refers to a polypeptide having an amino acid sequence corresponding to BFLP1698, whereas a "non-BFLP1698 polypeptide" refers to a polypeptide having an amino acid sequence corresponding to a protein that is not substantially homologous to the BFLP1698 protein, e.g., a protein that is different from the BFLP1698 protein and that is derived from the same or a different organism. Within a BFLP1698 fusion protein the BFLP1698 polypeptide can correspond to all or a portion of a BFLP1698 protein. An example of a BFLP1698 fusion polypeptide is one that includes amino acids 21-230 of SEQ ID NO:2 (e.g., a polypeptide that includes amino acids 1-246 or amino acids 21-246 of SEQ ID NO:2). In one embodiment, a BFLP1698 fusion protein comprises at least one biologically active portion of a BFLP1698 protein. In another embodiment, a BFLP1698 fusion protein comprises at least two biologically active portions of a BFLP1698 protein. Within the fusion protein, the term "operatively linked" is intended to indicate that the BFLP1698 polypeptide and the non-BFLP1698 polypeptide are fused in-frame to each other. The non-BFLP1698 polypeptide can be fused to the N-terminus or C-terminus of the BFLP1698 polypeptide.

For example, in one embodiment a BFLP1698 fusion protein comprises a BFLP1698 polypeptide operably linked to either an extracellular domain of a second protein, i.e., non-BFLP1698 protein, or to the transmembrane and intracellular domain of a second protein, i.e., non-BFLP1698 protein. Such fusion proteins can be further utilized in screening assays for compounds that modulate BFLP1698 activity (such assays are described in detail below).

In another embodiment, the fusion protein is a GST-BFLP1698 fusion protein in which the BFLP1698 sequences are fused to the C-terminus of the GST (i.e., glutathione S-transferase) sequences. Such fusion proteins can facilitate the purification of recombinant BFLP1698.

In another embodiment, the fusion protein is a BFLP1698-immunoglobulin fusion protein in which the BFLP1698 sequences comprising one or more domains are fused to sequences derived from a member of the immunoglobulin protein family. Inhibition of the BFLP1698 ligand/BFLP1698 interaction can be used therapeutically for both the treatment of proliferative and differentiative disorders, e,g., cancer, modulating (e.g., promoting or inhibiting) cell survival as well as immunomodulatory disorders, autoimmunity, transplantation, and inflammation by alteration of cyotokine and chemokine cascade mechanisms. Moreover, the BFLP1698-immunoglobulin fusion proteins of the invention can be used as immunogens to produce anti-BFLP1698 antibodies in a subject, to purify BFLP1698 ligands, and in screening assays to identify molecules that inhibit the interaction of BFLP1698 with a BFLP1698 ligand.

A BFLP1698 chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence. Moreover, many expression vectors are commercially available that already encode a fusion moiety (e.g., a GST polypeptide). A BFLP1698-encoding nucleic acid can be cloned into such an expression vector such that the fusion moiety is linked in-frame to the BFLP1698 protein.

If desired, libraries of fragments of the BFLP1698 protein coding sequence can be used to generate a variegated population of BFLP1698 fragments for screening and subsequent selection of variants of a BFLP1698 protein.

BFLP1698 Antibodies

Also included in the invention are antibodies to BFLP1698 proteins, or fragments of BFLP1698 proteins. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$, and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated BFLP1698-related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO:2, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

Figure 2:
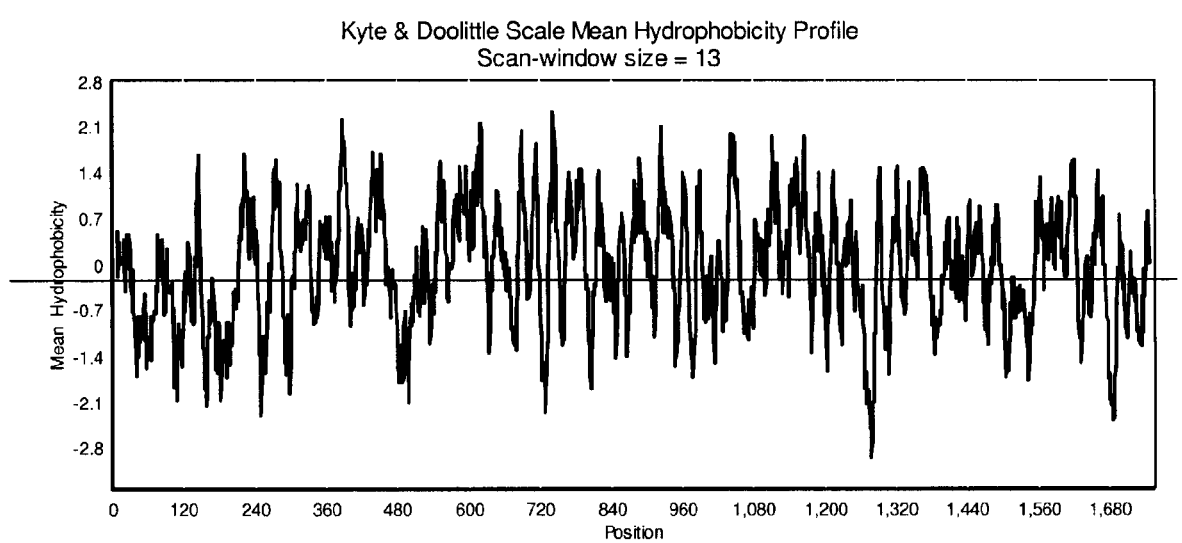
FIG. 2 Depicts a Kyte & Doolitle plot for the BFLP1698 protein.

In certain embodiments of the invention, at least one epitope encompassed by the antigenic peptide is a region of BFLP1698-related protein that is located on the surface of the protein, e.g., a hydrophilic region. A hydrophobicity analysis of the human BFLP1698-related protein sequence will indicate which regions of a BFLP1698-related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. A Kyte & Doolitle plot was generated for the BFLP1698 protein, and is shown in FIG. 2.

The novel nucleic acid encoding the BFLP1698 protein of the invention, or fragments thereof, may further be useful in diagnostic applications, wherein the presence or amount of the nucleic acid or the protein are to be assessed. These materials are further useful in the generation of antibodies that bind immunospecifically to the novel substances of the invention for use in therapeutic or diagnostic methods. The disclosed BFLP1698 protein has multiple hydrophilic regions, each of which can be used as an immunogen. In one embodiment, a contemplated BFLP1698 epitope is from about amino acids 1 to 60. In another embodiment, a BFLP1698 epitope is from about amino acids 70 to 80. In additional embodiments, BFLP1698 epitopes are from about amino acids 85 to 170, from about amino acids 180 to 190, from about amino acids 210 to 220, from about amino acids 230 to 260, from about amino acids 290 to 310, from about amino acids 350 to 360, from about amino acids 370 to 380, from about amino acids 400 to 430, from about amino acids 450 to 480, from about amino acids 520 to 540, from about amino acids 600 to 620, from about amino acids 630 to 640, from about amino acids 680 to 690, from about amino acids 730 to 740, from about amino acids 850 to 860, from about amino acids 870 to 890, from about amino acids 970 to 1010, from about amino acids 1030 to 1050, from about amino acids 1080 to 1130, from about amino acids 1150 to 1160, and from about amino acids 1180 to 1190.

Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof. The term "monoclonal antibody" (MAb) or "monoclonal antibody composition", as used herein, refers to a population of antibody molecules that contain only one molecular species of antibody molecule consisting of a unique light chain gene product and a unique heavy chain gene product.

The antibodies directed against the protein antigens of the invention can further comprise humanized antibodies or human antibodies. The humanized forms of antibodies include_chimeric immunoglobulins, immunoglobulin chains or fragments thereof (such as Fv, Fab, Fab', $F(ab')_2$ or other antigen-binding subsequences of antibodies) that are principally comprised of the sequence of a human immunoglobulin, and contain minimal sequence derived from a non-human immunoglobulin.

The antibodies can also be human antibodies, e.g., antibody molecules in which essentially the entire sequences of both the light chain and the heavy chain, including the CDRs, arise from human genes. Human monoclonal antibodies can be prepared by the trioma technique; the human B-cell hybridoma technique and the EBV hybridoma technique.

Human antibodies can also be produced using phage display libraries, or by introducing human immunoglobulin loci into transgenic animals, e.g., mice in which the endogenous immunoglobulin genes have been partially or completely inactivated. Human antibodies may additionally be produced using transgenic nonhuman animals that are modified so as to produce fully human antibodies rather than the animal's endogenous antibodies in response to challenge by an antigen.

The invention also provides single-chain antibodies specific to an antigenic protein of the invention. In addition, methods can be adapted for the construction of $F_{ab}$ expression libraries to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Also provided by the invention are bispecific antibodies. Bispecific antibodies are monoclonal, preferably human or humanized, antibodies that have binding specificities for at least two different antigens. One of the binding specificities is for an antigenic protein of the invention. The second binding target is any other antigen, and advantageously is a cell-surface protein or receptor or receptor subunit.

If desired, antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions.

Bispecific antibodies can be provided as full length antibodies or antibody fragments (e.g. F(ab')$_2$ bispecific antibodies).

Also within the invention are antibodies with more than two valencies (such as trispecific antibodies).

Exemplary bispecific antibodies bind to two different epitopes, at least one of which originates in the protein antigen of the invention.

The invention also includes heteroconjugate antibodies, which include two covalently joined antibodies.

The antibody of the invention can be modified to alter (e.g., enhance or diminish) its function. For example, cysteine residue(s) can be introduced into the Fc region, thereby allowing interchain disulfide bond formation in this region. The invention also includes immunoconjugates that include an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

The antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

BFLP1698 Recombinant Expression Vectors and Host Cells

Another aspect of the invention pertains to vectors, preferably expression vectors, containing a nucleic acid encoding a BFLP1698 protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genomic sequence into which they have integrated. Moreover, certain vectors are capable of directing the expression of genes to which they are operatively-linked. Such vectors are referred to herein as "expression vectors". "Plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Regulatory sequences include those that direct constitutive expression of a nucleotide sequence in many types of host cell and those that direct expression of the nucleotide sequence only in certain host cells (e.g., tissue-specific regulatory sequences). The expression vectors of the invention can be introduced into host cells to thereby produce proteins or peptides, including fusion proteins or peptides, encoded by nucleic acids as described herein (e.g., BFLP1698 proteins, mutant forms of BFLP1698 proteins, fusion proteins, etc.).

The recombinant expression vectors of the invention can be designed for expression of BFLP1698 proteins in prokaryotic or eukaryotic cells. For example, BFLP1698 proteins can be expressed in bacterial cells such as *Escherichia coli*, insect cells (using baculovirus expression vectors) yeast cells or mammalian cells. Alternatively, the recombinant expression vector can be transcribed and translated in vitro, for example using T7 promoter regulatory sequences and T7 polymerase.

In yet another embodiment, a nucleic acid of the invention is expressed in mammalian cells using a mammalian expression vector. Examples of mammalian expression vectors include pCDM8 and pMT2PC. When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific), lymphoid-specific promoters, in particular promoters of T cell receptors and immunoglobulins, neuron-specific promoters (e.g., the neurofilament promoter), pancreas-specific promoters, and mammary gland-specific promoters (e.g., milk whey promoter). Developmentally-regulated promoters are also encompassed, e.g., the murine hox promoters and the α-fetoprotein promoter.

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to BFLP1698 mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, BFLP1698 protein can be expressed in bacterial cells such as *E. coli*, insect cells, yeast or mammalian cells (such as human, Chinese hamster ovary cells (CHO) or COS cells). Other suitable host cells are known to those skilled in the art.

A gene that encodes a selectable marker (e.g., resistance to antibiotics) is generally introduced into the host cells along with the gene of interest. Various selectable markers include those that confer resistance to drugs, such as G418, hygromycin and methotrexate. A nucleic acid encoding a selectable marker can be introduced into a host cell on the same vector as that encoding BFLP1698 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) BFLP1698 protein. Accordingly, the invention further provides methods for producing BFLP1698 protein using the host cells of the invention. In one embodiment, the method comprises culturing the host cell of invention (into which a recombinant expression vector encoding BFLP1698 protein has been introduced) in a suitable medium such that BFLP1698 protein is produced. In another embodiment, the method further comprises isolating BFLP1698 protein from the medium or the host cell.

Transgenic BFLP1698 Animals

The host cells of the invention can also be used to produce non-human transgenic animals. For example, in one embodiment, a host cell of the invention is a fertilized oocyte or an embryonic stem cell into which BFLP1698 protein-coding sequences have been introduced. Such host cells can then be used to create non-human transgenic animals in which exogenous BFLP1698 sequences have been introduced into their genome or homologous recombinant animals in which endogenous BFLP1698 sequences have been altered. Such animals are useful for studying the function and/or activity of BFLP1698 protein and for identifying and/or evaluating modulators of BFLP1698 protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous BFLP1698 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing BFLP1698-encoding nucleic acid into the male pronuclei of a fertilized oocyte (e.g., by microinjection, retroviral infection) and allowing the oocyte to develop in a pseudopregnant female foster animal. Sequences including SEQ ID NO:1 can be introduced as a transgene into the genome of a non-human animal. Alternatively, a non-human homologue of the human BFLP1698 gene, such as a mouse BFLP1698 gene, can be isolated based on hybridization to the human BFLP1698 cDNA (described further supra) and used as a transgene. Intronic sequences and polyadenylation signals can also be included in the transgene to increase the efficiency of expression of the transgene. A tissue-specific regulatory sequence(s) can be operably-linked to the BFLP1698 transgene to direct expression of BFLP1698 protein to particular cells. Methods for generating transgenic animals via embryo manipulation and microinjection, particularly animals such as mice, have become conventional in the art. Similar methods are used for production of other transgenic animals. A transgenic founder animal can be identified based upon the presence of the BFLP1698 transgene in its genome and/or expression of BFLP1698 mRNA in tissues or cells of the animals. A transgenic founder animal can then be used to breed additional animals carrying the transgene. Moreover, transgenic animals carrying a transgene-encoding BFLP1698 protein can further be bred to other transgenic animals carrying other transgenes.

To create a homologous recombinant animal, a vector is prepared which contains at least a portion of a BFLP1698 gene into which a deletion, addition or substitution has been introduced to thereby alter, e.g., functionally disrupt, the BFLP1698 gene. The BFLP1698 gene can be a human gene (e.g., the DNA of SEQ ID NO:1), but more preferably, is a non-human homologue of a human BFLP1698 gene. For example, a mouse homologue of human BFLP1698 gene of SEQ ID NO:1 can be used to construct a homologous recombination vector suitable for altering an endogenous BFLP1698 gene in the mouse genome. In one embodiment, the vector is designed such that, upon homologous recombination, the endogenous BFLP1698 gene is functionally disrupted (i.e., no longer encodes a functional protein; also referred to as a "knock out" vector).

Alternatively, the vector can be designed such that, upon homologous recombination, the endogenous BFLP1698 gene is mutated or otherwise altered but still encodes functional protein (e.g., the upstream regulatory region can be altered to thereby alter the expression of the endogenous BFLP1698 protein). In the homologous recombination vector, the altered portion of the BFLP1698 gene is flanked at its 5'- and 3'-termini by additional nucleic acid of the BFLP1698 gene to allow for homologous recombination to occur between the exogenous BFLP1698 gene carried by the vector and an endogenous BFLP1698 gene in an embryonic stem cell. The additional flanking BFLP1698 nucleic acid is of sufficient length for successful homologous recombination with the endogenous gene. Typically, several kilobases of flanking DNA (both at the 5'- and 3'-termini) are included in the vector. The vector is then introduced into an embryonic stem cell line (e.g., by electroporation) and cells in which the introduced BFLP1698 gene has homologously-recombined with the endogenous BFLP1698 gene are selected.

The selected cells are then injected into a blastocyst of an animal (e.g., a mouse) to form aggregation chimeras. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system. Another example of a recombinase system is the FLP recombinase system of *Saccharomyces cerevisiae*. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in the art. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Methods of Detecting BFLP1698 Nucleic Acids and Diagnosing Lupus Nephritis

Reagents that detect BFLP1698 nucleic acids and/or polypeptides can be used to detect levels of BFLP1698 RNA and/or proteins sequences in a sample. Because elevated levels of BFLP1698 RNA are found in animals with lupus nephritis, detection of enhanced levels of BFLP1698 RNA and/or BFLP1698 polypeptides indicates the presence or predisposition to lupus in the subject. In addition, lowered levels of BFLP1698 RNA in treated lupus subjects as compared to untreated lupus indicates a return to a non-lupus state. Thus, the efficacy of lupus treatment can be monitored by comparing BFLP1698 RNA or protein levels in a sample from a treated population to samples in a diseased but untreated sample, (or a sample from an individual that has been treated for a shorter period of time).

Levels of BFLP1698 RNA can be assessed by comparing levels in a test cell population, from a subject whose lupus status is unknown, to levels in a reference cell population whose lupus status is known. Thus, the test cell population will typically include at least one cell that is capable of expressing a BFLP1698 gene. By "capable of expressing" is meant that the gene is present in an intact form in the cell and can be expressed. Expression of the BFLP1698 sequence is then detected, if present, and, preferably, measured using methods known in the art. For example, the BFLP1698 sequences disclosed herein can be used to construct probes for detecting BFLP1698 RNA sequences in, e.g., northern blot hybridization analyses or methods which specifically, and, preferably, quantitatively amplify BFLP1698 specific nucleic acid sequences. Alternatively, the sequences can be used to construct primers for specifically amplifying the BFLP1698 sequences in, e.g., amplification-based detection methods such as reverse-transcription based polymerase chain reaction.

BFLP1698 expression can be also measured at the protein level, i.e., by measuring the levels of BFLP1698 polypeptides. Such methods are well known in the art and include, e.g., immunoassays based on antibodies to proteins encoded by the genes.

Expression of sequences in test and control populations of cells can be compared using any art-recognized method for comparing expression of nucleic acid sequences. Whether or not comparison of the gene expression profile in the test cell population to the reference cell population reveals the presence, or degree, of the measured parameter depends on the composition of the reference cell population. For example, if the reference cell population is composed of cells from a lupus free subject, a similar gene expression level in the test cell population and a reference cell population indicates the test cell population is from a lupus free subject. Conversely, if the reference cell population is made up of cells from a diseased subject, a similar gene expression profile between the test cell population and the reference cell population indicates the test cell population is from a subject with lupus.

In various embodiments, a BFLP1698 sequence in a test cell population is considered comparable in expression level to the expression level of the ADIPO sequence in the reference cell population if its expression level varies within a factor of 2.0, 1.5, or 1.0 fold to the level of the BFLP1698 transcript in the reference cell population. In various embodiments, a BFLP1698 sequence in a test cell population can be considered altered in levels of expression if its expression level varies from the reference cell population by more than 1.0, 1.5, 2.0 or more fold from the expression level of the corresponding BFLP1698 sequence in the reference cell population.

If desired, comparison of differentially expressed sequences between a test cell population and a reference cell population can be done with respect to a control nucleic acid whose expression is independent of the parameter or condition being measured. Expression levels of the control nucleic acid in the test and reference nucleic acid can be used to normalize signal levels in the compared populations. Suitable control nucleic acids can readily be determined by one of ordinary skill in the art.

In some embodiments, the test cell population is compared to multiple reference cell populations. Each of the multiple reference populations may differ in the known parameter. Thus, a test cell population may be compared to a first reference cell population from a subject known to have lupus, as well as a second reference population known to not have lupus.

The test cell population that is exposed can be any number of cells, i.e., one or more cells, and can be provided in vitro, in vivo, or ex vivo.

Preferably, cells in the reference cell population are derived from a tissue type as similar as possible to test cell, e.g., renal tissue. In some embodiments, the control cell is derived from the same subject as the test cell. In other embodiments, the reference cell population is derived from a plurality of cells from multiple subjects. For example, the reference cell population can be a database of expression patterns from previously tested cells.

The subject is preferably a mammal. The mammal can be, e.g., a human, non-human primate, mouse, rat, dog, cat, horse, or cow.

Pharmaceutical Compositions

The BFLP1698 nucleic acid molecules, BFLP1698 proteins, and anti-BFLP1698 antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration.

Pharmaceutical compositions suitable for injectable use include sterile aqueous solutions (where water soluble) or dispersions and sterile powders for the extemporaneous preparation of sterile injectable solutions or dispersion.

Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

Screening and Detection Methods

The isolated nucleic acid molecules of the invention can be used to express BFLP1698 protein (e.g., via a recombinant expression vector in a host cell in gene therapy applications), to detect BFLP1698 mRNA (e.g., in a biological sample) or a genetic lesion in a BFLP1698 gene, and to modulate BFLP1698 activity, as described further, below. In addition, the BFLP1698 proteins can be used to screen drugs or compounds that modulate the BFLP1698 protein activity or expression as well as to treat disorders characterized by insufficient or excessive production of BFLP1698 protein or production of BFLP1698 protein forms that have decreased or aberrant activity compared to BFLP1698 wild-type protein. In addition, the anti-BFLP1698 antibodies of the invention can be used to detect and isolate BFLP1698 proteins and modulate BFLP1698 activity. For example, BFLP1698 activity includes T-cell or NK cell growth and differentiation, antibody production, and tumor growth.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to BFLP1698 proteins or have a stimulatory or inhibitory effect on, e.g., BFLP1698 protein expression or BFLP1698 protein activity. The invention also includes compounds identified in the screening assays described herein.

In one embodiment, the screening assays are used to identify therapeutic agents for treating autoimmune diseases. The autoimmune disease can be, e.g., lupus, including lupus nephritis.

In one embodiment, the invention provides assays for screening candidate or test compounds which bind to or modulate the activity of the membrane-bound form of a BFLP1698 protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds.

A "small molecule" as used herein, is meant to refer to a composition that has a molecular weight of less than about 5 kD and most preferably less than about 4 kD. Small molecules can be, e.g., rapamycin, nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention. The libraries of compounds may be presented in solution, or on beads, on chips, bacteria, spores, plasmids or on phage In one embodiment, an assay is a cell-based assay in which a cell which expresses a membrane-bound form of BFLP1698 protein, or a biologically-active portion thereof, on the cell surface is contacted with a test compound and the ability of the test compound to bind to a BFLP1698 protein determined. The cell, for example, can be of mammalian origin or a yeast cell. Determining the ability of the test compound to bind to the BFLP1698 protein can be accomplished, for example, by coupling the test compound with a radioisotope or enzymatic label such that binding of the test compound to the BFLP1698 protein or biologically-active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of BFLP1698 protein, or a biologically-active portion thereof, on the cell surface with a known compound which binds BFLP1698 to form an assay mixture, contacting the assay mixture with a test compound, and determining the ability of the test compound to interact with a BFLP1698 protein, wherein determining the ability of the test compound to interact with a BFLP1698 protein comprises determining the ability of the test compound to preferentially bind to BFLP1698 protein or a biologically-active portion thereof as compared to the known compound.

In another embodiment, an assay is a cell-based assay comprising contacting a cell expressing a membrane-bound form of BFLP1698 protein, or a biologically-active portion thereof, on the cell surface with a test compound and determining the ability of the test compound to modulate (e.g., stimulate or inhibit) the activity of the BFLP1698 protein or biologically-active portion thereof. Determining the ability of the test compound to modulate the activity of BFLP1698 or a biologically-active portion thereof can be accomplished, for example, by determining the ability of the BFLP1698 protein to bind to or interact with a BFLP1698 target molecule. As used herein, a "target molecule" is a molecule with which a BFLP1698 protein binds or interacts in nature, for example, a molecule on the surface of a cell which expresses a BFLP1698 interacting protein, a molecule on the surface of a second cell, a molecule in the extracellular milieu, a molecule associated with the internal surface of a cell membrane or a cytoplasmic molecule. A BFLP1698 target molecule can be a non-BFLP1698 molecule or a BFLP1698 protein or polypeptide of the invention In one embodiment, a BFLP1698 target molecule is a component of a signal transduction pathway that facilitates transduction of an extracellular signal (e.g. a signal generated by binding of a compound to a membrane-bound BFLP1698 molecule) through the cell membrane and into the cell. The target, for example, can be a second intercellular protein that has catalytic activity or a protein that facilitates the association of downstream signaling molecules with BFLP1698.

Determining the ability of the BFLP1698 protein to bind to or interact with a BFLP1698 target molecule can be accomplished by one of the methods described above for determining direct binding. In one embodiment, determining the ability of the BFLP1698 protein to bind to or interact with a BFLP1698 target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a BFLP1698-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a BFLP1698 protein or biologically-active portion thereof with a test compound and determining the ability of the test compound to bind to the BFLP1698 protein or biologically-active portion thereof. Binding of the test compound to the BFLP1698 protein can be determined either directly or indirectly as described above. In one such embodiment, the assay comprises contacting the BFLP1698 protein or biologically-active portion thereof with a known compound which binds BFLP1698 to form an assay mixture, contacting the assay mixture with a test compound, and determining the ability of the test compound to interact with a BFLP1698 protein, wherein determining the ability of the test compound to interact with a BFLP1698 protein comprises determining the ability of the test compound to preferentially bind to BFLP1698 or a biologically-active portion thereof as compared to the known compound.

In still another embodiment, an assay is a cell-free assay comprising contacting BFLP1698 protein or a biologically-active portion thereof with a test compound and determining the ability of the test compound to modulate (e.g. stimulate or inhibit) the activity of the BFLP1698 protein or a biologically-active portion thereof. Determining the ability of the test compound to modulate the activity of BFLP1698 can be accomplished, for example, by determining the ability of the BFLP1698 protein to bind to a BFLP1698 target molecule by one of the methods described above for determining direct binding. In an alternative embodiment, determining the ability of the test compound to modulate the activity of BFLP1698 protein can be accomplished by determining the ability of the BFLP1698 protein further modulate a BFLP1698 target molecule. For example, the catalytic/enzymatic activity of the target molecule on an appropriate substrate can be determined as described above.

In yet another embodiment, the cell-free assay comprises contacting the BFLP1698 protein or a biologically-active portion thereof with a known compound which binds BFLP1698 protein to form an assay mixture, contacting the assay mixture with a test compound, and determining the ability of the test compound to interact with a BFLP1698 protein, wherein determining the ability of the test compound to interact with a BFLP1698 protein comprises determining the ability of the BFLP1698 protein to preferentially bind to or modulate the activity of a BFLP1698 target molecule.

The cell-free assays of the invention are amenable for use with both the soluble form or the membrane-bound form of BFLP1698 protein. In the case of cell-free assays comprising the membrane-bound form of BFLP1698 protein, it may be desirable to utilize a solubilizing agent such that the membrane-bound form of BFLP1698 protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the invention, it may be desirable to immobilize either BFLP1698 protein or its target molecule to facilitate separation of complexed from uncomplexed forms of one or both of the proteins, as well as to accommodate automation of the assay. Binding of a test compound to BFLP1698 protein, or interaction of BFLP1698 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-BFLP1698 fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or BFLP1698 protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of BFLP1698 protein binding or activity determined using standard techniques.

Other techniques for immobilizing proteins on matrices can also be used in the screening assays of the invention. For example, either the BFLP1698 protein or its target molecule can be immobilized utilizing conjugation of biotin and streptavidin. Biotinylated BFLP1698 protein or target molecules can be prepared from biotin-NHS(N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with BFLP1698 protein or target molecules, but which do not interfere with binding of the BFLP1698 protein to its target molecule, can be derivatized to the wells of the plate, and unbound target or BFLP1698 protein trapped in the wells by antibody conjugation. Methods for detecting such complexes, in addition to those described above for the GST-immobilized complexes, include immunodetection of complexes using antibodies reactive with the BFLP1698 protein or target molecule, as well as enzyme-linked assays that rely on detecting an enzymatic activity associated with the BFLP1698 protein or target molecule.

In another embodiment, modulators of BFLP1698 protein expression are identified in a method wherein a cell is contacted with a candidate compound and the expression of BFLP1698 mRNA or protein in the cell is determined. The level of expression of BFLP1698 mRNA or protein in the presence of the candidate compound is compared to the level of expression of BFLP1698 mRNA or protein in the absence of the candidate compound. The candidate compound can then be identified as a modulator of BFLP1698 mRNA or protein expression based upon this comparison. For example, when expression of BFLP1698 mRNA or protein is greater (i.e., statistically significantly greater) in the presence of the candidate compound than in its absence, the candidate compound is identified as a stimulator of BFLP1698 mRNA or protein expression. Alternatively, when expression of BFLP1698 mRNA or protein is less (statistically significantly less) in the presence of the candidate compound than in its absence, the candidate compound is identified as an inhibitor of BFLP1698 mRNA or protein expression. The level of BFLP1698 mRNA or protein expression in the cells can be determined by methods described herein for detecting BFLP1698 mRNA or protein.

In yet another aspect of the invention, the BFLP1698 proteins can be used as "bait proteins" in a two-hybrid assay or three hybrid assay, to identify other proteins that bind to or interact with BFLP1698 ("BFLP1698-binding proteins" or "BFLP1698-bp") and modulate BFLP1698 activity. Such BFLP1698-binding proteins are also likely to be involved in the propagation of signals by the BFLP1698 proteins as, for example, upstream or downstream elements of the BFLP1698 pathway.

The two-hybrid system is based on the modular nature of most transcription factors, which consist of separable DNA-binding and activation domains. Briefly, the assay utilizes two different DNA constructs. In one construct, the gene that codes for BFLP1698 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a BFLP1698-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with BFLP1698.

The invention further pertains to novel agents identified by the aforementioned screening assays and uses thereof for treatments as described herein.

The invention will be illustrated in the following non-limiting examples.

EXAMPLE 1

Expression Patterns of Murine BFLP1698 Sequence in Disease-Free, Lupus Nephritis Simulated Disease, and Rapamycin-Treated Diseased Mice The expression of murine BFLP1698 sequences were examined in mice that developed lupus nephritis-like symptoms in the NZBxNZW murine model. Expression in diseased mice was compared to expression of the sequences in non-diseased mice of varying ages, and in mice whose lupus nephritis-like symptoms diminished following treatment with rapamycin or anti-B7 antibodies.

Mice were obtained from Jackson Laboratories at 6 to 8 weeks of age and aged on site. Data were obtained from kidneys of mice and harvested at the indicated time point: C57BL/6 female mice at 8, and 32 weeks, F1(NZBxNZW) female mice 12, 25, and 42 weeks, mice treated with rapamycin at 42 and 55 weeks, mice treated with antibodies to B7.1 and B7.2 at 52 weeks. Each group contained three mice.

Rapamycin treated mice received 5 mg/kg rapamycin subcutaneous injection 3 times per week for 8 weeks staring at 29 weeks of age. Control mice received injections of vehicle (methyl cellulose) on the same schedule. Effectiveness of therapy was determined by normalization of proteinuria and kidney histology (data not shown). Gene expression analysis was preformed on mice sacrificed at the end of the treatment course (36 weeks of age, data not shown), and at 42 weeks (6 weeks after treatment) and 55 weeks (20 weeks after treatment).

Mice treated with anti-B7 received 200 μg of anti-B7.1 (1G10F9 monoclonal) and 200 μg of anti-B7.2 (GL1 monoclonal) by intra-peritoneal injections 3 times per week for two weeks starting at 29 weeks of age. Gene expression analysis was performed 21 weeks after treatment.

RNA Isolation and Hybridization to Oligonucleotide Arrays

Kidneys from both male and female mice were collected and snap frozen for RNA isolation. One half each kidney was used. A longitudinal section of the left kidney and a cross section of the right kidney was used in for each individual animal.

Snap frozen mouse kidney tissue was homogenized using homogenizer suspended in RLT buffer plus 2ME for 30 to 45 seconds. Total RNA was prepared using the Qiagen Midi Kit following the manufacturer's protocol. RNA was suspended in DEPC treated H2O and quantified by OD 280.

cDNA was synthesized from 5 ug of total RNA using the Superscript Kit (BRL). cDNA was purified using phenol:cloroform:isoamyl alcohol (25:24:1) with a Phage lock gel tube following the Phage lock protocol. Supernanant was collected and cleaned up using EtOH. Sample was resuspended in DEPC treated H2O.

In vitro T7 polymerase driven transcription reactions for synthesis and biotin labeling of antisense cRNA. Qiagen RNeasy spin column purification used used to purify the cRNA. GeneChip hybridization mixtures contained 15 ug fragmented cRNA, 0.5 mg/ml acetylated BSA, 0.1 mg/ml herring sperm DNA, in 1×MES buffer in a total volume of 200 ul as per manufactures instructions. Reaction mixtures were hybridized for 16 hr at 45° C. to Affymetrix Mu11KsubA and Mu11KsubB oligonucleotide arrays. The hybridization mixtures were removed and the arrays were washed and stained with Streptavidin R-phycoerthrin (Molecular Probes) using GeneChip Fluidics Station 400 and scanned with a Hewlett Packard GeneArray Scanner following manufactures instructions. Fluorescent data was collected and converted to gene specific difference average using MicroArray Suite software.

Analysis of Oligonucleotide Array Data

An eleven member standard curve, comprised of gene fragments derived from cloned bacterial and bacteriophage sequences were spiked into each hybridization mixture at concentrations ranging from 0.5 pM to 150 pM representing RNA frequencies of approximately 3.3 to 1000 parts per million (ppm). The biotinylated standard curve fragments were synthesized by T7-polymerase driven IVT reactions from plasmid-based templates. The spiked biotinylated RNA fragments serve both as an internal standard to assess chip sensitivity and as standard curve to convert measured fluorescent difference averages from individual genes into RNA frequencies in ppm as described by Hill et al.

Gene expression frequencies from each individual mouse kidney were measured and the expression data subjected to statistical analysis. Frequency values determined from individual measurements for a given group of mice were averaged. Genes whose frequencies differed significantly between C57Bl6 kidneys at 12 and 32 weeks of age were classified as changing as a result of the normal aging process, and not due to a disease process.

Expression frequencies in young (disease-free), old (diseased), and effectively treated old (disease-free) F1(NZB×NZW) mice and C57BL6 control mice of oligonucleotide sequence identified on the Affymetrix Murine 11K chip by the qualifier aa002653_s_at are shown. This sequence represents an unknown mouse gene.

The results are shown in FIG. 1. Shown is a histogram showing gene expression levels in kidneys from the indicated mice. Expression levels of BFLP1698 do not vary significantly between C57BL/6 kidneys at 12 weeks of age and kidney at 32 weeks of age, indicating that expression levels do not increase with age in kidneys of non-diseased mice. In (NXB×NZW)F1 kidneys, the gene is expressed at normal levels prior to disease onset (12 weeks of age). As the mice age and disease progresses, increasing expression levels are observed at 25 weeks, 36 weeks (data not shown for 36 weeks), and 42 weeks. By 55 weeks of age, the mice have died due to kidney failure. Mice treated with rapamycin for 8 weeks with treatment starting at 29 weeks of age, remain healthy-past 55 weeks of age. Kidneys of mice that have received effective therapy (either rapamycin therapy or anti-B7 therapy) express normal levels of BFLP1698, and these normal levels persist in asymptomatic kidney 20 weeks after cessation of rapamycin therapy and 15 weeks after cessation of anti-B7 therapy. The observation that expression levels return to normal when kidney function is normal indicates that elevated levels are related to, and diagnostic of, disease progression. Blocking the function of these genes may inhibit or retard disease progression. Expression levels may also to used to assess and compare effectiveness of various therapeutic interventions.

EXAMPLE 2

A Variant of the Human BFLP1698 Polypeptide Sequence Shown in Table 2

A polypeptide sequence varying by one amino acid from the BFLP1698 amino acid sequence presented in Table 2 is shown below. For the sequence shown, the F at position 97 of the BFLP1698 sequence shown in Table 2 has been replaced by an L, which is shown in bold font.

```
                                            (SEQ ID NO:3)
MALVPGRSKEDGLWTRNSPGSSQHPESPRLPNPLWDRGKIGKVEGHQHIQ

DFSQKSHLPSIVVESSEVNEESGDLHLPHEELLLLTDGEEEDAEAFLQDQ

SEEPGAARPHHQARQVEHSTQRGHLEIRELKKKLFKRRRVLNRERRLRHR

VVGAVIDQGLITRHHLKKRAAQELSQEIKAFLTGVDPILGHQLSAREHAR

CGLLLLLRSLPPARAAVLDHLRGVFDESVRAHLAALDETPVAGPPHLRPPP

PSHVPAGGPGLEDVVQEVQQVLSEFIRANPKAWAPVISAWSIDLMGQLSS

TYSGQHQRVPHATGALNELLQLWMGCRATRTLMDIYVQCLSALIGSCPDA

CVDALLDTSVQHSPHFDWVVAHIGSSFPGTIISRVLSCGLKDFCVHGGAG

GGAGSSGGSSSQTPSTDPFPGSPAIPAEKRVPKIASVVGILGHLASRHGD

SIRRELLRMFHDSLAGGSGGRSGDPSLQATVPFLLQLAVMSPALLGTVSG

ELVDCLKPPAVLSQLQQHLQGFPREELDNMLNLAVHLVSQASGAGAYRLL

QFLVDTAMPASVITTQGLAVPDTVREACDRLIQLLLLHLQKLVHHRGGSP

GEGVLGPPPPPRLVPFLDALKNHVGELCGETLRLERKRFLWQHQLLGLLS

VYTRPSCGPEALGHLLSRARSPEELSLATQLYAGLVVSLSGLLPLAFRSC

LARVHAGTLQPPFTARFLRNLALLVGWEQQGGEGPAALGAHFGESASAHL

SDLAPLLLHPEEEVAEAAASLLAICPFPSEALSPSQLLGLVRAGVHRFFA

SLRLHGPPGVASACQLLTRLSQTSPAGLKAVLQLLVEGALHRGNTELFGG

QVDGDNETLSVVSASLASASLLDTNRRHTAAVPGPGGIWSVFHAGVIGRG

LKPPKFVQSRNQQEVIYNTQSLLSLLVHCCSAPGGTECGECWGAPILSPE

AAKAVAVTLVESVCPDAAGAELAWPPEEHARATVERDLRIGRRFREQPLL
```

```
-continued
FELLKLVAAAPPALCYCSVLLRGLLAALLGHWEASRHPDTTHSPWHLEAS

CTLVAVMAEGSLLPPALGNMHEVFSQLAPFEVRLLLLSVWGFLREHGPLP

QKFIFQSERGRFIRDFSREGGGEGGPHLAVLHSVLHRNIDRLGLFSGRFQ

APSPSTLLRQGT
```

EXAMPLE 3

A Variant of the Human BFLP1698 Polypeptide Sequence Shown in Table 2

A polypeptide sequence varying by one amino acid from the BFLP1698 amino acid sequence presented in Table 2 is shown below. For the sequence shown, the Q at position 192 of the BFLP1698 sequence shown in Table 2 has been replaced by a N, which is shown in bold font.

```
                                              (SEQ ID NO: 4)
MALVPGRSKEDGLWTRNSPGSSQHPESPRLPNPLWDRGKIGK

VEGHQHIQDFSQKSHLPSIVVESSEVNEESGDLHLPHEELLLLTDGEEED

AEAFFQDQSEEPGAARPHHQARQVEHSTQRGHLEIRELKKKLFKRRRVLN

RERRLRHRVVGAVIDQGLITRHHLKKRAAQELSQEIKAFLTGVDPILGHN

LSAREHARCGLLLLRSLPPARAAVLDHLRGVFDESVRAHLAALDETPVAG

PPHLRPPPPSHVPAGGPGLEDVVQEVQQVLSEFIRANPKAWAPVISAWSI

DLMGQLSSTYSGQHQRVPHATGALNELLQLWMGCRATRTLMDIYVQCLSA

LIGSCPDACVDALLDTSVQHSPHFDWVVAHIGSSFPGTIISRVLSCGLKD

FCVHGGAGGGAGSSGGSSSQTPSTDPFPGSPAIPAEKRVPKIASVVGILG

HLASRHGDSIRRELLRMFHDSLAGGSGGRSGDPSLQATVPFLLQLAVMSP

ALLGTVSGELVDCLKPPAVLSQLQQHLQGFPREELDNMLNLAVHLVSQAS

GAGAYRLLQFLVDTAMPASVITTQGLAVPDTVREACDRLIQLLLLHLQKL

VHHRGGSPGEGVLGPPPPPRLVPFLDALKNHVGELCGETLRLERKRFLWQ

HQLLGLLSVYTRPSCGPEALGHLLSRARSPEELSLATQLYAGLVVSLSGL

LPLAFRSCLARVHAGTLQPPFTARFLRNLALLVGWEQQGGEGPAALGAHF

GESASAHLSDLAPLLLHPEEEVAEAAASLLAICPFPSEALSPSQLLGLVR

AGVHRFFASLRLHGPPGVASACQLLTRLSQTSPAGLKAVLQLLVEGALHR

GNTELFGGQVDGDNETLSVVSASLASASLLDTNRRHTAAVPGPGGIWSVF

HAGVIGRGLKPPKFVQSRNQQEVIYNTQSLLSLLVHCCSAPGGTECGECW

GAPILSPEAAKAVAVTLVESVCPDAAGAELAWPPEEHARATVERDLRIGR

RFREQPLLFELLKLVAAAPPALCYCSVLLRGLLAALLGHWEASRHPDTTH

SPWHLEASCTLVAVMAEGSLLPPALGNMHEVFSQLAPFEVRLLLLSVWGF

LREHGPLPQKFIFQSERGRFIRDFSREGGGEGGPHLAVLHSVLHRNIDRL

GLFSGRFQAPSPSTLLRQGT
```

EXAMPLE 4

A Variant of the Human BFLP1698 Polypeptide Sequence Shown in Table 2

A polypeptide sequence varying by one amino acid from the BFLP1698 amino acid sequence presented in Table 2 is shown below. For the sequence shown, the S at position 288 of the BFLP1698 sequence shown in Table 2 has been replaced by an G, which is shown in bold font.

```
                                              (SEQ ID NO: 5)
MALVPGRSKEDGLWTRNSPGSSQHPESPRLPNPLWDRGKIGK

VEGHQHIQDFSQKSHLPSIVVESSEVNEESGDLHLPHEELLLLTDGEEED

AEAFFQDQSEEPGAARPHHQARQVEHSTQRGHLEIRELKKKLFKRRRVLN

RERRLRHRVVGAVIDQGLITRHHLKKRAAQELSQEIKAFLTGVDPILGHQ

LSAREHARCGLLLLRSLPPARAAVLDHLRGVFDESVRAHLAALDETPVAG

PPHLRPPPPSHVPAGGPGLEDVVQEVQQVLSEFIRANPKAWAPVIGAWSI

DLMGQLSSTYSGQHQRVPHATGALNELLQLWMGCRATRTLMDIYVQCLSA

LIGSCPDACVDALLDTSVQHSPHFDWVVAHIGSSFPGTIISRVLSCGLKD

FCVHGGAGGGAGSSGGSSSQTPSTDPFPGSPAIPAEKRVPKIASVVGILG

HLASRHGDSIRRELLRMFHDSLAGGSGGRSGDPSLQATVPFLLQLAVMSP

ALLGTVSGELVDCLKPPAVLSQLQQHLQGFPREELDNMLNLAVHLVSQAS

GAGAYRLLQFLVDTAMPASVITTQGLAVPDTVREACDRLIQLLLLHLQKL

VHHRGGSPGEGVLGPPPPPRLVPFLDALKNHVGELCGETLRLERKRFLWQ

HQLLGLLSVYTRPSCGPEALGHLLSRARSPEELSLATQLYAGLVVSLSGL

LPLAFRSCLARVHAGTLQPPFTARFLRNLALLVGWEQQGGEGPAALGAHF

GESASAHLSDLAPLLLHPEEEVAEAAASLLAICPFPSEALSPSQLLGLVR

AGVHRFFASLRLHGPPGVASACQLLTRLSQTSPAGLKAVLQLLVEGALHR

GNTELFGGQVDGDNETLSVVSASLASASLLDTNRRHTAAVPGPGGIWSVF

HAGVIGRGLKPPKFVQSRNQQEVIYNTQSLLSLLVHCCSAPGGTECGECW

GAPILSPEAAKAVAVTLVESVCPDAAGAELAWPPEEHARATVERDLRIGR

RFREQPLLFELLKLVAAAPPALCYCSVLLRGLLAALLGHWEASRHPDTTH

SPWHLEASCTLVAVMAEGSLLPPALGNMHEVFSQLAPFEVRLLLLSVWGF

LREHGPLPQKFIFQSERGRFIRDFSREGGGEGGPHLAVLHSVLHRNIDRL

GLFSGRFQAPSPSTLLRQGT
```

EXAMPLE 5

A Variant of the Human BFLP1698 Polypeptide Sequence Shown in Table 2

A polypeptide sequence varying by one amino acid from the BFLP1698 amino acid sequence presented in Table 2 is shown below. For the sequence shown, the H at position 365 of the BFLP1698 sequence shown in Table 2 has been replaced by an R, which is shown in bold font.

```
                                              (SEQ ID NO: 6)
MALVPGRSKEDGLWTRNSPGSSQHPESPRLPNPLWDRGKIGK

VEGHQHIQDFSQKSHLPSIVVESSEVNEESGDLHLPHEELLLLTDGEEED

AEAFFQDQSEEPGAARPHHQARQVEHSTQRGHLEIRELKKKLFKRRRVLN

RERRLRHRVVGAVIDQGLITRHHLKKRAAQELSQEIKAFLTGVDPILGHQ

LSAREHARCGLLLLRSLPPARAAVLDHLRGVFDESVRAHLAALDETPVAG

PPHLRPPPPSHVPAGGPGLEDVVQEVQQVLSEFIRANPKAWAPVISAWSI
```

DLMGQLSSTYSGQHQRVPHATGALNELLQLWMGCRATRTLMDIYVQCLSA

LIGSCPDACVDALLDTSVQHSPRFDWVVAHIGSSFPGTIISRVLSCGLKD

FCVHGGAGGGAGSSGGSSSQTPSTDPFPGSPAIPAEKRVPKIASVVGILG

HLASRHGDSIRRELLRMFHDSLAGGSGGRSGDPSLQATVPFLLQLAVMSP

ALLGTVSGELVDCLKPPAVLSQLQQHLQGFPREELDNMLNLAVHLVSQAS

GAGAYRLLQFLVDTAMPASVITTQGLAVPDTVREACDRLIQLLLLHLQKL

VHHRGGSPGEGVLGPPPPPRLVPFLDALKNHVGELCGETLRLERKRFLWQ

HQLLGLLSVYTRPSCGPEALGHLLSRARSPEELSLATQLYAGLVVSLSGL

LPLAFRSCLARVHAGTLQPPFTARFLRNLALLVGWEQQGGEGPAALGAHF

GESASAHLSDLAPLLLHPEEEVAEAAASLLAICPFPSEALSPSQLLGLVR

AGVHRFFASLRLHGPPGVASACQLLTRLSQTSPAGLKAVLQLLVEGALHR

GNTELFGGQVDGDNETLSVVSASLASASLLDTNRRHTAAVPGPGGIWSVF

HAGVIGRGLKPPKFVQSRNQQEVIYNTQSLLSLLVHCCSAPGGTECGECW

GAPILSPEAAKAVAVTLVESVCPDAAGAELAWPPEEHARATVERDLRIGR

RFREQPLLFELLKLVAAAPPALCYCSVLLRGLLAALLGHWEASRHPDTTH

SPWHLEASCTLVAVMAEGSLLPPALGNMHEVFSQLAPFEVRLLLLSVWGF

LREHGPLPQKFIFQSERGRFIRDFSREGGGEGGPHLAVLHSVLHRNIDRL

GLFSGRFQAPSPSTLLRQGT

EXAMPLE 6

A Variant of the Human BFLP1698 Polypeptide Sequence Shown in Table 2

A polypeptide sequence varying by one amino acid from the BFLP1698 amino acid sequence presented in Table 2 is shown below. For the sequence shown, the V at position 481 of the BFLP1698 sequence shown in Table 2 has been replaced by an M, which is shown in bold font.

(SEQ ID NO: 7)
MALVPGRSKEDGLWTRNSPGSSQHPESPRLPNPLWDRGKIGK

VEGHQHIQDFSQKSHLPSIVVESSEVNEESGDLHLPHEELLLLTDGEEED

AEAFFQDQSEEPGAARPHHQARQVEHSTQRGHLEIRELKKKLFKRRRVLN

RERRLRHRVVGAVIDQGLITRHHLKKRAAQELSQEIKAFLTGVDPILGHQ

LSAREHARCGLLLLRSLPPARAAVLDHLRGVFDESVRAHLAALDETPVAG

PPHLRPPPPSHVPAGGPGLEDVVQEVQQVLSEFIRANPKAWAPVISAWSI

DLMGQLSSTYSGQHQRVPHATGALNELLQLWMGCRATRTLMDIYVQCLSA

LIGSCPDACVDALLDTSVQHSPHFDWVVAHIGSSFPGTIISRVLSCGLKD

FCVHGGAGGGAGSSGGSSSQTPSTDPFPGSPAIPAEKRVPKIASVVGILG

HLASRHGDSIRRELLRMFHDSLAGGSGGRSGDPSLQATMPFLLQLAVMSP

ALLGTVSGELVDCLKPPAVLSQLQQHLQGFPREELDNMLNLAVHLVSQAS

GAGAYRLLQFLVDTAMPASVITTQGLAVPDTVREACDRLIQLLLLHLQKL

VHHRGGSPGEGVLGPPPPPRLVPFLDALKNHVGELCGETLRLERKRFLWQ

HQLLGLLSVYTRPSCGPEALGHLLSRARSPEELSLATQLYAGLVVSLSGL

LPLAFRSCLARVHAGTLQPPFTARFLRNLALLVGWEQQGGEGPAALGAHF

GESASAHLSDLAPLLLHPEEEVAEAAASLLAICPFPSEALSPSQLLGLVR

AGVHRFFASLRLHGPPGVASACQLLTRLSQTSPAGLKAVLQLLVEGALHR

GNTELFGGQVDGDNETLSVVSASLASASLLDTNRRHTAAVPGPGGIWSVF

HAGVIGRGLKPPKFVQSRNQQEVIYNTQSLLSLLVHCCSAPGGTECGECW

GAPILSPEAAKAVAVTLVESVCPDAAGAELAWPPEEHARATVERDLRIGR

RFREQPLLFELLKLVAAAPPALCYCSVLLRGLLAALLGHWEASRHPDTTH

SPWHLEASCTLVAVMAEGSLLPPALGNMHEVFSQLAPFEVRLLLLSVWGF

LREHGPLPQKFIFQSERGRFIRDFSREGGGEGGPHLAVLHSVLHRNIDRL

GLFSGRFQAPSPSTLLRQGT

EXAMPLE 7

A Variant of the Human BFLP1698 Polypeptide Sequence Shown in Table 2

A polypeptide sequence varying by one amino acid from the BFLP1698 amino acid sequence presented in Table 2 is shown below. For the sequence shown, the T at position 556 of the BFLP1698 sequence shown in Table 2 has been replaced by a Y, which is shown in bold font.

(SEQ ID NO: 8)
MALVPGRSKEDGLWTRNSPGSSQHPESPRLPNPLWDRGKIGK

VEGHQHIQDFSQKSHLPSIVVESSEVNEESGDLHLPHEELLLLTDGEEED

AEAFFQDQSEEPGAARPHHQARQVEHSTQRGHLEIRELKKKLFKRRRVLN

RERRLRHRVVGAVIDQGLITRHHLKKRAAQELSQEIKAFLTGVDPILGHQ

LSAREHARCGLLLLRSLPPARAAVLDHLRGVFDESVRAHLAALDETPVAG

PPHLRPPPPSHVPAGGPGLEDVVQEVQQVLSEFIRANPKAWAPVISAWSI

DLMGQLSSTYSGQHQRVPHATGALNELLQLWMGCRATRTLMDIYVQCLSA

LIGSCPDACVDALLDTSVQHSPHFDWVVAHIGSSFPGTIISRVLSCGLKD

FCVHGGAGGGAGSSGGSSSQTPSTDPFPGSPAIPAEKRVPKIASVVGILG

HLASRHGDSIRRELLRMFHDSLAGGSGGRSGDPSLQATVPFLLQLAVMSP

ALLGTVSGELVDCLKPPAVLSQLQQHLQGFPREELDNMLNLAVHLVSQAS

GAGAYRLLQFLVDYAMPASVITTQGLAVPDTVREACDRLIQLLLLHLQKL

VHHRGGSPGEGVLGPPPPPRLVPFLDALKNHVGELCGETLRLERKRFLWQ

HQLLGLLSVYTRPSCGPEALGHLLSRARSPEELSLATQLYAGLVVSLSGL

LPLAFRSCLARVHAGTLQPPFTARFLRNLALLVGWEQQGGEGPAALGAHF

GESASAHLSDLAPLLLHPEEEVAEAAASLLAICPFPSEALSPSQLLGLVR

AGVHRFFASLRLHGPPGVASACQLLTRLSQTSPAGLKAVLQLLVEGALHR

GNTELFGGQVDGDNETLSVVSASLASASLLDTNRRHTAAVPGPGGIWSVF

HAGVIGRGLKPPKFVQSRNQQEVIYNTQSLLSLLVHCCSAPGGTECGECW

GAPILSPEAAKAVAVTLVESVCPDAAGAELAWPPEEHARATVERDLRIGR

RFREQPLLFELLKLVAAAPPALCYCSVLLRGLLAALLGHWEASRHPDTTH

```
SPWHLEASCTLVAVMAEGSLLPPALGNMHEVFSQLAPFEVRLLLLSVWGF
LREHGPLPQKFIFQSERGRFIRDFSREGGGEGGPHLAVLHSVLHRNIDRL
GLFSGRFQAPSPSTLLRQGT
```

EXAMPLE 8

A Variant of the Human BFLP1698 Polypeptide Sequence Shown in Table 2

A polypeptide sequence varying by one amino acid from the BFLP1698 amino acid sequence presented in Table 2 is shown below. For the sequence shown, the G at position 663 of the BFLP1698 sequence shown in Table 2 has been replaced by a P, which is shown in bold font.

```
                                            (SEQ ID NO: 9)
MALVPGRSKEDGLWTRNSPGSSQHPESPRLPNPLWDRGKIGK
VEGHQHIQDFSQKSHLPSIVVESSEVNEESGDLHLPHEELLLLTDGEEED
AEAFFQDQSEEPGAARPHHQARQVEHSTQRGHLEIRELKKKLFKRRRVLN
RERRLRHRVVGAVIDQGLITRHHLKKRAAQELSQEIKAFLTGVDPILGHQ
LSAREHARCGLLLLRSLPPARAAVLDHLRGVFDESVRAHLAALDETPVAG
PPHLRPPPPSHVPAGGPGLEDVVQEVQQVLSEFIRANPKAWAPVISAWSI
DLMGQLSSTYSGQHQRVPHATGALNELLQLWMGCRATRTLMDIYVQCLSA
LIGSCPDACVDALLDTSVQHSPHFDWVVAHIGSSFPGTIISRVLSCGLKD
FCVHGGAGGGAGSSGGSSSQTPSTDPFPGSPAIPAEKRVPKIASVVGILG
HLASRHGDSIRRELLRMFHDSLAGGSGGRSGDPSLQATVPFLLQLAVMSP
ALLGTVSGELVDCLKPPAVLSQLQQHLQGFPREELDNMLNLAVHLVSQAS
GAGAYRLLQFLVDTAMPASVITTQGLAVPDTVREACDRLIQLLLLHLQKL
VHHRGGSPGEGVLGPPPPPRLVPFLDALKNHVGELCGETLRLERKRFLWQ
HQLLGLLSVYTRPSCGPEALPHLLSRARSPEELSLATQLYAGLVVSLSGL
LPLAFRSCLARVHAGTLQPPFTARFLRNLALLVGWEQQGEGPAALGAHF
GESASAHLSDLAPLLLHPEEEVAEAAASLLAICPFPSEALSPSQLLGLVR
AGVHRFFASLRLHGPPGVASACQLLTRLSQTSPAGLKAVLQLLVEGALHR
GNTELFGGQVDGDNETLSVVSASLASASLLDTNRRHTAAVPGPGGIWSVF
HAGVIGRGLKPPKFVQSRNQQEVIYNTQSLLSLLVHCCSAPGGTECGECW
GAPILSPEAAKAVAVTLVESVCPDAAGAELAWPPEEHARATVERDLRIGR
RFREQPLLFELLKLVAAAPPALCYCSVLLRGLLAALLGHWEASRHPDTTH
SPWHLEASCTLVAVMAEGSLLPPALGNMHEVFSQLAPFEVRLLLLSVWGF
LREHGPLPQKFIFQSERGRFIRDFSREGGGEGGPHLAVLHSVLHRNIDRL
GLFSGRFQAPSPSTLLRQGT
```

EXAMPLE 9

A Variant of the Human BFLP1698 Polypeptide Sequence Shown in Table 2

A polypeptide sequence varying by one amino acid from the BFLP1698 amino acid sequence presented in Table 2 is shown below. For the sequence shown, the E at position 733 of the BFLP1698 sequence shown in Table 2 has been replaced by a D, which is shown in bold font.

```
                                            (SEQ ID NO: 10)
MALVPGRSKEDGLWTRNSPGSSQHPESPRLPNPLWDRGKIGK
VEGHQHIQDFSQKSHLPSIVVESSEVNEESGDLHLPHEELLLLTDGEEED
AEAFFQDQSEEPGAARPHHQARQVEHSTQRGHLEIRELKKKLFKRRRVLN
RERRLRHRVVGAVIDQGLITRHHLKKRAAQELSQEIKAFLTGVDPILGHQ
LSAREHARCGLLLLRSLPPARAAVLDHLRGVFDESVRAHLAALDETPVAG
PPHLRPPPPSHVPAGGPGLEDVVQEVQQVLSEFIRANPKAWAPVISAWSI
DLMGQLSSTYSGQHQRVPHATGALNELLQLWMGCRATRTLMDIYVQCLSA
LIGSCPDACVDALLDTSVQHSPHFDWVVAHIGSSFPGTIISRVLSCGLKD
FCVHGGAGGGAGSSGGSSSQTPSTDPFPGSPAIPAEKRVPKIASVVGILG
HLASRHGDSIRRELLRMFHDSLAGGSGGRSGDPSLQATVPFLLQLAVMSP
ALLGTVSGELVDCLKPPAVLSQLQQHLQGFPREELDNMLNLAVHLVSQAS
GAGAYRLLQFLVDTAMPASVITTQGLAVPDTVREACDRLIQLLLLHLQKL
VHHRGGSPGEGVLGPPPPPRLVPFLDALKNHVGELCGETLRLERKRFLWQ
HQLLGLLSVYTRPSCGPEALGHLLSRARSPEELSLATQLYAGLVVSLSGL
LPLAFRSCLARVHAGTLQPPFTARFLRNLALLVGWEQQGGDGPAALGAHF
GESASAHLSDLAPLLLHPEEEVAEAAASLLAICPFPSEALSPSQLLGLVR
AGVHRFFASLRLHGPPGVASACQLLTRLSQTSPAGLKAVLQLLVEGALHR
GNTELFGGQVDGDNETLSVVSASLASASLLDTNRRHTAAVPGPGGIWSVF
HAGVIGRGLKPPKFVQSRNQQEVIYNTQSLLSLLVHCCSAPGGTECGECW
GAPILSPEAAKAVAVTLVESVCPDAAGAELAWPPEEHARATVERDLRIGR
RFREQPLLFELLKLVAAAPPALCYCSVLLRGLLAALLGHWEASRHPDTTH
SPWHLEASCTLVAVMAEGSLLPPALGNMHEVFSQLAPFEVRLLLLSVWGF
LREHGPLPQKFIFQSERGRFIRDFSREGGGEGGPHLAVLHSVLHRNIDRL
GLFSGRFQAPSPSTLLRQGT
```

EXAMPLE 10

A Variant of the Human BFLP1698 Polypeptide Sequence Shown in Table 2

A polypeptide sequence varying by one amino acid from the BFLP1698 amino acid sequence presented in Table 2 is shown below. For the sequence shown, the T at position 858 of the BFLP1698 sequence shown in Table 2 has been replaced by a A, which is shown in bold font.

```
                                            (SEQ ID NO: 11)
MALVPGRSKEDGLWTRNSPGSSQHPESPRLPNPLWDRGKIGK
VEGHQHIQDFSQKSHLPSIVVESSEVNEESGDLHLPHEELLLLTDGEEED
AEAFFQDQSEEPGAARPHHQARQVEHSTQRGHLEIRELKKKLFKRRRVLN
RERRLRHRVVGAVIDQGLITRHHLKKRAAQELSQEIKAFLTGVDPILGHQ
LSAREHARCGLLLLRSLPPARAAVLDHLRGVFDESVRAHLAALDETPVAG
```

-continued
```
PPHLRPPPPPSHVPAGGPGLEDVVQEVQQVLSEFIRANPKAWAPVISAWSI

DLMGQLSSTYSGQHQRVPHATGALNELLQLWMGCRATRTLMDIYVQCLSA

LIGSCPDACVDALLDTSVQHSPHFDWVVAHIGSSFPGTIISRVLSCGLKD

FCVHGGAGGGAGSSGGSSSQTPSTDPFPGSPAIPAEKRVPKIASVVGILG

HLASRHGDSIRRELLRMFHDSLAGGSGGRSGDPSLQATVPFLLQLAVMSP

ALLGTVSGELVDCLKPPAVLSQLQQHLQGFPREELDNMLNLAVHLVSQAS

GAGAYRLLQFLVDTAMPASVITTQGLAVPDTVREACDRLIQLLLLHLQKL

VHHRGGSPGEGVLGPPPPPRLVPFLDALKNHVGELCGETLRLERKRFLWQ

HQLLGLLSVYTRPSCGPEALGHLLSRARSPEELSLATQLYAGLVVSLSGL

LPLAFRSCLARVHAGTLQPPFTARFLRNLALLVGWEQQGGEGPAALGAHF

GESASAHLSDLAPLLLHPEEEVAEAAASLLAICPFPSEALSPSQLLGLVR

AGVHRFFASLRLHGPPGVASACQLLTRLSQTSPAGLKAVLQLLVEGALHR

GNTELFGGQVDGDNEALSVVSASLASASLLDTNRRHTAAVPGPGGIWSVF

HAGVIGRGLKPPKFVQSRNQQEVIYNTQSLLSLLVHCCSAPGGTECGECW

GAPILSPEAAKAVAVTLVESVCPDAAGAELAWPPEEHARATVERDLRIGR

RFREQPLLFELLKLVAAAPPALCYCSVLLRGLLAALLGHWEASRHPDTTH

SPWHLEASCTLVAVMAEGSLLPPALGNMHEVFSQLAPFEVRLLLLSVWGF

LREHGPLPQKFIFQSERGRFIRDFSREGGGEGGPHLAVLHSVLHRNIDRL

GLFSGRFQAPSPSTLLRQGT
```

EXAMPLE 11

A Variant of the Human BFLP1698 Polypeptide Sequence Shown in Table 2

A polypeptide sequence varying by one amino acid from the BFLP1698 amino acid sequence presented in Table 2 is shown below. For the sequence shown, the W at position 974 of the BFLP1698 sequence shown in Table 2 has been replaced by a H, which is shown in bold font.

```
                                          (SEQ ID NO:12)
MALVPGRSKEDGLWTRNSPGSSQHPESPRLPNPLWDRGKIGKVEGHQHIQ

DFSQKSHLPSIVVESSEVNEESGDLHLPHEELLLLTDGEEEDAEAFFQDQ

SEEPGAARPHHQARQVEHSTQRGHLEIRELKKKLFKRRRVLNRERRLRHR

VVGAVIDQGLITRHHLKKRAAQELSQEIKAFLTGVDPILGHQLSAREHAR

CGLLLLRSLPPARAAVLDHLRGVFDESVRAHLAALDETPVAGPPHLRPPP

PSHVPAGGPGLEDVVQEVQQVLSEFIRANPKAWAPVISAWSIDLMGQLSS

TYSGQHQRVPHATGALNELLQLWMGCRATRTLMDIYVQCLSALIGSCPDA

CVDALLDTSVQHSPHFDWVVAHIGSSFPGTIISRVLSCGLKDFCVHGGAG

GGAGSSGGSSSQTPSTDPFPGSPAIPAEKRVPKIASVVGILGHLASRHGD

SIRRELLRMFHDSLAGGSGGRSGDPSLQATVPFLLQLAVMSPALLGTVSG

ELVDCLKPPAVLSQLQQHLQGFPREELDNMLNLAVHLVSQASGAGAYRLL

QFLVDTAMPASVITTQGLAVPDTVREACDRLIQLLLLHLQKLVHHRGGSP

GEGVLGPPPPPRLVPFLDALKNHVGELCGETLRLERKRFLWQHQLLGLLS

VYTRPSCGPEALGHLLSRARSPEELSLATQLYAGLVVSLSGLLPLAFRSC

LARVHAGTLQPPFTARFLRNLALLVGWEQQGGEGPAALGAHFGESASAHL

SDLAPLLLHPEEEVAEAAASLLAICPFPSEALSPSQLLGLVRAGVHRFFA

SLRLHGPPGVASACQLLTRLSQTSPAGLKAVLQLLVEGALHRGNTELFGG

QVDGDNETLSVVSASLASASLLDTNRRHTAAVPGPGGIWSVFHAGVIGRG

LKPPKFVQSRNQQEVIYNTQSLLSLLVHCCSAPGGTECGECWGAPILSPE

AAKAVAVTLVESVCPDAAGAELAHPPEEHARATVERDLRIGRRFREQPLL

FELLKLVAAAPPALCYCSVLLRGLLAALLGHWEASRHPDTTHSPWHLEAS

CTLVAVMAEGSLLPPALGNMHEVFSQLAPFEVRLLLLSVWGFLREHGPLP

QKFIFQSERGRFIRDFSREGGGEGGPHLAVLHSVLHRNIDRLGLFSGRFQ

APSPSTLLRQGT
```

EXAMPLE 12

A Variant of the Human BFLP1698 Polypeptide Sequence Shown in Table 2

A polypeptide sequence varying by one amino acid from the BFLP1698 amino acid sequence presented in Table 2 is shown below. For the sequence shown, the P at position 1038 of the BFLP1698 sequence shown in Table 2 has been replaced by a T, which is shown in bold font.

```
                                          (SEQ ID NO:13)
MALVPGRSKEDGLWTRNSPGSSQHPESPRLPNPLWDRGKIGKVEGHQHIQ

DFSQKSHLPSIVVESSEVNEESGDLHLPHEELLLLTDGEEEDAEAFFQDQ

SEEPGAARPHHQARQVEHSTQRGHLEIRELKKKLFKRRRVLNRERRLRHR

VVGAVIDQGLITRHHLKKRAAQELSQEIKAFLTGVDPILGHQLSAREHAR

CGLLLLRSLPPARAAVLDHLRGVFDESVRAHLAALDETPVAGPPHLRPPP

PSHVPAGGPGLEDVVQEVQQVLSEFIRANPKAWAPVISAWSIDLMGQLSS

TYSGQHQRVPHATGALNELLQLWMGCRATRTLMDIYVQCLSALIGSCPDA

CVDALLDTSVQHSPHFDWVVAHIGSSFPGTIISRVLSCGLKDFCVHGGAG

GGAGSSGGSSSQTPSTDPFPGSPAIPAEKRVPKIASVVGILGHLASRHGD

SIRRELLRMFHDSLAGGSGGRSGDPSLQATVPFLLQLAVMSPALLGTVSG

ELVDCLKPPAVLSQLQQHLQGFPREELDNMLNLAVHLVSQASGAGAYRLL

QFLVDTAMPASVITTQGLAVPDTVREACDRLIQLLLLHLQKLVHHRGGSP

GEGVLGPPPPPRLVPFLDALKNHVGELCGETLRLERKRFLWQHQLLGLLS

VYTRPSCGPEALGHLLSRARSPEELSLATQLYAGLVVSLSGLLPLAFRSC

LARVHAGTLQPPFTARFLRNLALLVGWEQQGGEGPAALGAHFGESASAHL

SDLAPLLLHPEEEVAEAAASLLAICPFPSEALSPSQLLGLVRAGVHRFFA

SLRLHGPPGVASACQLLTRLSQTSPAGLKAVLQLLVEGALHRGNTELFGG

QVDGDNETLSVVSASLASASLLDTNRRHTAAVPGPGGIWSVFHAGVIGRG

LKPPKFVQSRNQQEVIYNTQSLLSLLVHCCSAPGGTECGECWGAPILSPE

AAKAVAVTLVESVCPDAAGAELAWPPEEHARATVERDLRIGRRFREQPLL
```

-continued
FELLKLVAAAPPALCYCSVLLRGLLAALLGHWEASRHTDTTHSPWHLEAS

CTLVAVMAEGSLLPPALGNMHEVFSQLAPFEVRLLLLSVWGFLREHGPLP

QKFIFQSERGRFIRDFSREGGGEGGPHLAVLHSVLHRNIDRLGLFSGRFQ

APSPSTLLRQGT

EXAMPLE 13

A Variant of the Human BFLP1698 Polypeptide Sequence Shown in Table 2

A polypeptide sequence varying by one amino acid from the BFLP1698 amino acid sequence presented in Table 2 is shown below. For the sequence shown, the I at position 1139 of the BFLP1698 sequence shown in Table 2 has been replaced by a L, which is shown in bold font.

(SEQ ID NO: 14)
MALVPGRSKEDGLWTRNSPGSSQHPESPRLPNPLWDRGKIGKVEGHQHIQ

DFSQKSHLPSIVVESSEVNEESGDLHLPHEELLLLTDGEEEDAEAFFQDQ

SEEPGAARPHHQARQVEHSTQRGHLEIRELKKKLFKRRRVLNRERRLRHR

WGAVIDQGLITRHHLKKRAAQELSQEIKAFLTGVDPILGHQLSAREHARC

GLLLLRSLPPARAAVLDHLRGVFDESVRAHLAALDETPVAGPPHLRPPPP

SHVPAGGPGLEDVVQEVQQVLSEFIRANPKAWAPVISAWSIDLMGQLSST

YSGQHQRVPHATGALNELLQLWMGCRATRTLMDIYVQCLSALIGSCPDAC

VDALLDTSVQHSPHFDWVVAHIGSSFPGTIISRVLSCGLKDFCVHGGAGG

-continued
GAGSSGGSSSQTPSTDPFPGSPAIPAEKRVPKIASVVGILGHLASRHGDS

IRRELLRMFHDSLAGGSGGRSGDPSLQATVPFLLQLAVMSPALLGTVSGE

LVDCLKPPAVLSQLQQHLQGFPREELDNMLNLAVHLVSQASGAGAYRLLQ

FLVDTAMPASVITTQGLAVPDTVREACDRLIQLLLLHLQKLVHHRGGSPG

EGVLGPPPPPRLVPFLDALKNHVGELCGETLRLERKRFLWQHQLLGLLSV

YTRPSCGPEALGHLLSRARSPEELSLATQLYAGLVVSLSGLLPLAFRSCL

ARVHAGTLQPPFTARFLRNLALLVGWEQQGGEGPAALGAHFGESASAHLS

DLAPLLLHPEEEVAEAAASLLAICPFPSEALSPSQLLGLVRAGVHRFFAS

LRLHGPPGVASACQLLTRLSQTSPAGLKAVLQLLVEGALHRGNTELFGGQ

VDGDNETLSVVSASLASASLLDTNRRHTAAVPGPGGIWSVFHAGVIGRGL

KPPKFVQSRNQQEVIYNTQSLLSLLVHCCSAPGGTECGECWGAPILSPEA

AKAVAVTLVESVCPDAAGAELAWPPEEHARATVERDLRIGRRFREQPLLF

ELLKLVAAAPPALCYCSVLLRGLLAALLGHWEASRHTDTTHSPWHLEASC

TLVAVMAEGSLLPPALGNMHEVFSQLAPFEVRLLLLSVWGFLREHGPLPQ

KFIFQSERGRFIRDFSREGGGEGGPHLAVLHSVLHRNLDRLGLFSGRFQA

PSPSTLLRQGT

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule encoding a polypeptide comprising an amino acid sequence at least 95% identical to the amino acid sequence of SEQ ID NO:2.

2. The isolated nucleic acid molecule of claim 1, wherein said nucleic acid molecule encodes a polypeptide at least 98% identical to the amino acid sequence of SEQ ID NO:2.

3. The nucleic acid molecule of claim 1, wherein said molecule hybridizes under stringent conditions to a nucleic acid sequence complementary to a nucleic acid molecule comprising nucleotides 1-3486 of SEQ ID NO: 1.

4. The isolated nucleic acid molecule of claim 1 wherein said nucleic acid molecule encodes a polypeptide comprising the amino acid sequence of SEQ ID NO:2.

5. The isolated nucleic acid molecule of claim 1, wherein said nucleic acid molecule comprises nucleotides 1-3486 of SEQ ID NO: 1.

6. A vector comprising the nucleic acid molecule of claim 1.

7. A cell including the vector of claim 6.

8. A method of producing a BFLP1698 polypeptide, said method comprising culturing a cell including the nucleic acid molecule of claim 1 under conditions allowing for expression of a BFLP1698 polypeptide encoded by said nucleic acid molecule.

9. A method of detecting the presence of a BFLP1698 nucleic acid molecule in a biological sample, the method comprising:
   contacting the sample with a nucleic acid probe that binds specifically to a BFLP1698 nucleic acid; and
   identifying the bound probe, if present,
   thereby detecting the presence of BFLP 1698 nucleic acid molecule in said sample.

* * * * *

SEQUENCE LISTING

```
<160> NUMBER OF SEQ ID NOS: 21

<210> SEQ ID NO 1
<211> LENGTH: 3652
<212> TYPE: DNA
<213> ORGANISM: Homo sapiens

<400> SEQUENCE: 1
atggcccttg tgccagggag aagcaaggag gatgggcttt ggactagaaa tagcccaggc      60
tcctcccagc atccagaaag tcccaggctg cccaaccctc tctgggacag aggaaaaatt     120
ggcaaggttg aaggtcacca gcacattcag gatttctctc aaaagtccca tctgccgtct     180
attgtggtgg aatccagtga ggtgaatgaa gagagtgggg atctccattt gccccatgag     240
gagctgctgc tgctcactga tggtgaggaa gaggatgctg aggccttctt ccaagaccaa     300
agtgaagagc caggggcggc acgtccccat catcaggctc ggcaagtgga gcattcgacg     360
cagcgcggcc atctggagat tcgggagctg aagaagaagc tgttcaaacg ccggcgggtg     420
ttgaatcggg agcggcgtct gaggcaccgg gtggtcgggg ctgtgataga ccaagggctg     480
atcacgcggc accacctcaa gaagcgggct gctcaggagc tgtcccagga aatcaaggct     540
tttctgactg gcgtagaccc cattctgggc caccaactct cagcccggga acatgctcgc     600
tgtggtcttc tcctgctccg ttctttgcca cctgctcggg ctgctgtgct tgaccacttg     660
```

```
agaggtgtct tgatgagag tgtccgggcc cacctggctg ccctggatga aacccctgtg    720
gctggtccac ctcacctccg tccacctcca ccctctcatg tccctgctgg tggacctggt    780
ctagaggatg tggttcagga agtgcagcag gtgctgtctg agtttatccg ggccaaccca    840
aaggcctggg cacctgtgat tagtgcatgg tccattgacc tcatggggca actgagcagc    900
acgtactcag gccagcacca gcgtgttccc cacgctactg gcgctcttaa tgaactgcta    960
cagctgtgga tgggttgtag ggccacgcgt acattaatgg acatctatgt gcagtgcctc   1020
tcggctctca ttggtagctg cccagatgcg tgtgtggatg ccttgctgga tacctctgtt   1080
cagcattctc cacactttga ctgggttgtg gcacatattg gctcctcttt tcctggcacc   1140
atcatttccc gggttctctc ctgtggcctt aaggactttt gtgtccatgg tggggctgga   1200
ggtggagctg gcagtagtgg tggaagctct tctcagaccc cctctacaga ccccttccct   1260
ggatctcctg ccattcctgc ggagaaacgg gtgcccaaga ttgcctcagt tgtaggcatc   1320
ctaggtcacc tggcctcccg ccacggagat agcatccgac gggagctcct gcgaatgttc   1380
catgatagcc tggcaggggg atctggaggc cgcagtgggg accctcccct tcaggccacg   1440
gttccgttcc tactgcagct ggcagtcatg tcaccagctt gctgggcac  tgtctctgga   1500
gagcttgtgg attgcctcaa gccccagct  gtgctgagcc agctgcagca acaccttcaa   1560
ggattccccc gagaggagct ggacaacatg ttgaacctgg ctgtgcacct ggtgagccag   1620
gcctctgggg caggtgccta ccgcttgctg cagttcctgg tggacacagc tatgcctgct   1680
tcggtcatta ccacccaggg cctggctgtg ccagacaccg tgcgtgaggc ttgtgaccgg   1740
ctaatccagc tgctgctgct gcacctgcaa aaactggttc atcaccgggg agggtctcct   1800
ggggaagggg tgctaggccc gcccccacct ccccgcttgg tgccctttt  agatgcgctc   1860
aaaaaccatg ttggagagct gtgtggagag acgttacgat tggaacggaa gcgcttcctc   1920
tggcagcacc agctcttggg cctgctgtct gtctataccc ggcctagctg tggacctgag   1980
gccttgggcc atctgctgag ccgagcccga agccctgaag agttgagttt ggccacccag   2040
ttatatgcag ggctagtggt cagcctctct ggcctcctgc ccctggcttt ccgaagctgt   2100
ctggctcggg tgcatgcagg gacattacag cctcccttca cggcccggtt cctgcgcaac   2160
ttggcactgc tagtagggtg ggaacagcag ggtggcgagg gccctgcagc cctaggggcg   2220
cactttgggg aatctgcctc agcccatctg tctgacctgg ctcctctcct gctacatcct   2280
gaggaggaag tagctgaagc tgctgcctct ctcctggcca tttgtccctt tccttctgaa   2340
gccttatccc cctcccagct cctgggactg gtaagggctg gggtgcaccg cttctttgcc   2400
tctctgaggc tgcatggacc cccaggtgtg gcctcagcct gtcagcttct cacccgcctg   2460
tctcagacat ccccagctgg gctcaaggct gtcctgcagc tgctggttga aggagcctta   2520
catcgaggca acacagaact gttggtgggg caagtagatg gggacaatga gactctctca   2580
gttgtttcag cttctttggc ttctgcctcc ctgttggaca ctaaccggag gcacactgca   2640
gctgtgccag gtcctggagg gatttggtca gttttccatg ctggagtcat cggccgtggc   2700
ttaaagccac ccaagtttgt ccagtcacga aatcagcagg aagtgatcta taacacccag   2760
agcctcctca gcctcctggt tcactgctgc agtgccccag ggcactga   atgtgggaa    2820
tgctgggggg cacccatctt gagtccagag gcagccaaag cagtggcagt gaccttggtg   2880
gagagtgtgt gtcccgatgc agctggtgca gagctggcct ggccccccga ggaacacgcc   2940
cgggccaccg tggagcggga tctccgcatt ggccggcgct ccgcgaaaca gccctgctc    3000
```

-continued

```
tttgagctgt taaagctggt agcagctgca cccccagccc tgtgctactg ttccgtgctg   3060 cttcggggc tgctggccgc cctcttgggc cattgggaag cctctcgcca ccctgacacg   3120
acccactccc cctggcacct ggaggcatcc tgcaccttag tggctgtcat ggctgaggga   3180
agcctcctgc ctccggccct gggtaatatg catgaagtat ttagccaact ggcacctttc   3240
gaggtgcgtc tgctgctgct cagtgtctgg ggttttctcc gggagcatgg gcccttgcct   3300
cagaagttca tcttccaatc agagcggggt cgcttcattc gggacttctc cagggagggt   3360
ggaggtgagg gtggacccca tctggctgtg ctgcacagtg tcctccaccg caacatcgac   3420
cgcctaggtc ttttctctgg ccgtttccag gcaccttcac cgtccactct ccttcgacag   3480
gggacgtagc cttttcttgc tctggaagcc cagggaggtt gagcagtgag agagggaagg   3540
gactaacgtg ctccggaagg gtggaggttt ctcttctaag tccttggtct aaagagcgct   3600 gtcactttt tctctcccac tttttttttt ctaaataaaa tttgccaact tg             3652
```

<210> SEQ ID NO 2
<211> LENGTH: 1162
<212> TYPE: PRT
<213> ORGANISM: Homo sapiens

<400> SEQUENCE: 2

```
Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
            20                  25                  30

Pro Leu Trp Asp Arg Gly Lys Ile Gly Lys Val Glu Gly His Gln His
        35                  40                  45

Ile Gln Asp Phe Ser Gln Lys Ser His Leu Pro Ser Ile Val Val Glu
    50                  55                  60

Ser Ser Glu Val Asn Glu Glu Ser Gly Asp Leu His Leu Pro His Glu
65                  70                  75                  80

Glu Leu Leu Leu Leu Thr Asp Gly Glu Glu Glu Asp Ala Glu Ala Phe
                85                  90                  95

Phe Gln Asp Gln Ser Glu Glu Pro Gly Ala Ala Arg Pro His His Gln
            100                 105                 110

Ala Arg Gln Val Glu His Ser Thr Gln Arg Gly His Leu Glu Ile Arg
        115                 120                 125

Glu Leu Lys Lys Lys Leu Phe Lys Arg Arg Val Leu Asn Arg Glu
    130                 135                 140

Arg Arg Leu Arg His Arg Val Val Gly Ala Val Ile Asp Gln Gly Leu
145                 150                 155                 160

Ile Thr Arg His His Leu Lys Lys Arg Ala Ala Gln Glu Leu Ser Gln
                165                 170                 175

Glu Ile Lys Ala Phe Leu Thr Gly Val Asp Pro Ile Leu Gly His Gln
            180                 185                 190

Leu Ser Ala Arg Glu His Ala Arg Cys Gly Leu Leu Leu Arg Ser
        195                 200                 205

Leu Pro Pro Ala Arg Ala Ala Val Leu Asp His Leu Arg Gly Val Phe
    210                 215                 220

Asp Glu Ser Val Arg Ala His Leu Ala Ala Leu Asp Glu Thr Pro Val
225                 230                 235                 240

Ala Gly Pro Pro His Leu Arg Pro Pro Pro Ser His Val Pro Ala
                245                 250                 255

Gly Gly Pro Gly Leu Glu Asp Val Val Gln Glu Val Gln Gln Val Leu
```

-continued

```
                260                 265                 270
Ser Glu Phe Ile Arg Ala Asn Pro Lys Ala Trp Ala Pro Val Ile Ser
            275                 280                 285

Ala Trp Ser Ile Asp Leu Met Gly Gln Leu Ser Ser Thr Tyr Ser Gly
        290                 295                 300

Gln His Gln Arg Val Pro His Ala Thr Gly Ala Leu Asn Glu Leu Leu
305                 310                 315                 320

Gln Leu Trp Met Gly Cys Arg Ala Thr Arg Thr Leu Met Asp Ile Tyr
                325                 330                 335

Val Gln Cys Leu Ser Ala Leu Ile Gly Ser Cys Pro Asp Ala Cys Val
            340                 345                 350

Asp Ala Leu Leu Asp Thr Ser Val Gln His Ser Pro His Phe Asp Trp
        355                 360                 365

Val Val Ala His Ile Gly Ser Ser Phe Pro Gly Thr Ile Ile Ser Arg
    370                 375                 380

Val Leu Ser Cys Gly Leu Lys Asp Phe Cys Val His Gly Gly Ala Gly
385                 390                 395                 400

Gly Gly Ala Gly Ser Ser Gly Gly Ser Ser Ser Gln Thr Pro Ser Thr
                405                 410                 415

Asp Pro Phe Pro Gly Ser Pro Ala Ile Pro Ala Glu Lys Arg Val Pro
            420                 425                 430

Lys Ile Ala Ser Val Val Gly Ile Leu Gly His Leu Ala Ser Arg His
        435                 440                 445

Gly Asp Ser Ile Arg Arg Glu Leu Leu Arg Met Phe His Asp Ser Leu
450                 455                 460

Ala Gly Gly Ser Gly Gly Arg Ser Gly Asp Pro Ser Leu Gln Ala Thr
465                 470                 475                 480

Val Pro Phe Leu Leu Gln Leu Ala Val Met Ser Pro Ala Leu Leu Gly
            485                 490                 495

Thr Val Ser Gly Glu Leu Val Asp Cys Leu Lys Pro Pro Ala Val Leu
        500                 505                 510

Ser Gln Leu Gln Gln His Leu Gln Gly Phe Pro Arg Glu Glu Leu Asp
    515                 520                 525

Asn Met Leu Asn Leu Ala Val His Leu Val Ser Gln Ala Ser Gly Ala
530                 535                 540

Gly Ala Tyr Arg Leu Leu Gln Phe Leu Val Asp Thr Ala Met Pro Ala
545                 550                 555                 560

Ser Val Ile Thr Thr Gln Gly Leu Ala Val Pro Asp Thr Val Arg Glu
                565                 570                 575

Ala Cys Asp Arg Leu Ile Gln Leu Leu Leu His Leu Gln Lys Leu
            580                 585                 590

Val His His Arg Gly Gly Ser Pro Gly Glu Gly Val Leu Gly Pro Pro
        595                 600                 605

Pro Pro Pro Arg Leu Val Pro Phe Leu Asp Ala Leu Lys Asn His Val
    610                 615                 620

Gly Glu Leu Cys Gly Glu Thr Leu Arg Leu Glu Arg Lys Arg Phe Leu
625                 630                 635                 640

Trp Gln His Gln Leu Leu Gly Leu Leu Ser Val Tyr Thr Arg Pro Ser
                645                 650                 655

Cys Gly Pro Glu Ala Leu Gly His Leu Leu Ser Arg Ala Arg Ser Pro
            660                 665                 670

Glu Glu Leu Ser Leu Ala Thr Gln Leu Tyr Ala Gly Leu Val Val Ser
        675                 680                 685
```

```
Leu Ser Gly Leu Leu Pro Leu Ala Phe Arg Ser Cys Leu Ala Arg Val
    690             695                 700

His Ala Gly Thr Leu Gln Pro Pro Phe Thr Ala Arg Phe Leu Arg Asn
705             710                 715                 720

Leu Ala Leu Leu Val Gly Trp Glu Gln Gln Gly Gly Glu Gly Pro Ala
            725                 730                 735

Ala Leu Gly Ala His Phe Gly Glu Ser Ala Ser Ala His Leu Ser Asp
            740                 745                 750

Leu Ala Pro Leu Leu Leu His Pro Glu Glu Val Ala Glu Ala Ala
        755                 760                 765

Ala Ser Leu Leu Ala Ile Cys Pro Phe Pro Ser Glu Ala Leu Ser Pro
    770                 775                 780

Ser Gln Leu Leu Gly Leu Val Arg Ala Gly Val His Arg Phe Phe Ala
785             790                 795                 800

Ser Leu Arg Leu His Gly Pro Pro Gly Val Ala Ser Ala Cys Gln Leu
                805                 810                 815

Leu Thr Arg Leu Ser Gln Thr Ser Pro Ala Gly Leu Lys Ala Val Leu
            820                 825                 830

Gln Leu Leu Val Glu Gly Ala Leu His Arg Gly Asn Thr Glu Leu Phe
        835                 840                 845

Gly Gly Gln Val Asp Gly Asp Asn Glu Thr Leu Ser Val Val Ser Ala
    850                 855                 860

Ser Leu Ala Ser Ala Ser Leu Leu Asp Thr Asn Arg Arg His Thr Ala
865             870                 875                 880

Ala Val Pro Gly Pro Gly Gly Ile Trp Ser Val Phe His Ala Gly Val
                885                 890                 895

Ile Gly Arg Gly Leu Lys Pro Pro Lys Phe Val Gln Ser Arg Asn Gln
            900                 905                 910

Gln Glu Val Ile Tyr Asn Thr Gln Ser Leu Leu Ser Leu Leu Val His
        915                 920                 925

Cys Cys Ser Ala Pro Gly Gly Thr Glu Cys Gly Glu Cys Trp Gly Ala
930             935                 940

Pro Ile Leu Ser Pro Glu Ala Ala Lys Ala Val Ala Val Thr Leu Val
945             950                 955                 960

Glu Ser Val Cys Pro Asp Ala Ala Gly Ala Glu Leu Ala Trp Pro Pro
            965                 970                 975

Glu Glu His Ala Arg Ala Thr Val Glu Arg Asp Leu Arg Ile Gly Arg
            980                 985                 990

Arg Phe Arg Glu Gln Pro Leu Leu Phe Glu Leu Leu Lys Leu Val Ala
    995                 1000                1005

Ala Ala Pro Pro Ala Leu Cys Tyr Cys Ser Val Leu Leu Arg Gly
    1010                1015                1020

Leu Leu Ala Ala Leu Leu Gly His Trp Glu Ala Ser Arg His Pro
    1025                1030                1035

Asp Thr Thr His Ser Pro Trp His Leu Glu Ala Ser Cys Thr Leu
    1040                1045                1050

Val Ala Val Met Ala Glu Gly Ser Leu Leu Pro Pro Ala Leu Gly
    1055                1060                1065

Asn Met His Glu Val Phe Ser Gln Leu Ala Pro Phe Glu Val Arg
    1070                1075                1080

Leu Leu Leu Leu Ser Val Trp Gly Phe Leu Arg Glu His Gly Pro
    1085                1090                1095
```

```
Leu Pro Gln Lys Phe Ile Phe Gln Ser Glu Arg Gly Arg Phe Ile
    1100                1105                1110

Arg Asp Phe Ser Arg Glu Gly Gly Glu Gly Gly Pro His Leu
    1115                1120                1125

Ala Val Leu His Ser Val Leu His Arg Asn Ile Asp Arg Leu Gly
    1130                1135                1140

Leu Phe Ser Gly Arg Phe Gln Ala Pro Ser Pro Ser Thr Leu Leu
    1145                1150                1155

Arg Gln Gly Thr
    1160

<210> SEQ ID NO 3
<211> LENGTH: 1162
<212> TYPE: PRT
<213> ORGANISM: Artificial
<220> FEATURE:
<223> OTHER INFORMATION: A variant of the human BFLP1698 polypeptide

<400> SEQUENCE: 3

Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
                20                  25                  30

Pro Leu Trp Asp Arg Gly Lys Ile Gly Lys Val Glu Gly His Gln His
            35                  40                  45

Ile Gln Asp Phe Ser Gln Lys Ser His Leu Pro Ser Ile Val Val Glu
        50                  55                  60

Ser Ser Glu Val Asn Glu Glu Ser Gly Asp Leu His Leu Pro His Glu
65                  70                  75                  80

Glu Leu Leu Leu Leu Thr Asp Gly Glu Glu Glu Asp Ala Glu Ala Phe
                85                  90                  95

Leu Gln Asp Gln Ser Glu Glu Pro Gly Ala Ala Arg Pro His His Gln
            100                 105                 110

Ala Arg Gln Val Glu His Ser Thr Gln Arg Gly His Leu Glu Ile Arg
        115                 120                 125

Glu Leu Lys Lys Lys Leu Phe Lys Arg Arg Val Leu Asn Arg Glu
    130                 135                 140

Arg Arg Leu Arg His Arg Val Val Gly Ala Val Ile Asp Gln Gly Leu
145                 150                 155                 160

Ile Thr Arg His His Leu Lys Lys Arg Ala Ala Gln Glu Leu Ser Gln
                165                 170                 175

Glu Ile Lys Ala Phe Leu Thr Gly Val Asp Pro Ile Leu Gly His Gln
            180                 185                 190

Leu Ser Ala Arg Glu His Ala Arg Cys Gly Leu Leu Leu Leu Arg Ser
        195                 200                 205

Leu Pro Pro Ala Arg Ala Ala Val Leu Asp His Leu Arg Gly Val Phe
    210                 215                 220

Asp Glu Ser Val Arg Ala His Leu Ala Ala Leu Asp Glu Thr Pro Val
225                 230                 235                 240

Ala Gly Pro Pro His Leu Arg Pro Pro Pro Ser His Val Pro Ala
                245                 250                 255

Gly Gly Pro Gly Leu Glu Asp Val Gln Glu Val Gln Gln Val Leu
            260                 265                 270

Ser Glu Phe Ile Arg Ala Asn Pro Lys Ala Trp Ala Pro Val Ile Ser
        275                 280                 285
```

-continued

```
Ala Trp Ser Ile Asp Leu Met Gly Gln Leu Ser Ser Thr Tyr Ser Gly
    290                 295                 300
Gln His Gln Arg Val Pro His Ala Thr Gly Ala Leu Asn Glu Leu Leu
305                 310                 315                 320
Gln Leu Trp Met Gly Cys Arg Ala Thr Arg Thr Leu Met Asp Ile Tyr
                325                 330                 335
Val Gln Cys Leu Ser Ala Leu Ile Gly Ser Cys Pro Asp Ala Cys Val
            340                 345                 350
Asp Ala Leu Leu Asp Thr Ser Val Gln His Ser Pro His Phe Asp Trp
        355                 360                 365
Val Val Ala His Ile Gly Ser Ser Phe Pro Gly Thr Ile Ile Ser Arg
    370                 375                 380
Val Leu Ser Cys Gly Leu Lys Asp Phe Cys Val His Gly Gly Ala Gly
385                 390                 395                 400
Gly Gly Ala Gly Ser Ser Gly Gly Ser Ser Gln Thr Pro Ser Thr
                405                 410                 415
Asp Pro Phe Pro Gly Ser Pro Ala Ile Pro Ala Glu Lys Arg Val Pro
                420                 425                 430
Lys Ile Ala Ser Val Val Gly Ile Leu Gly His Leu Ala Ser Arg His
            435                 440                 445
Gly Asp Ser Ile Arg Arg Glu Leu Leu Arg Met Phe His Asp Ser Leu
450                 455                 460
Ala Gly Gly Ser Gly Gly Arg Ser Gly Asp Pro Ser Leu Gln Ala Thr
465                 470                 475                 480
Val Pro Phe Leu Leu Gln Leu Ala Val Met Ser Pro Ala Leu Leu Gly
                485                 490                 495
Thr Val Ser Gly Glu Leu Val Asp Cys Leu Lys Pro Pro Ala Val Leu
            500                 505                 510
Ser Gln Leu Gln Gln His Leu Gln Gly Phe Pro Arg Glu Glu Leu Asp
        515                 520                 525
Asn Met Leu Asn Leu Ala Val His Leu Val Ser Gln Ala Ser Gly Ala
    530                 535                 540
Gly Ala Tyr Arg Leu Leu Gln Phe Leu Val Asp Thr Ala Met Pro Ala
545                 550                 555                 560
Ser Val Ile Thr Thr Gln Gly Leu Ala Val Pro Asp Thr Val Arg Glu
                565                 570                 575
Ala Cys Asp Arg Leu Ile Gln Leu Leu Leu His Leu Gln Lys Leu
            580                 585                 590
Val His His Arg Gly Gly Ser Pro Gly Glu Gly Val Leu Gly Pro Pro
        595                 600                 605
Pro Pro Pro Arg Leu Val Pro Phe Leu Asp Ala Leu Lys Asn His Val
    610                 615                 620
Gly Glu Leu Cys Gly Glu Thr Leu Arg Leu Glu Arg Lys Arg Phe Leu
625                 630                 635                 640
Trp Gln His Gln Leu Leu Gly Leu Leu Ser Val Tyr Thr Arg Pro Ser
                645                 650                 655
Cys Gly Pro Glu Ala Leu Gly His Leu Ser Arg Ala Arg Ser Pro
            660                 665                 670
Glu Glu Leu Ser Leu Ala Thr Gln Leu Tyr Ala Gly Leu Val Val Ser
        675                 680                 685
Leu Ser Gly Leu Leu Pro Leu Ala Phe Arg Ser Cys Leu Ala Arg Val
    690                 695                 700
His Ala Gly Thr Leu Gln Pro Pro Phe Thr Ala Arg Phe Leu Arg Asn
```

```
            705             710             715             720
Leu Ala Leu Leu Val Gly Trp Glu Gln Gln Gly Gly Glu Gly Pro Ala
                725             730             735
Ala Leu Gly Ala His Phe Gly Glu Ser Ala Ser Ala His Leu Ser Asp
            740             745             750
Leu Ala Pro Leu Leu His Pro Glu Glu Val Ala Glu Ala Ala
            755             760             765
Ala Ser Leu Leu Ala Ile Cys Pro Phe Pro Ser Glu Ala Leu Ser Pro
            770             775             780
Ser Gln Leu Leu Gly Leu Val Arg Ala Gly Val His Arg Phe Phe Ala
785             790             795             800
Ser Leu Arg Leu His Gly Pro Pro Gly Val Ala Ser Ala Cys Gln Leu
                805             810             815
Leu Thr Arg Leu Ser Gln Thr Ser Pro Ala Gly Leu Lys Ala Val Leu
                820             825             830
Gln Leu Leu Val Glu Gly Ala Leu His Arg Gly Asn Thr Glu Leu Phe
                835             840             845
Gly Gly Gln Val Asp Gly Asp Asn Glu Thr Leu Ser Val Val Ser Ala
                850             855             860
Ser Leu Ala Ser Ala Ser Leu Leu Asp Thr Asn Arg Arg His Thr Ala
865             870             875             880
Ala Val Pro Gly Pro Gly Gly Ile Trp Ser Val Phe His Ala Gly Val
                885             890             895
Ile Gly Arg Gly Leu Lys Pro Pro Lys Phe Val Gln Ser Arg Asn Gln
                900             905             910
Gln Glu Val Ile Tyr Asn Thr Gln Ser Leu Leu Ser Leu Val His
                915             920             925
Cys Cys Ser Ala Pro Gly Gly Thr Glu Cys Gly Glu Cys Trp Gly Ala
                930             935             940
Pro Ile Leu Ser Pro Glu Ala Ala Lys Ala Val Ala Val Thr Leu Val
945             950             955             960
Glu Ser Val Cys Pro Asp Ala Ala Gly Ala Glu Leu Ala Trp Pro Pro
                965             970             975
Glu Glu His Ala Arg Ala Thr Val Glu Arg Asp Leu Arg Ile Gly Arg
                980             985             990
Arg Phe Arg Glu Gln Pro Leu Leu Phe Glu Leu Leu Lys Leu Val Ala
                995             1000            1005
Ala Ala Pro Pro Ala Leu Cys Tyr Cys Ser Val Leu Leu Arg Gly
            1010            1015            1020
Leu Leu Ala Ala Leu Leu Gly His Trp Glu Ala Ser Arg His Pro
            1025            1030            1035
Asp Thr Thr His Ser Pro Trp His Leu Glu Ala Ser Cys Thr Leu
            1040            1045            1050
Val Ala Val Met Ala Glu Gly Ser Leu Leu Pro Ala Leu Gly
            1055            1060            1065
Asn Met His Glu Val Phe Ser Gln Leu Ala Pro Phe Glu Val Arg
            1070            1075            1080
Leu Leu Leu Leu Ser Val Trp Gly Phe Leu Arg Glu His Gly Pro
            1085            1090            1095
Leu Pro Gln Lys Phe Ile Phe Gln Ser Glu Arg Gly Arg Phe Ile
            1100            1105            1110
Arg Asp Phe Ser Arg Glu Gly Gly Gly Glu Gly Gly Pro His Leu
            1115            1120            1125
```

```
Ala Val Leu His Ser Val Leu His Arg Asn Ile Asp Arg Leu Gly
    1130                1135                1140

Leu Phe Ser Gly Arg Phe Gln Ala Pro Ser Pro Ser Thr Leu Leu
    1145                1150                1155

Arg Gln Gly Thr
    1160

<210> SEQ ID NO 4
<211> LENGTH: 1162
<212> TYPE: PRT
<213> ORGANISM: Artificial
<220> FEATURE:
<223> OTHER INFORMATION: A variant of the human BFLP1698 polypeptide

<400> SEQUENCE: 4

Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
            20                  25                  30

Pro Leu Trp Asp Arg Gly Lys Ile Gly Lys Val Glu Gly His Gln His
        35                  40                  45

Ile Gln Asp Phe Ser Gln Lys Ser His Leu Pro Ser Ile Val Val Glu
    50                  55                  60

Ser Ser Glu Val Asn Glu Glu Ser Gly Asp Leu His Leu Pro His Glu
65              70                  75                  80

Glu Leu Leu Leu Leu Thr Asp Gly Glu Glu Asp Ala Glu Ala Phe
            85                  90                  95

Phe Gln Asp Gln Ser Glu Glu Pro Gly Ala Ala Arg Pro His His Gln
            100                 105                 110

Ala Arg Gln Val Glu His Ser Thr Gln Arg Gly His Leu Glu Ile Arg
        115                 120                 125

Glu Leu Lys Lys Lys Leu Phe Lys Arg Arg Val Leu Asn Arg Glu
    130                 135                 140

Arg Arg Leu Arg His Arg Val Val Gly Ala Val Ile Asp Gln Gly Leu
145                 150                 155                 160

Ile Thr Arg His His Leu Lys Lys Arg Ala Ala Gln Glu Leu Ser Gln
            165                 170                 175

Glu Ile Lys Ala Phe Leu Thr Gly Val Asp Pro Ile Leu Gly His Asn
        180                 185                 190

Leu Ser Ala Arg Glu His Ala Arg Cys Gly Leu Leu Leu Arg Ser
    195                 200                 205

Leu Pro Pro Ala Arg Ala Ala Val Leu Asp His Leu Arg Gly Val Phe
    210                 215                 220

Asp Glu Ser Val Arg Ala His Leu Ala Ala Leu Asp Glu Thr Pro Val
225                 230                 235                 240

Ala Gly Pro Pro His Leu Arg Pro Pro Pro Ser His Val Pro Ala
            245                 250                 255

Gly Gly Pro Gly Leu Glu Asp Val Val Gln Glu Val Gln Gln Val Leu
            260                 265                 270

Ser Glu Phe Ile Arg Ala Asn Pro Lys Ala Trp Ala Pro Val Ile Ser
        275                 280                 285

Ala Trp Ser Ile Asp Leu Met Gly Gln Leu Ser Ser Thr Tyr Ser Gly
    290                 295                 300

Gln His Gln Arg Val Pro His Ala Thr Gly Ala Leu Asn Glu Leu Leu
305                 310                 315                 320
```

-continued

```
Gln Leu Trp Met Gly Cys Arg Ala Thr Arg Thr Leu Met Asp Ile Tyr
            325                 330                 335
Val Gln Cys Leu Ser Ala Leu Ile Gly Ser Cys Pro Asp Ala Cys Val
        340                 345                 350
Asp Ala Leu Leu Asp Thr Ser Val Gln His Ser Pro His Phe Asp Trp
    355                 360                 365
Val Val Ala His Ile Gly Ser Ser Phe Pro Gly Thr Ile Ile Ser Arg
370                 375                 380
Val Leu Ser Cys Gly Leu Lys Asp Phe Cys Val His Gly Gly Ala Gly
385                 390                 395                 400
Gly Gly Ala Gly Ser Ser Gly Gly Ser Ser Ser Gln Thr Pro Ser Thr
                405                 410                 415
Asp Pro Phe Pro Gly Ser Pro Ala Ile Pro Ala Glu Lys Arg Val Pro
            420                 425                 430
Lys Ile Ala Ser Val Val Gly Ile Leu Gly His Leu Ala Ser Arg His
        435                 440                 445
Gly Asp Ser Ile Arg Arg Glu Leu Leu Arg Met Phe His Asp Ser Leu
    450                 455                 460
Ala Gly Gly Ser Gly Gly Arg Ser Gly Asp Pro Ser Leu Gln Ala Thr
465                 470                 475                 480
Val Pro Phe Leu Leu Gln Leu Ala Val Met Ser Pro Ala Leu Leu Gly
                485                 490                 495
Thr Val Ser Gly Glu Leu Val Asp Cys Leu Lys Pro Pro Ala Val Leu
            500                 505                 510
Ser Gln Leu Gln Gln His Leu Gln Gly Phe Pro Arg Glu Glu Leu Asp
        515                 520                 525
Asn Met Leu Asn Leu Ala Val His Leu Val Ser Gln Ala Ser Gly Ala
    530                 535                 540
Gly Ala Tyr Arg Leu Leu Gln Phe Leu Val Asp Thr Ala Met Pro Ala
545                 550                 555                 560
Ser Val Ile Thr Thr Gln Gly Leu Ala Val Pro Asp Thr Val Arg Glu
                565                 570                 575
Ala Cys Asp Arg Leu Ile Gln Leu Leu Leu His Leu Gln Lys Leu
            580                 585                 590
Val His His Arg Gly Gly Ser Pro Gly Glu Gly Val Leu Gly Pro Pro
        595                 600                 605
Pro Pro Pro Arg Leu Val Pro Phe Leu Asp Ala Leu Lys Asn His Val
    610                 615                 620
Gly Glu Leu Cys Gly Glu Thr Leu Arg Leu Glu Arg Lys Arg Phe Leu
625                 630                 635                 640
Trp Gln His Gln Leu Leu Gly Leu Leu Ser Val Tyr Thr Arg Pro Ser
                645                 650                 655
Cys Gly Pro Glu Ala Leu Gly His Leu Leu Ser Arg Ala Arg Ser Pro
            660                 665                 670
Glu Glu Leu Ser Leu Ala Thr Gln Leu Tyr Ala Gly Leu Val Val Ser
        675                 680                 685
Leu Ser Gly Leu Leu Pro Leu Ala Phe Arg Ser Cys Leu Ala Arg Val
    690                 695                 700
His Ala Gly Thr Leu Gln Pro Pro Phe Thr Ala Arg Phe Leu Arg Asn
705                 710                 715                 720
Leu Ala Leu Leu Val Gly Trp Glu Gln Gln Gly Gly Glu Gly Pro Ala
                725                 730                 735
```

```
Ala Leu Gly Ala His Phe Gly Glu Ser Ala Ser Ala His Leu Ser Asp
            740                 745                 750

Leu Ala Pro Leu Leu His Pro Glu Glu Val Ala Glu Ala Ala
            755                 760                 765

Ala Ser Leu Leu Ala Ile Cys Pro Phe Pro Ser Glu Ala Leu Ser Pro
            770                 775                 780

Ser Gln Leu Leu Gly Leu Val Arg Ala Gly Val His Arg Phe Phe Ala
785                 790                 795                 800

Ser Leu Arg Leu His Gly Pro Pro Gly Val Ala Ser Ala Cys Gln Leu
                805                 810                 815

Leu Thr Arg Leu Ser Gln Thr Ser Pro Ala Gly Leu Lys Ala Val Leu
                820                 825                 830

Gln Leu Leu Val Glu Gly Ala Leu His Arg Gly Asn Thr Glu Leu Phe
            835                 840                 845

Gly Gly Gln Val Asp Gly Asp Asn Glu Thr Leu Ser Val Val Ser Ala
            850                 855                 860

Ser Leu Ala Ser Ala Ser Leu Leu Asp Thr Asn Arg Arg His Thr Ala
865                 870                 875                 880

Ala Val Pro Gly Pro Gly Gly Ile Trp Ser Val Phe His Ala Gly Val
                885                 890                 895

Ile Gly Arg Gly Leu Lys Pro Pro Lys Phe Val Gln Ser Arg Asn Gln
                900                 905                 910

Gln Glu Val Ile Tyr Asn Thr Gln Ser Leu Leu Ser Leu Val His
            915                 920                 925

Cys Cys Ser Ala Pro Gly Gly Thr Glu Cys Gly Glu Cys Trp Gly Ala
            930                 935                 940

Pro Ile Leu Ser Pro Glu Ala Ala Lys Ala Val Ala Val Thr Leu Val
945                 950                 955                 960

Glu Ser Val Cys Pro Asp Ala Ala Gly Ala Glu Leu Ala Trp Pro Pro
                965                 970                 975

Glu Glu His Ala Arg Ala Thr Val Glu Arg Asp Leu Arg Ile Gly Arg
                980                 985                 990

Arg Phe Arg Glu Gln Pro Leu Leu Phe Glu Leu Leu Lys Leu Val Ala
            995                 1000                1005

Ala Ala Pro Pro Ala Leu Cys Tyr Cys Ser Val Leu Leu Arg Gly
            1010                1015                1020

Leu Leu Ala Ala Leu Leu Gly His Trp Glu Ala Ser Arg His Pro
            1025                1030                1035

Asp Thr Thr His Ser Pro Trp His Leu Glu Ala Ser Cys Thr Leu
            1040                1045                1050

Val Ala Val Met Ala Glu Gly Ser Leu Leu Pro Pro Ala Leu Gly
            1055                1060                1065

Asn Met His Glu Val Phe Ser Gln Leu Ala Pro Phe Glu Val Arg
            1070                1075                1080

Leu Leu Leu Leu Ser Val Trp Gly Phe Leu Arg Glu His Gly Pro
            1085                1090                1095

Leu Pro Gln Lys Phe Ile Phe Gln Ser Glu Arg Gly Arg Phe Ile
            1100                1105                1110

Arg Asp Phe Ser Arg Glu Gly Gly Gly Glu Gly Gly Pro His Leu
            1115                1120                1125

Ala Val Leu His Ser Val Leu His Arg Asn Ile Asp Arg Leu Gly
            1130                1135                1140

Leu Phe Ser Gly Arg Phe Gln Ala Pro Ser Pro Ser Thr Leu Leu
```

```
                        1145                1150                1155
Arg Gln Gly Thr
        1160

<210> SEQ ID NO 5
<211> LENGTH: 1162
<212> TYPE: PRT
<213> ORGANISM: Artificial
<220> FEATURE:
<223> OTHER INFORMATION: A variant of the human BFLP1698 polypeptide

<400> SEQUENCE: 5

Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
            20                  25                  30

Pro Leu Trp Asp Arg Gly Lys Ile Gly Lys Val Glu Gly His Gln His
        35                  40                  45

Ile Gln Asp Phe Ser Gln Lys Ser His Leu Pro Ser Ile Val Val Glu
    50                  55                  60

Ser Ser Glu Val Asn Glu Glu Ser Gly Asp Leu His Leu Pro His Glu
65                  70                  75                  80

Glu Leu Leu Leu Leu Thr Asp Gly Glu Glu Asp Ala Glu Ala Phe
                85                  90                  95

Phe Gln Asp Gln Ser Glu Glu Pro Gly Ala Ala Arg Pro His His Gln
            100                 105                 110

Ala Arg Gln Val Glu His Ser Thr Gln Arg Gly His Leu Glu Ile Arg
        115                 120                 125

Glu Leu Lys Lys Lys Leu Phe Lys Arg Arg Val Leu Asn Arg Glu
    130                 135                 140

Arg Arg Leu Arg His Arg Val Val Gly Ala Val Ile Asp Gln Gly Leu
145                 150                 155                 160

Ile Thr Arg His His Leu Lys Lys Arg Ala Ala Gln Glu Leu Ser Gln
                165                 170                 175

Glu Ile Lys Ala Phe Leu Thr Gly Val Asp Pro Ile Leu Gly His Gln
            180                 185                 190

Leu Ser Ala Arg Glu His Ala Arg Cys Gly Leu Leu Leu Arg Ser
        195                 200                 205

Leu Pro Pro Ala Arg Ala Ala Val Leu Asp His Leu Arg Gly Val Phe
    210                 215                 220

Asp Glu Ser Val Arg Ala His Leu Ala Ala Leu Asp Glu Thr Pro Val
225                 230                 235                 240

Ala Gly Pro Pro His Leu Arg Pro Pro Pro Ser His Val Pro Ala
                245                 250                 255

Gly Gly Pro Gly Leu Glu Asp Val Val Gln Glu Val Gln Gln Val Leu
            260                 265                 270

Ser Glu Phe Ile Arg Ala Asn Pro Lys Ala Trp Ala Pro Val Ile Gly
        275                 280                 285

Ala Trp Ser Ile Asp Leu Met Gly Gln Leu Ser Ser Thr Tyr Ser Gly
    290                 295                 300

Gln His Gln Arg Val Pro His Ala Thr Gly Ala Leu Asn Glu Leu Leu
305                 310                 315                 320

Gln Leu Trp Met Gly Cys Arg Ala Thr Arg Thr Leu Met Asp Ile Tyr
                325                 330                 335

Val Gln Cys Leu Ser Ala Leu Ile Gly Ser Cys Pro Asp Ala Cys Val
```

```
              340             345             350
Asp Ala Leu Leu Asp Thr Ser Val Gln His Ser Pro His Phe Asp Trp
            355                 360                 365
Val Val Ala His Ile Gly Ser Ser Phe Pro Gly Thr Ile Ile Ser Arg
            370                 375                 380
Val Leu Ser Cys Gly Leu Lys Asp Phe Cys Val His Gly Gly Ala Gly
385                 390                 395                 400
Gly Gly Ala Gly Ser Ser Gly Gly Ser Ser Ser Gln Thr Pro Ser Thr
                405                 410                 415
Asp Pro Phe Pro Gly Ser Pro Ala Ile Pro Ala Glu Lys Arg Val Pro
            420                 425                 430
Lys Ile Ala Ser Val Val Gly Ile Leu Gly His Leu Ala Ser Arg His
            435                 440                 445
Gly Asp Ser Ile Arg Arg Glu Leu Leu Arg Met Phe His Asp Ser Leu
            450                 455                 460
Ala Gly Gly Ser Gly Gly Arg Ser Gly Asp Pro Ser Leu Gln Ala Thr
465                 470                 475                 480
Val Pro Phe Leu Leu Gln Leu Ala Val Met Ser Pro Ala Leu Leu Gly
                485                 490                 495
Thr Val Ser Gly Glu Leu Val Asp Cys Leu Lys Pro Pro Ala Val Leu
                500                 505                 510
Ser Gln Leu Gln Gln His Leu Gln Gly Phe Pro Arg Glu Glu Leu Asp
            515                 520                 525
Asn Met Leu Asn Leu Ala Val His Leu Val Ser Gln Ala Ser Gly Ala
            530                 535                 540
Gly Ala Tyr Arg Leu Leu Gln Phe Leu Val Asp Thr Ala Met Pro Ala
545                 550                 555                 560
Ser Val Ile Thr Thr Gln Gly Leu Ala Val Pro Asp Thr Val Arg Glu
                565                 570                 575
Ala Cys Asp Arg Leu Ile Gln Leu Leu Leu His Leu Gln Lys Leu
            580                 585                 590
Val His His Arg Gly Gly Ser Pro Gly Glu Gly Val Leu Gly Pro Pro
            595                 600                 605
Pro Pro Pro Arg Leu Val Pro Phe Leu Asp Ala Leu Lys Asn His Val
            610                 615                 620
Gly Glu Leu Cys Gly Glu Thr Leu Arg Leu Glu Arg Lys Arg Phe Leu
625                 630                 635                 640
Trp Gln His Gln Leu Leu Gly Leu Leu Ser Val Tyr Thr Arg Pro Ser
                645                 650                 655
Cys Gly Pro Glu Ala Leu Gly His Leu Leu Ser Arg Ala Arg Ser Pro
                660                 665                 670
Glu Glu Leu Ser Leu Ala Thr Gln Leu Tyr Ala Gly Leu Val Val Ser
            675                 680                 685
Leu Ser Gly Leu Leu Pro Leu Ala Phe Arg Ser Cys Leu Ala Arg Val
            690                 695                 700
His Ala Gly Thr Leu Gln Pro Pro Phe Thr Ala Arg Phe Leu Arg Asn
705                 710                 715                 720
Leu Ala Leu Leu Val Gly Trp Glu Gln Gln Gly Gly Glu Gly Pro Ala
                725                 730                 735
Ala Leu Gly Ala His Phe Gly Glu Ser Ala Ser Ala His Leu Ser Asp
            740                 745                 750
Leu Ala Pro Leu Leu Leu His Pro Glu Glu Glu Val Ala Glu Ala Ala
            755                 760                 765
```

```
Ala Ser Leu Leu Ala Ile Cys Pro Phe Pro Ser Glu Ala Leu Ser Pro
    770                 775                 780

Ser Gln Leu Leu Gly Leu Val Arg Ala Gly Val His Arg Phe Phe Ala
785                 790                 795                 800

Ser Leu Arg Leu His Gly Pro Pro Gly Val Ala Ser Ala Cys Gln Leu
                805                 810                 815

Leu Thr Arg Leu Ser Gln Thr Ser Pro Ala Gly Leu Lys Ala Val Leu
                820                 825                 830

Gln Leu Leu Val Glu Gly Ala Leu His Arg Gly Asn Thr Glu Leu Phe
                835                 840                 845

Gly Gly Gln Val Asp Gly Asp Asn Glu Thr Leu Ser Val Val Ser Ala
850                 855                 860

Ser Leu Ala Ser Ala Ser Leu Leu Asp Thr Asn Arg Arg His Thr Ala
865                 870                 875                 880

Ala Val Pro Gly Pro Gly Gly Ile Trp Ser Val Phe His Ala Gly Val
                885                 890                 895

Ile Gly Arg Gly Leu Lys Pro Pro Lys Phe Val Gln Ser Arg Asn Gln
                900                 905                 910

Gln Glu Val Ile Tyr Asn Thr Gln Ser Leu Leu Ser Leu Leu Val His
                915                 920                 925

Cys Cys Ser Ala Pro Gly Gly Thr Glu Cys Gly Glu Cys Trp Gly Ala
930                 935                 940

Pro Ile Leu Ser Pro Glu Ala Ala Lys Ala Val Ala Val Thr Leu Val
945                 950                 955                 960

Glu Ser Val Cys Pro Asp Ala Ala Gly Ala Glu Leu Ala Trp Pro Pro
                965                 970                 975

Glu Glu His Ala Arg Ala Thr Val Glu Arg Asp Leu Arg Ile Gly Arg
                980                 985                 990

Arg Phe Arg Glu Gln Pro Leu Leu Phe Glu Leu Leu Lys Leu Val Ala
                995                 1000                1005

Ala Ala Pro Pro Ala Leu Cys Tyr Cys Ser Val Leu Leu Arg Gly
    1010                1015                1020

Leu Leu Ala Ala Leu Leu Gly His Trp Glu Ala Ser Arg His Pro
    1025                1030                1035

Asp Thr Thr His Ser Pro Trp His Leu Glu Ala Ser Cys Thr Leu
    1040                1045                1050

Val Ala Val Met Ala Glu Gly Ser Leu Leu Pro Pro Ala Leu Gly
    1055                1060                1065

Asn Met His Glu Val Phe Ser Gln Leu Ala Pro Phe Glu Val Arg
    1070                1075                1080

Leu Leu Leu Leu Ser Val Trp Gly Phe Leu Arg Glu His Gly Pro
    1085                1090                1095

Leu Pro Gln Lys Phe Ile Phe Gln Ser Glu Arg Gly Arg Phe Ile
    1100                1105                1110

Arg Asp Phe Ser Arg Glu Gly Gly Gly Glu Gly Gly Pro His Leu
    1115                1120                1125

Ala Val Leu His Ser Val Leu His Arg Asn Ile Asp Arg Leu Gly
    1130                1135                1140

Leu Phe Ser Gly Arg Phe Gln Ala Pro Ser Pro Ser Thr Leu Leu
    1145                1150                1155

Arg Gln Gly Thr
    1160
```

-continued

<210> SEQ ID NO 6
<211> LENGTH: 1162
<212> TYPE: PRT
<213> ORGANISM: Artificial
<220> FEATURE:
<223> OTHER INFORMATION: A variant of the human BFLP1698 polypeptide

<400> SEQUENCE: 6

```
Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
            20                  25                  30

Pro Leu Trp Asp Arg Gly Lys Ile Gly Lys Val Glu Gly His Gln His
        35                  40                  45

Ile Gln Asp Phe Ser Gln Lys Ser His Leu Pro Ser Ile Val Val Glu
    50                  55                  60

Ser Ser Glu Val Asn Glu Glu Ser Gly Asp Leu His Leu Pro His Glu
65                  70                  75                  80

Glu Leu Leu Leu Thr Asp Gly Glu Glu Asp Ala Glu Ala Phe
                85                  90                  95

Phe Gln Asp Gln Ser Glu Glu Pro Gly Ala Ala Arg Pro His His Gln
                100                 105                 110

Ala Arg Gln Val Glu His Ser Thr Gln Arg Gly His Leu Glu Ile Arg
            115                 120                 125

Glu Leu Lys Lys Lys Leu Phe Lys Arg Arg Val Leu Asn Arg Glu
130                 135                 140

Arg Arg Leu Arg His Arg Val Val Gly Ala Val Ile Asp Gln Gly Leu
145                 150                 155                 160

Ile Thr Arg His His Leu Lys Lys Arg Ala Ala Gln Glu Leu Ser Gln
                165                 170                 175

Glu Ile Lys Ala Phe Leu Thr Gly Val Asp Pro Ile Leu Gly His Gln
            180                 185                 190

Leu Ser Ala Arg Glu His Ala Arg Cys Gly Leu Leu Leu Arg Ser
        195                 200                 205

Leu Pro Pro Ala Arg Ala Ala Val Leu Asp His Leu Arg Gly Val Phe
210                 215                 220

Asp Glu Ser Val Arg Ala His Leu Ala Ala Leu Asp Glu Thr Pro Val
225                 230                 235                 240

Ala Gly Pro Pro His Leu Arg Pro Pro Pro Ser His Val Pro Ala
                245                 250                 255

Gly Gly Pro Gly Leu Glu Asp Val Val Gln Glu Val Gln Gln Val Leu
            260                 265                 270

Ser Glu Phe Ile Arg Ala Asn Pro Lys Ala Trp Ala Pro Val Ile Ser
        275                 280                 285

Ala Trp Ser Ile Asp Leu Met Gly Gln Leu Ser Ser Thr Tyr Ser Gly
    290                 295                 300

Gln His Gln Arg Val Pro His Ala Thr Gly Ala Leu Asn Glu Leu Leu
305                 310                 315                 320

Gln Leu Trp Met Gly Cys Arg Ala Thr Arg Thr Leu Met Asp Ile Tyr
                325                 330                 335

Val Gln Cys Leu Ser Ala Leu Ile Gly Ser Cys Pro Asp Ala Cys Val
            340                 345                 350

Asp Ala Leu Leu Asp Thr Ser Val Gln His Ser Pro Arg Phe Asp Trp
        355                 360                 365
```

-continued

```
Val Val Ala His Ile Gly Ser Ser Phe Pro Gly Thr Ile Ile Ser Arg
    370                 375                 380

Val Leu Ser Cys Gly Leu Lys Asp Phe Cys Val His Gly Gly Ala Gly
385                 390                 395                 400

Gly Gly Ala Gly Ser Ser Gly Gly Ser Ser Gln Thr Pro Ser Thr
                405                 410                 415

Asp Pro Phe Pro Gly Ser Pro Ala Ile Pro Ala Glu Lys Arg Val Pro
            420                 425                 430

Lys Ile Ala Ser Val Val Gly Ile Leu Gly His Leu Ala Ser Arg His
                435                 440                 445

Gly Asp Ser Ile Arg Arg Glu Leu Leu Arg Met Phe His Asp Ser Leu
    450                 455                 460

Ala Gly Ser Gly Gly Arg Ser Gly Asp Pro Ser Leu Gln Ala Thr
465                 470                 475                 480

Val Pro Phe Leu Leu Gln Leu Ala Val Met Ser Pro Ala Leu Leu Gly
                485                 490                 495

Thr Val Ser Gly Glu Leu Val Asp Cys Leu Lys Pro Pro Ala Val Leu
            500                 505                 510

Ser Gln Leu Gln Gln His Leu Gln Gly Phe Pro Arg Glu Glu Leu Asp
                515                 520                 525

Asn Met Leu Asn Leu Ala Val His Leu Val Ser Gln Ala Ser Gly Ala
    530                 535                 540

Gly Ala Tyr Arg Leu Leu Gln Phe Leu Val Asp Thr Ala Met Pro Ala
545                 550                 555                 560

Ser Val Ile Thr Thr Gln Gly Leu Ala Val Pro Asp Thr Val Arg Glu
                565                 570                 575

Ala Cys Asp Arg Leu Ile Gln Leu Leu Leu His Leu Gln Lys Leu
            580                 585                 590

Val His His Arg Gly Gly Ser Pro Gly Glu Gly Val Leu Gly Pro Pro
    595                 600                 605

Pro Pro Pro Arg Leu Val Pro Phe Leu Asp Ala Leu Lys Asn His Val
        610                 615                 620

Gly Glu Leu Cys Gly Glu Thr Leu Arg Leu Glu Arg Lys Arg Phe Leu
625                 630                 635                 640

Trp Gln His Gln Leu Leu Gly Leu Leu Ser Val Tyr Thr Arg Pro Ser
                645                 650                 655

Cys Gly Pro Glu Ala Leu Gly His Leu Leu Ser Arg Ala Arg Ser Pro
            660                 665                 670

Glu Glu Leu Ser Leu Ala Thr Gln Leu Tyr Ala Gly Leu Val Val Ser
    675                 680                 685

Leu Ser Gly Leu Leu Pro Leu Ala Phe Arg Ser Cys Leu Ala Arg Val
    690                 695                 700

His Ala Gly Thr Leu Gln Pro Pro Phe Thr Ala Arg Phe Leu Arg Asn
705                 710                 715                 720

Leu Ala Leu Leu Val Gly Trp Glu Gln Gln Gly Gly Glu Gly Pro Ala
                725                 730                 735

Ala Leu Gly Ala His Phe Gly Glu Ser Ala Ser His Leu Ser Asp
            740                 745                 750

Leu Ala Pro Leu Leu Leu His Pro Glu Glu Val Ala Glu Ala Ala
    755                 760                 765

Ala Ser Leu Leu Ala Ile Cys Pro Phe Pro Ser Glu Ala Leu Ser Pro
    770                 775                 780

Ser Gln Leu Leu Gly Leu Val Arg Ala Gly Val His Arg Phe Phe Ala
```

```
                    785                 790                 795                 800

Ser Leu Arg Leu His Gly Pro Pro Gly Val Ala Ser Ala Cys Gln Leu
                805                 810                 815

Leu Thr Arg Leu Ser Gln Thr Ser Pro Ala Gly Leu Lys Ala Val Leu
            820                 825                 830

Gln Leu Leu Val Glu Gly Ala Leu His Arg Gly Asn Thr Glu Leu Phe
        835                 840                 845

Gly Gly Gln Val Asp Gly Asp Asn Glu Thr Leu Ser Val Val Ser Ala
    850                 855                 860

Ser Leu Ala Ser Ala Ser Leu Leu Asp Thr Asn Arg Arg His Thr Ala
865                 870                 875                 880

Ala Val Pro Gly Pro Gly Gly Ile Trp Ser Val Phe His Ala Gly Val
                885                 890                 895

Ile Gly Arg Gly Leu Lys Pro Pro Lys Phe Val Gln Ser Arg Asn Gln
            900                 905                 910

Gln Glu Val Ile Tyr Asn Thr Gln Ser Leu Leu Ser Leu Leu Val His
        915                 920                 925

Cys Cys Ser Ala Pro Gly Gly Thr Glu Cys Gly Glu Cys Trp Gly Ala
    930                 935                 940

Pro Ile Leu Ser Pro Glu Ala Ala Lys Ala Val Ala Val Thr Leu Val
945                 950                 955                 960

Glu Ser Val Cys Pro Asp Ala Ala Gly Ala Glu Leu Ala Trp Pro Pro
                965                 970                 975

Glu Glu His Ala Arg Ala Thr Val Glu Arg Asp Leu Arg Ile Gly Arg
            980                 985                 990

Arg Phe Arg Glu Gln Pro Leu Leu  Phe Glu Leu Leu  Lys Leu Val Ala
        995                 1000                1005

Ala Ala  Pro Pro Ala Leu Cys  Tyr Cys Ser Val Leu  Leu Arg Gly
    1010                1015                1020

Leu Leu  Ala Ala Leu Leu Gly  His Trp Glu Ala Ser  Arg His Pro
    1025                1030                1035

Asp Thr  Thr His Ser Pro Trp  His Leu Glu Ala Ser  Cys Thr Leu
    1040                1045                1050

Val Ala  Val Met Ala Glu Gly  Ser Leu Leu Pro  Ala Leu Gly
    1055                1060                1065

Asn Met  His Glu Val Phe Ser  Gln Leu Ala Pro Phe  Glu Val Arg
    1070                1075                1080

Leu Leu  Leu Leu Ser Val Trp  Gly Phe Leu Arg Glu  His Gly Pro
    1085                1090                1095

Leu Pro  Gln Lys Phe Ile Phe  Gln Ser Glu Arg Gly  Arg Phe Ile
    1100                1105                1110

Arg Asp  Phe Ser Arg Glu Gly  Gly Gly Glu Gly  Pro His Leu
    1115                1120                1125

Ala Val  Leu His Ser Val Leu  His Arg Asn Ile Asp  Arg Leu Gly
    1130                1135                1140

Leu Phe  Ser Gly Arg Phe Gln  Ala Pro Ser Pro Ser  Thr Leu Leu
    1145                1150                1155

Arg Gln  Gly Thr
    1160

<210> SEQ ID NO 7
<211> LENGTH: 1162
<212> TYPE: PRT
<213> ORGANISM: Artificial
```

```
<220> FEATURE:
<223> OTHER INFORMATION: A variant of the human BFLP1698 polypeptide

<400> SEQUENCE: 7

Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
            20                  25                  30

Pro Leu Trp Asp Arg Gly Lys Ile Gly Lys Val Glu Gly His Gln His
        35                  40                  45

Ile Gln Asp Phe Ser Gln Lys Ser His Leu Pro Ser Ile Val Val Glu
    50                  55                  60

Ser Ser Glu Val Asn Glu Glu Ser Gly Asp Leu His Leu Pro His Glu
65                  70                  75                  80

Glu Leu Leu Leu Thr Asp Gly Glu Glu Asp Ala Glu Ala Phe
                85                  90                  95

Phe Gln Asp Gln Ser Glu Glu Pro Gly Ala Ala Arg Pro His His Gln
                100                 105                 110

Ala Arg Gln Val Glu His Ser Thr Gln Arg Gly His Leu Glu Ile Arg
            115                 120                 125

Glu Leu Lys Lys Lys Leu Phe Lys Arg Arg Val Leu Asn Arg Glu
130                 135                 140

Arg Arg Leu Arg His Arg Val Val Gly Ala Val Ile Asp Gln Gly Leu
145                 150                 155                 160

Ile Thr Arg His His Leu Lys Lys Arg Ala Ala Gln Glu Leu Ser Gln
                165                 170                 175

Glu Ile Lys Ala Phe Leu Thr Gly Val Asp Pro Ile Leu Gly His Gln
            180                 185                 190

Leu Ser Ala Arg Glu His Ala Arg Cys Gly Leu Leu Leu Arg Ser
        195                 200                 205

Leu Pro Pro Ala Arg Ala Ala Val Leu Asp His Leu Arg Gly Val Phe
    210                 215                 220

Asp Glu Ser Val Arg Ala His Leu Ala Ala Leu Asp Glu Thr Pro Val
225                 230                 235                 240

Ala Gly Pro Pro His Leu Arg Pro Pro Pro Ser His Val Pro Ala
                245                 250                 255

Gly Gly Pro Gly Leu Glu Asp Val Val Gln Glu Val Gln Gln Val Leu
            260                 265                 270

Ser Glu Phe Ile Arg Ala Asn Pro Lys Ala Trp Ala Pro Val Ile Ser
        275                 280                 285

Ala Trp Ser Ile Asp Leu Met Gly Gln Leu Ser Ser Thr Tyr Ser Gly
    290                 295                 300

Gln His Gln Arg Val Pro His Ala Thr Gly Ala Leu Asn Glu Leu Leu
305                 310                 315                 320

Gln Leu Trp Met Gly Cys Arg Ala Thr Arg Thr Leu Met Asp Ile Tyr
                325                 330                 335

Val Gln Cys Leu Ser Ala Leu Ile Gly Ser Cys Pro Asp Ala Cys Val
            340                 345                 350

Asp Ala Leu Leu Asp Thr Ser Val Gln His Ser Pro His Phe Asp Trp
        355                 360                 365

Val Val Ala His Ile Gly Ser Ser Phe Pro Gly Thr Ile Ile Ser Arg
    370                 375                 380

Val Leu Ser Cys Gly Leu Lys Asp Phe Cys Val His Gly Gly Ala Gly
385                 390                 395                 400
```

-continued

Gly Gly Ala Gly Ser Ser Gly Gly Ser Ser Gln Thr Pro Ser Thr
              405                 410                 415

Asp Pro Phe Pro Gly Ser Pro Ala Ile Pro Ala Glu Lys Arg Val Pro
            420                 425                 430

Lys Ile Ala Ser Val Val Gly Ile Leu Gly His Leu Ala Ser Arg His
        435                 440                 445

Gly Asp Ser Ile Arg Arg Glu Leu Leu Arg Met Phe His Asp Ser Leu
    450                 455                 460

Ala Gly Gly Ser Gly Gly Arg Ser Gly Asp Pro Ser Leu Gln Ala Thr
465                 470                 475                 480

Met Pro Phe Leu Leu Gln Leu Ala Val Met Ser Pro Ala Leu Leu Gly
                485                 490                 495

Thr Val Ser Gly Glu Leu Val Asp Cys Leu Lys Pro Pro Ala Val Leu
            500                 505                 510

Ser Gln Leu Gln Gln His Leu Gln Gly Phe Pro Arg Glu Glu Leu Asp
        515                 520                 525

Asn Met Leu Asn Leu Ala Val His Leu Val Ser Gln Ala Ser Gly Ala
    530                 535                 540

Gly Ala Tyr Arg Leu Leu Gln Phe Leu Val Asp Thr Ala Met Pro Ala
545                 550                 555                 560

Ser Val Ile Thr Thr Gln Gly Leu Ala Val Pro Asp Thr Val Arg Glu
                565                 570                 575

Ala Cys Asp Arg Leu Ile Gln Leu Leu Leu His Leu Gln Lys Leu
            580                 585                 590

Val His His Arg Gly Gly Ser Pro Gly Glu Gly Val Leu Gly Pro Pro
        595                 600                 605

Pro Pro Pro Arg Leu Val Pro Phe Leu Asp Ala Leu Lys Asn His Val
    610                 615                 620

Gly Glu Leu Cys Gly Glu Thr Leu Arg Leu Glu Arg Lys Arg Phe Leu
625                 630                 635                 640

Trp Gln His Gln Leu Leu Gly Leu Leu Ser Val Tyr Thr Arg Pro Ser
                645                 650                 655

Cys Gly Pro Glu Ala Leu Gly His Leu Leu Ser Arg Ala Arg Ser Pro
            660                 665                 670

Glu Glu Leu Ser Leu Ala Thr Gln Leu Tyr Ala Gly Leu Val Val Ser
        675                 680                 685

Leu Ser Gly Leu Leu Pro Leu Ala Phe Arg Ser Cys Leu Ala Arg Val
    690                 695                 700

His Ala Gly Thr Leu Gln Pro Pro Phe Thr Ala Arg Phe Leu Arg Asn
705                 710                 715                 720

Leu Ala Leu Leu Val Gly Trp Glu Gln Gln Gly Gly Glu Gly Pro Ala
                725                 730                 735

Ala Leu Gly Ala His Phe Gly Glu Ser Ala Ser His Leu Ser Asp
            740                 745                 750

Leu Ala Pro Leu Leu Leu His Pro Glu Glu Val Ala Glu Ala Ala
        755                 760                 765

Ala Ser Leu Leu Ala Ile Cys Pro Phe Pro Ser Glu Ala Leu Ser Pro
    770                 775                 780

Ser Gln Leu Leu Gly Leu Val Arg Ala Gly Val His Arg Phe Phe Ala
785                 790                 795                 800

Ser Leu Arg Leu His Gly Pro Pro Gly Val Ala Ser Ala Cys Gln Leu
                805                 810                 815

```
Leu Thr Arg Leu Ser Gln Thr Ser Pro Ala Gly Leu Lys Ala Val Leu
                820                 825                 830

Gln Leu Leu Val Glu Gly Ala Leu His Arg Gly Asn Thr Glu Leu Phe
            835                 840                 845

Gly Gly Gln Val Asp Gly Asp Asn Glu Thr Leu Ser Val Val Ser Ala
        850                 855                 860

Ser Leu Ala Ser Ala Ser Leu Leu Asp Thr Asn Arg Arg His Thr Ala
865                 870                 875                 880

Ala Val Pro Gly Pro Gly Gly Ile Trp Ser Val Phe His Ala Gly Val
                885                 890                 895

Ile Gly Arg Gly Leu Lys Pro Pro Lys Phe Val Gln Ser Arg Asn Gln
            900                 905                 910

Gln Glu Val Ile Tyr Asn Thr Gln Ser Leu Leu Ser Leu Leu Val His
        915                 920                 925

Cys Cys Ser Ala Pro Gly Gly Thr Glu Cys Gly Glu Cys Trp Gly Ala
930                 935                 940

Pro Ile Leu Ser Pro Glu Ala Ala Lys Ala Val Ala Val Thr Leu Val
945                 950                 955                 960

Glu Ser Val Cys Pro Asp Ala Ala Gly Ala Glu Leu Ala Trp Pro Pro
                965                 970                 975

Glu Glu His Ala Arg Ala Thr Val Glu Arg Asp Leu Arg Ile Gly Arg
            980                 985                 990

Arg Phe Arg Glu Gln Pro Leu Leu Phe Glu Leu Leu Lys Leu Val Ala
        995                 1000                1005

Ala Ala Pro Pro Ala Leu Cys Tyr Cys Ser Val Leu Leu Arg Gly
    1010                1015                1020

Leu Leu Ala Ala Leu Leu Gly His Trp Glu Ala Ser Arg His Pro
    1025                1030                1035

Asp Thr Thr His Ser Pro Trp His Leu Glu Ala Ser Cys Thr Leu
    1040                1045                1050

Val Ala Val Met Ala Glu Gly Ser Leu Leu Pro Pro Ala Leu Gly
    1055                1060                1065

Asn Met His Glu Val Phe Ser Gln Leu Ala Pro Phe Glu Val Arg
    1070                1075                1080

Leu Leu Leu Ser Val Trp Gly Phe Leu Arg Glu His Gly Pro
    1085                1090                1095

Leu Pro Gln Lys Phe Ile Phe Gln Ser Glu Arg Gly Arg Phe Ile
    1100                1105                1110

Arg Asp Phe Ser Arg Glu Gly Gly Glu Gly Gly Pro His Leu
    1115                1120                1125

Ala Val Leu His Ser Val Leu His Arg Asn Ile Asp Arg Leu Gly
    1130                1135                1140

Leu Phe Ser Gly Arg Phe Gln Ala Pro Ser Pro Ser Thr Leu Leu
    1145                1150                1155

Arg Gln Gly Thr
    1160

<210> SEQ ID NO 8
<211> LENGTH: 1162
<212> TYPE: PRT
<213> ORGANISM: Artificial
<220> FEATURE:
<223> OTHER INFORMATION: A variant of the human BFLP1698 polypeptide

<400> SEQUENCE: 8
```

-continued

```
Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
            20                  25                  30

Pro Leu Trp Asp Arg Gly Lys Ile Gly Lys Val Glu Gly His Gln His
        35                  40                  45

Ile Gln Asp Phe Ser Gln Lys Ser His Leu Pro Ser Ile Val Val Glu
50                  55                  60

Ser Ser Glu Val Asn Glu Glu Ser Gly Asp Leu His Leu Pro His Glu
65                  70                  75                  80

Glu Leu Leu Leu Leu Thr Asp Gly Glu Glu Asp Ala Glu Ala Phe
                85                  90                  95

Phe Gln Asp Gln Ser Glu Glu Pro Gly Ala Ala Arg Pro His His Gln
                100                 105                 110

Ala Arg Gln Val Glu His Ser Thr Gln Arg Gly His Leu Glu Ile Arg
            115                 120                 125

Glu Leu Lys Lys Lys Leu Phe Lys Arg Arg Val Leu Asn Arg Glu
            130                 135                 140

Arg Arg Leu Arg His Arg Val Gly Ala Val Ile Asp Gln Gly Leu
145                 150                 155                 160

Ile Thr Arg His His Leu Lys Lys Arg Ala Ala Gln Glu Leu Ser Gln
                165                 170                 175

Glu Ile Lys Ala Phe Leu Thr Gly Val Asp Pro Ile Leu Gly His Gln
            180                 185                 190

Leu Ser Ala Arg Glu His Ala Arg Cys Gly Leu Leu Leu Arg Ser
        195                 200                 205

Leu Pro Pro Ala Arg Ala Ala Val Leu Asp His Leu Arg Gly Val Phe
210                 215                 220

Asp Glu Ser Val Arg Ala His Leu Ala Ala Leu Asp Glu Thr Pro Val
225                 230                 235                 240

Ala Gly Pro Pro His Leu Arg Pro Pro Pro Ser His Val Pro Ala
                245                 250                 255

Gly Gly Pro Gly Leu Glu Asp Val Val Gln Glu Val Gln Gln Val Leu
            260                 265                 270

Ser Glu Phe Ile Arg Ala Asn Pro Lys Ala Trp Ala Pro Val Ile Ser
            275                 280                 285

Ala Trp Ser Ile Asp Leu Met Gly Gln Leu Ser Ser Thr Tyr Ser Gly
290                 295                 300

Gln His Gln Arg Val Pro His Ala Thr Gly Ala Leu Asn Glu Leu Leu
305                 310                 315                 320

Gln Leu Trp Met Gly Cys Arg Ala Thr Arg Thr Leu Met Asp Ile Tyr
                325                 330                 335

Val Gln Cys Leu Ser Ala Leu Ile Gly Ser Cys Pro Asp Ala Cys Val
            340                 345                 350

Asp Ala Leu Leu Asp Thr Ser Val Gln His Ser Pro His Phe Asp Trp
            355                 360                 365

Val Val Ala His Ile Gly Ser Ser Phe Pro Gly Thr Ile Ile Ser Arg
        370                 375                 380

Val Leu Ser Cys Gly Leu Lys Asp Phe Cys Val His Gly Gly Ala Gly
385                 390                 395                 400

Gly Gly Ala Gly Ser Ser Gly Gly Ser Ser Ser Gln Thr Pro Ser Thr
                405                 410                 415

Asp Pro Phe Pro Gly Ser Pro Ala Ile Pro Ala Glu Lys Arg Val Pro
```

-continued

```
                420                 425                 430
Lys Ile Ala Ser Val Val Gly Ile Leu Gly His Leu Ala Ser Arg His
            435                 440                 445
Gly Asp Ser Ile Arg Arg Glu Leu Leu Arg Met Phe His Asp Ser Leu
        450                 455                 460
Ala Gly Gly Ser Gly Gly Arg Ser Gly Asp Pro Ser Leu Gln Ala Thr
465                 470                 475                 480
Val Pro Phe Leu Leu Gln Leu Ala Val Met Ser Pro Ala Leu Leu Gly
                485                 490                 495
Thr Val Ser Gly Glu Leu Val Asp Cys Leu Lys Pro Ala Val Leu
            500                 505                 510
Ser Gln Leu Gln Gln His Leu Gln Gly Phe Pro Arg Glu Glu Leu Asp
        515                 520                 525
Asn Met Leu Asn Leu Ala Val His Leu Val Ser Gln Ala Ser Gly Ala
    530                 535                 540
Gly Ala Tyr Arg Leu Leu Gln Phe Leu Val Asp Tyr Ala Met Pro Ala
545                 550                 555                 560
Ser Val Ile Thr Thr Gln Gly Leu Ala Val Pro Asp Thr Val Arg Glu
                565                 570                 575
Ala Cys Asp Arg Leu Ile Gln Leu Leu Leu His Leu Gln Lys Leu
            580                 585                 590
Val His His Arg Gly Gly Ser Pro Gly Glu Gly Val Leu Gly Pro Pro
        595                 600                 605
Pro Pro Pro Arg Leu Val Pro Phe Leu Asp Ala Leu Lys Asn His Val
    610                 615                 620
Gly Glu Leu Cys Gly Glu Thr Leu Arg Leu Glu Arg Lys Arg Phe Leu
625                 630                 635                 640
Trp Gln His Gln Leu Leu Gly Leu Leu Ser Val Tyr Thr Arg Pro Ser
                645                 650                 655
Cys Gly Pro Glu Ala Leu Gly His Leu Leu Ser Arg Ala Arg Ser Pro
            660                 665                 670
Glu Glu Leu Ser Leu Ala Thr Gln Leu Tyr Ala Gly Leu Val Val Ser
        675                 680                 685
Leu Ser Gly Leu Leu Pro Leu Ala Phe Arg Ser Cys Leu Ala Arg Val
    690                 695                 700
His Ala Gly Thr Leu Gln Pro Pro Phe Thr Ala Arg Phe Leu Arg Asn
705                 710                 715                 720
Leu Ala Leu Leu Val Gly Trp Glu Gln Gln Gly Gly Glu Gly Pro Ala
                725                 730                 735
Ala Leu Gly Ala His Phe Gly Glu Ser Ala Ser Ala His Leu Ser Asp
            740                 745                 750
Leu Ala Pro Leu Leu His Pro Glu Glu Val Ala Glu Ala Ala
        755                 760                 765
Ala Ser Leu Leu Ala Ile Cys Pro Phe Pro Ser Glu Ala Leu Ser Pro
    770                 775                 780
Ser Gln Leu Leu Gly Leu Val Arg Ala Gly Val His Arg Phe Phe Ala
785                 790                 795                 800
Ser Leu Arg Leu His Gly Pro Pro Gly Val Ala Ser Ala Cys Gln Leu
                805                 810                 815
Leu Thr Arg Leu Ser Gln Thr Ser Pro Ala Gly Leu Lys Ala Val Leu
            820                 825                 830
Gln Leu Leu Val Glu Gly Ala Leu His Arg Gly Asn Thr Glu Leu Phe
        835                 840                 845
```

Gly Gly Gln Val Asp Gly Asp Asn Glu Thr Leu Ser Val Val Ser Ala
            850                 855                 860

Ser Leu Ala Ser Ala Ser Leu Leu Asp Thr Asn Arg Arg His Thr Ala
865                 870                 875                 880

Ala Val Pro Gly Pro Gly Ile Trp Ser Val Phe His Ala Gly Val
                885                 890                 895

Ile Gly Arg Gly Leu Lys Pro Pro Lys Phe Val Gln Ser Arg Asn Gln
            900                 905                 910

Gln Glu Val Ile Tyr Asn Thr Gln Ser Leu Leu Ser Leu Val His
            915                 920                 925

Cys Cys Ser Ala Pro Gly Gly Thr Glu Cys Gly Glu Cys Trp Gly Ala
            930                 935                 940

Pro Ile Leu Ser Pro Glu Ala Ala Lys Ala Val Ala Val Thr Leu Val
945                 950                 955                 960

Glu Ser Val Cys Pro Asp Ala Ala Gly Ala Glu Leu Ala Trp Pro Pro
                965                 970                 975

Glu Glu His Ala Arg Ala Thr Val Glu Arg Asp Leu Arg Ile Gly Arg
            980                 985                 990

Arg Phe Arg Glu Gln Pro Leu Leu Phe Glu Leu Leu Lys Leu Val Ala
            995                 1000                1005

Ala Ala Pro Pro Ala Leu Cys Tyr Cys Ser Val Leu Leu Arg Gly
        1010                1015                1020

Leu Leu Ala Ala Leu Leu Gly His Trp Glu Ala Ser Arg His Pro
        1025                1030                1035

Asp Thr Thr His Ser Pro Trp His Leu Glu Ala Ser Cys Thr Leu
        1040                1045                1050

Val Ala Val Met Ala Glu Gly Ser Leu Leu Pro Pro Ala Leu Gly
        1055                1060                1065

Asn Met His Glu Val Phe Ser Gln Leu Ala Pro Phe Glu Val Arg
        1070                1075                1080

Leu Leu Leu Leu Ser Val Trp Gly Phe Leu Arg Glu His Gly Pro
        1085                1090                1095

Leu Pro Gln Lys Phe Ile Phe Gln Ser Glu Arg Gly Arg Phe Ile
        1100                1105                1110

Arg Asp Phe Ser Arg Glu Gly Gly Glu Gly Gly Pro His Leu
        1115                1120                1125

Ala Val Leu His Ser Val Leu His Arg Asn Ile Asp Arg Leu Gly
        1130                1135                1140

Leu Phe Ser Gly Arg Phe Gln Ala Pro Ser Pro Ser Thr Leu Leu
        1145                1150                1155

Arg Gln Gly Thr
        1160

<210> SEQ ID NO 9
<211> LENGTH: 1162
<212> TYPE: PRT
<213> ORGANISM: Artificial
<220> FEATURE:
<223> OTHER INFORMATION: A variant of the human BFLP1698 polypeptide

<400> SEQUENCE: 9

Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
            20                  25                  30

-continued

```
Pro Leu Trp Asp Arg Gly Lys Ile Gly Lys Val Glu Gly His Gln His
        35                  40                  45

Ile Gln Asp Phe Ser Gln Lys Ser His Leu Pro Ser Ile Val Val Glu
    50                  55                  60

Ser Ser Glu Val Asn Glu Ser Gly Asp Leu His Leu Pro His Glu
65                  70                  75                  80

Glu Leu Leu Leu Leu Thr Asp Gly Glu Glu Asp Ala Glu Ala Phe
                85                  90                  95

Phe Gln Asp Gln Ser Glu Glu Pro Gly Ala Ala Arg Pro His His Gln
            100                 105                 110

Ala Arg Gln Val Glu His Ser Thr Gln Arg Gly His Leu Glu Ile Arg
        115                 120                 125

Glu Leu Lys Lys Lys Leu Phe Lys Arg Arg Val Leu Asn Arg Glu
    130                 135                 140

Arg Arg Leu Arg His Arg Val Val Gly Ala Val Ile Asp Gln Gly Leu
145                 150                 155                 160

Ile Thr Arg His His Leu Lys Lys Arg Ala Ala Gln Glu Leu Ser Gln
                165                 170                 175

Glu Ile Lys Ala Phe Leu Thr Gly Val Asp Pro Ile Leu Gly His Gln
            180                 185                 190

Leu Ser Ala Arg Glu His Ala Arg Cys Gly Leu Leu Leu Arg Ser
        195                 200                 205

Leu Pro Pro Ala Arg Ala Ala Val Leu Asp His Leu Arg Gly Val Phe
    210                 215                 220

Asp Glu Ser Val Arg Ala His Leu Ala Ala Leu Asp Glu Thr Pro Val
225                 230                 235                 240

Ala Gly Pro Pro His Leu Arg Pro Pro Pro Ser His Val Pro Ala
                245                 250                 255

Gly Gly Pro Gly Leu Glu Asp Val Val Gln Glu Val Gln Gln Val Leu
            260                 265                 270

Ser Glu Phe Ile Arg Ala Asn Pro Lys Ala Trp Ala Pro Val Ile Ser
        275                 280                 285

Ala Trp Ser Ile Asp Leu Met Gly Gln Leu Ser Ser Thr Tyr Ser Gly
    290                 295                 300

Gln His Gln Arg Val Pro His Ala Thr Gly Ala Leu Asn Glu Leu Leu
305                 310                 315                 320

Gln Leu Trp Met Gly Cys Arg Ala Thr Arg Thr Leu Met Asp Ile Tyr
                325                 330                 335

Val Gln Cys Leu Ser Ala Leu Ile Gly Ser Cys Pro Asp Ala Cys Val
            340                 345                 350

Asp Ala Leu Leu Asp Thr Ser Val Gln His Ser Pro His Phe Asp Trp
        355                 360                 365

Val Val Ala His Ile Gly Ser Ser Phe Pro Gly Thr Ile Ile Ser Arg
    370                 375                 380

Val Leu Ser Cys Gly Leu Lys Asp Phe Cys Val His Gly Gly Ala Gly
385                 390                 395                 400

Gly Gly Ala Gly Ser Ser Gly Gly Ser Ser Ser Gln Thr Pro Ser Thr
                405                 410                 415

Asp Pro Phe Pro Gly Ser Pro Ala Ile Pro Ala Glu Lys Arg Val Pro
            420                 425                 430

Lys Ile Ala Ser Val Val Gly Ile Leu Gly His Leu Ala Ser Arg His
        435                 440                 445
```

```
Gly Asp Ser Ile Arg Arg Glu Leu Leu Arg Met Phe His Asp Ser Leu
    450                 455                 460

Ala Gly Gly Ser Gly Gly Arg Ser Gly Asp Pro Ser Leu Gln Ala Thr
465                 470                 475                 480

Val Pro Phe Leu Leu Gln Leu Ala Val Met Ser Pro Ala Leu Leu Gly
                485                 490                 495

Thr Val Ser Gly Glu Leu Val Asp Cys Leu Lys Pro Pro Ala Val Leu
            500                 505                 510

Ser Gln Leu Gln Gln His Leu Gln Gly Phe Pro Arg Glu Glu Leu Asp
        515                 520                 525

Asn Met Leu Asn Leu Ala Val His Leu Val Ser Gln Ala Ser Gly Ala
    530                 535                 540

Gly Ala Tyr Arg Leu Leu Gln Phe Leu Val Asp Thr Ala Met Pro Ala
545                 550                 555                 560

Ser Val Ile Thr Thr Gln Gly Leu Ala Val Pro Asp Thr Val Arg Glu
                565                 570                 575

Ala Cys Asp Arg Leu Ile Gln Leu Leu Leu His Leu Gln Lys Leu
            580                 585                 590

Val His His Arg Gly Gly Ser Pro Gly Glu Gly Val Leu Gly Pro Pro
        595                 600                 605

Pro Pro Pro Arg Leu Val Pro Phe Leu Asp Ala Leu Lys Asn His Val
    610                 615                 620

Gly Glu Leu Cys Gly Glu Thr Leu Arg Leu Glu Arg Lys Arg Phe Leu
625                 630                 635                 640

Trp Gln His Gln Leu Leu Gly Leu Leu Ser Val Tyr Thr Arg Pro Ser
                645                 650                 655

Cys Gly Pro Glu Ala Leu Pro His Leu Leu Ser Arg Ala Arg Ser Pro
            660                 665                 670

Glu Glu Leu Ser Leu Ala Thr Gln Leu Tyr Ala Gly Leu Val Val Ser
        675                 680                 685

Leu Ser Gly Leu Leu Pro Leu Ala Phe Arg Ser Cys Leu Ala Arg Val
    690                 695                 700

His Ala Gly Thr Leu Gln Pro Pro Phe Thr Arg Phe Leu Arg Asn
705                 710                 715                 720

Leu Ala Leu Leu Val Gly Trp Glu Gln Gln Gly Gly Glu Gly Pro Ala
                725                 730                 735

Ala Leu Gly Ala His Phe Gly Glu Ser Ala Ser Ala His Leu Ser Asp
            740                 745                 750

Leu Ala Pro Leu Leu Leu His Pro Glu Glu Val Ala Glu Ala Ala
        755                 760                 765

Ala Ser Leu Leu Ala Ile Cys Pro Phe Pro Ser Glu Ala Leu Ser Pro
    770                 775                 780

Ser Gln Leu Leu Gly Leu Val Arg Ala Gly Val His Arg Phe Phe Ala
785                 790                 795                 800

Ser Leu Arg Leu His Gly Pro Pro Gly Val Ala Ser Ala Cys Gln Leu
                805                 810                 815

Leu Thr Arg Leu Ser Gln Thr Ser Pro Ala Gly Leu Lys Ala Val Leu
            820                 825                 830

Gln Leu Leu Val Glu Gly Ala Leu His Arg Gly Asn Thr Glu Leu Phe
        835                 840                 845

Gly Gly Gln Val Asp Gly Asp Asn Glu Thr Leu Ser Val Val Ser Ala
    850                 855                 860

Ser Leu Ala Ser Ala Ser Leu Leu Asp Thr Asn Arg Arg His Thr Ala
```

```
                865                 870                 875                 880

Ala Val Pro Gly Pro Gly Gly Ile Trp Ser Val Phe His Ala Gly Val
                    885                 890                 895

Ile Gly Arg Gly Leu Lys Pro Pro Lys Phe Val Gln Ser Arg Asn Gln
                900                 905                 910

Gln Glu Val Ile Tyr Asn Thr Gln Ser Leu Leu Ser Leu Leu Val His
            915                 920                 925

Cys Cys Ser Ala Pro Gly Gly Thr Glu Cys Gly Glu Cys Trp Gly Ala
        930                 935                 940

Pro Ile Leu Ser Pro Glu Ala Ala Lys Ala Val Ala Val Thr Leu Val
945                 950                 955                 960

Glu Ser Val Cys Pro Asp Ala Ala Gly Ala Glu Leu Ala Trp Pro Pro
                965                 970                 975

Glu Glu His Ala Arg Ala Thr Val Glu Arg Asp Leu Arg Ile Gly Arg
            980                 985                 990

Arg Phe Arg Glu Gln Pro Leu Leu  Phe Glu Leu Leu Lys  Leu Val Ala
        995                 1000                1005

Ala Ala  Pro Pro Ala Leu Cys  Tyr Cys Ser Val Leu  Leu Arg Gly
    1010                1015                1020

Leu Leu  Ala Ala Leu Leu Gly  His Trp Glu Ala Ser  Arg His Pro
    1025                1030                1035

Asp Thr  Thr His Ser Pro Trp  His Leu Glu Ala Ser  Cys Thr Leu
    1040                1045                1050

Val Ala  Val Met Ala Glu Gly  Ser Leu Leu Pro Pro  Ala Leu Gly
    1055                1060                1065

Asn Met  His Glu Val Phe Ser  Gln Leu Ala Pro Phe  Glu Val Arg
    1070                1075                1080

Leu Leu  Leu Leu Ser Val Trp  Gly Phe Leu Arg Glu  His Gly Pro
    1085                1090                1095

Leu Pro  Gln Lys Phe Ile Phe  Gln Ser Glu Arg Gly  Arg Phe Ile
    1100                1105                1110

Arg Asp  Phe Ser Arg Glu Gly  Gly Gly Glu Gly Gly  Pro His Leu
    1115                1120                1125

Ala Val  Leu His Ser Val Leu  His Arg Asn Ile Asp  Arg Leu Gly
    1130                1135                1140

Leu Phe  Ser Gly Arg Phe Gln  Ala Pro Ser Pro Ser  Thr Leu Leu
    1145                1150                1155

Arg Gln  Gly Thr
    1160

<210> SEQ ID NO 10
<211> LENGTH: 1162
<212> TYPE: PRT
<213> ORGANISM: Artificial
<220> FEATURE:
<223> OTHER INFORMATION: A variant of the human BFLP1698 polypeptide

<400> SEQUENCE: 10

Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
            20                  25                  30

Pro Leu Trp Asp Arg Gly Lys Ile Gly Lys Val Glu Gly His Gln His
        35                  40                  45

Ile Gln Asp Phe Ser Gln Lys Ser His Leu Pro Ser Ile Val Val Glu
```

-continued

```
            50                   55                   60
Ser Ser Glu Val Asn Glu Ser Gly Asp Leu His Leu Pro His Glu
 65                   70                   75                   80

Glu Leu Leu Leu Leu Thr Asp Gly Glu Glu Asp Ala Glu Ala Phe
                     85                   90                   95

Phe Gln Asp Gln Ser Glu Glu Pro Gly Ala Ala Arg Pro His His Gln
                100                  105                  110

Ala Arg Gln Val Glu His Ser Thr Gln Arg Gly His Leu Glu Ile Arg
                115                  120                  125

Glu Leu Lys Lys Lys Leu Phe Lys Arg Arg Val Leu Asn Arg Glu
130                  135                  140

Arg Arg Leu Arg His Arg Val Val Gly Ala Val Ile Asp Gln Gly Leu
145                  150                  155                  160

Ile Thr Arg His His Leu Lys Lys Arg Ala Ala Gln Glu Leu Ser Gln
                165                  170                  175

Glu Ile Lys Ala Phe Leu Thr Gly Val Asp Pro Ile Leu Gly His Gln
                180                  185                  190

Leu Ser Ala Arg Glu His Ala Arg Cys Gly Leu Leu Leu Leu Arg Ser
                195                  200                  205

Leu Pro Pro Ala Arg Ala Ala Val Leu Asp His Leu Arg Gly Val Phe
210                  215                  220

Asp Glu Ser Val Arg Ala His Leu Ala Ala Leu Asp Glu Thr Pro Val
225                  230                  235                  240

Ala Gly Pro Pro His Leu Arg Pro Pro Pro Ser His Val Pro Ala
                245                  250                  255

Gly Gly Pro Gly Leu Glu Asp Val Val Gln Glu Val Gln Gln Val Leu
                260                  265                  270

Ser Glu Phe Ile Arg Ala Asn Pro Lys Ala Trp Ala Pro Val Ile Ser
                275                  280                  285

Ala Trp Ser Ile Asp Leu Met Gly Gln Leu Ser Ser Thr Tyr Ser Gly
                290                  295                  300

Gln His Gln Arg Val Pro His Ala Thr Gly Ala Leu Asn Glu Leu Leu
305                  310                  315                  320

Gln Leu Trp Met Gly Cys Arg Ala Thr Arg Thr Leu Met Asp Ile Tyr
                325                  330                  335

Val Gln Cys Leu Ser Ala Leu Ile Gly Ser Cys Pro Asp Ala Cys Val
                340                  345                  350

Asp Ala Leu Leu Asp Thr Ser Val Gln His Ser Pro His Phe Asp Trp
                355                  360                  365

Val Val Ala His Ile Gly Ser Ser Phe Pro Gly Thr Ile Ile Ser Arg
                370                  375                  380

Val Leu Ser Cys Gly Leu Lys Asp Phe Cys Val His Gly Gly Ala Gly
385                  390                  395                  400

Gly Gly Ala Gly Ser Gly Gly Ser Ser Gln Thr Pro Ser Thr
                405                  410                  415

Asp Pro Phe Pro Gly Ser Pro Ala Ile Pro Ala Glu Lys Arg Val Pro
                420                  425                  430

Lys Ile Ala Ser Val Val Gly Ile Leu Gly His Leu Ala Ser Arg His
                435                  440                  445

Gly Asp Ser Ile Arg Arg Glu Leu Leu Arg Met Phe His Asp Ser Leu
                450                  455                  460

Ala Gly Gly Ser Gly Gly Arg Ser Gly Asp Pro Ser Leu Gln Ala Thr
465                  470                  475                  480
```

```
Val Pro Phe Leu Leu Gln Leu Ala Val Met Ser Pro Ala Leu Leu Gly
                485                 490                 495

Thr Val Ser Gly Glu Leu Val Asp Cys Leu Lys Pro Ala Val Leu
            500                 505                 510

Ser Gln Leu Gln Gln His Leu Gln Gly Phe Pro Arg Glu Glu Leu Asp
            515                 520                 525

Asn Met Leu Asn Leu Ala Val His Leu Val Ser Gln Ala Ser Gly Ala
    530                 535                 540

Gly Ala Tyr Arg Leu Leu Gln Phe Leu Val Asp Thr Ala Met Pro Ala
545                 550                 555                 560

Ser Val Ile Thr Thr Gln Gly Leu Ala Val Pro Asp Thr Val Arg Glu
                565                 570                 575

Ala Cys Asp Arg Leu Ile Gln Leu Leu Leu His Leu Gln Lys Leu
            580                 585                 590

Val His His Arg Gly Gly Ser Pro Gly Glu Gly Val Leu Gly Pro Pro
            595                 600                 605

Pro Pro Pro Arg Leu Val Pro Phe Leu Asp Ala Leu Lys Asn His Val
        610                 615                 620

Gly Glu Leu Cys Gly Glu Thr Leu Arg Leu Glu Arg Lys Arg Phe Leu
625                 630                 635                 640

Trp Gln His Gln Leu Leu Gly Leu Leu Ser Val Tyr Thr Arg Pro Ser
                645                 650                 655

Cys Gly Pro Glu Ala Leu Gly His Leu Leu Ser Arg Ala Arg Ser Pro
            660                 665                 670

Glu Glu Leu Ser Leu Ala Thr Gln Leu Tyr Ala Gly Leu Val Val Ser
            675                 680                 685

Leu Ser Gly Leu Leu Pro Leu Ala Phe Arg Ser Cys Leu Ala Arg Val
        690                 695                 700

His Ala Gly Thr Leu Gln Pro Pro Phe Thr Ala Arg Phe Leu Arg Asn
705                 710                 715                 720

Leu Ala Leu Leu Val Gly Trp Glu Gln Gln Gly Gly Asp Gly Pro Ala
                725                 730                 735

Ala Leu Gly Ala His Phe Gly Glu Ser Ala Ser Ala His Leu Ser Asp
            740                 745                 750

Leu Ala Pro Leu Leu His Pro Glu Glu Val Ala Glu Ala Ala
        755                 760                 765

Ala Ser Leu Leu Ala Ile Cys Pro Phe Pro Ser Glu Ala Leu Ser Pro
        770                 775                 780

Ser Gln Leu Leu Gly Leu Val Arg Ala Gly Val His Arg Phe Phe Ala
785                 790                 795                 800

Ser Leu Arg Leu His Gly Pro Pro Gly Val Ala Ser Ala Cys Gln Leu
            805                 810                 815

Leu Thr Arg Leu Ser Gln Thr Ser Pro Ala Gly Leu Lys Ala Val Leu
        820                 825                 830

Gln Leu Leu Val Glu Gly Ala Leu His Arg Gly Asn Thr Glu Leu Phe
        835                 840                 845

Gly Gly Gln Val Asp Gly Asp Asn Glu Thr Leu Ser Val Val Ser Ala
850                 855                 860

Ser Leu Ala Ser Ala Ser Leu Leu Asp Thr Asn Arg Arg His Thr Ala
865                 870                 875                 880

Ala Val Pro Gly Pro Gly Gly Ile Trp Ser Val Phe His Ala Gly Val
            885                 890                 895
```

```
Ile Gly Arg Gly Leu Lys Pro Pro Lys Phe Val Gln Ser Arg Asn Gln
            900                 905                 910

Gln Glu Val Ile Tyr Asn Thr Gln Ser Leu Leu Ser Leu Leu Val His
            915                 920                 925

Cys Cys Ser Ala Pro Gly Gly Thr Glu Cys Gly Glu Cys Trp Gly Ala
            930                 935                 940

Pro Ile Leu Ser Pro Glu Ala Ala Lys Ala Val Ala Val Thr Leu Val
945                 950                 955                 960

Glu Ser Val Cys Pro Asp Ala Ala Gly Ala Glu Leu Ala Trp Pro Pro
                965                 970                 975

Glu Glu His Ala Arg Ala Thr Val Glu Arg Asp Leu Arg Ile Gly Arg
            980                 985                 990

Arg Phe Arg Glu Gln Pro Leu Leu Phe Glu Leu Leu Lys Leu Val Ala
            995                 1000                1005

Ala Ala Pro Pro Ala Leu Cys Tyr Cys Ser Val Leu Leu Arg Gly
    1010                1015                1020

Leu Leu Ala Ala Leu Leu Gly His Trp Glu Ala Ser Arg His Pro
    1025                1030                1035

Asp Thr Thr His Ser Pro Trp His Leu Glu Ala Ser Cys Thr Leu
    1040                1045                1050

Val Ala Val Met Ala Glu Gly Ser Leu Leu Pro Pro Ala Leu Gly
    1055                1060                1065

Asn Met His Glu Val Phe Ser Gln Leu Ala Pro Phe Glu Val Arg
    1070                1075                1080

Leu Leu Leu Leu Ser Val Trp Gly Phe Leu Arg Glu His Gly Pro
    1085                1090                1095

Leu Pro Gln Lys Phe Ile Phe Gln Ser Glu Arg Gly Arg Phe Ile
    1100                1105                1110

Arg Asp Phe Ser Arg Glu Gly Gly Gly Glu Gly Gly Pro His Leu
    1115                1120                1125

Ala Val Leu His Ser Val Leu His Arg Asn Ile Asp Arg Leu Gly
    1130                1135                1140

Leu Phe Ser Gly Arg Phe Gln Ala Pro Ser Pro Ser Thr Leu Leu
    1145                1150                1155

Arg Gln Gly Thr
    1160

<210> SEQ ID NO 11
<211> LENGTH: 1162
<212> TYPE: PRT
<213> ORGANISM: Artificial
<220> FEATURE:
<223> OTHER INFORMATION: A variant of the human BFLP1698 polypeptide

<400> SEQUENCE: 11

Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
            20                  25                  30

Pro Leu Trp Asp Arg Gly Lys Ile Gly Lys Val Glu Gly His Gln His
        35                  40                  45

Ile Gln Asp Phe Ser Gln Lys Ser His Leu Pro Ser Ile Val Val Glu
    50                  55                  60

Ser Ser Glu Val Asn Glu Glu Ser Gly Asp Leu His Leu Pro His Glu
65                  70                  75                  80
```

-continued

```
Glu Leu Leu Leu Leu Thr Asp Gly Glu Glu Asp Ala Glu Ala Phe
                 85                  90                  95

Phe Gln Asp Gln Ser Glu Pro Gly Ala Ala Arg Pro His His Gln
            100                 105                 110

Ala Arg Gln Val Glu His Ser Thr Gln Arg Gly His Leu Glu Ile Arg
            115                 120                 125

Glu Leu Lys Lys Lys Leu Phe Lys Arg Arg Val Leu Asn Arg Glu
        130                 135                 140

Arg Arg Leu Arg His Arg Val Val Gly Ala Val Ile Asp Gln Gly Leu
145                 150                 155                 160

Ile Thr Arg His His Leu Lys Lys Arg Ala Ala Gln Glu Leu Ser Gln
                165                 170                 175

Glu Ile Lys Ala Phe Leu Thr Gly Val Asp Pro Ile Leu Gly His Gln
            180                 185                 190

Leu Ser Ala Arg Glu His Ala Arg Cys Gly Leu Leu Leu Arg Ser
            195                 200                 205

Leu Pro Pro Ala Arg Ala Ala Val Leu Asp His Leu Arg Gly Val Phe
    210                 215                 220

Asp Glu Ser Val Arg Ala His Leu Ala Ala Leu Asp Glu Thr Pro Val
225                 230                 235                 240

Ala Gly Pro Pro His Leu Arg Pro Pro Pro Ser His Val Pro Ala
            245                 250                 255

Gly Gly Pro Gly Leu Glu Asp Val Val Gln Glu Val Gln Gln Val Leu
            260                 265                 270

Ser Glu Phe Ile Arg Ala Asn Pro Lys Ala Trp Ala Pro Val Ile Ser
        275                 280                 285

Ala Trp Ser Ile Asp Leu Met Gly Gln Leu Ser Thr Tyr Ser Gly
    290                 295                 300

Gln His Gln Arg Val Pro His Ala Thr Gly Ala Leu Asn Glu Leu Leu
305                 310                 315                 320

Gln Leu Trp Met Gly Cys Arg Ala Thr Arg Thr Leu Met Asp Ile Tyr
            325                 330                 335

Val Gln Cys Leu Ser Ala Leu Ile Gly Ser Cys Pro Asp Ala Cys Val
            340                 345                 350

Asp Ala Leu Leu Asp Thr Ser Val Gln His Ser Pro His Phe Asp Trp
        355                 360                 365

Val Val Ala His Ile Gly Ser Ser Phe Pro Gly Thr Ile Ile Ser Arg
    370                 375                 380

Val Leu Ser Cys Gly Leu Lys Asp Phe Cys Val His Gly Gly Ala Gly
385                 390                 395                 400

Gly Gly Ala Gly Ser Ser Gly Ser Ser Ser Gln Thr Pro Ser Thr
            405                 410                 415

Asp Pro Phe Pro Gly Ser Pro Ala Ile Pro Ala Glu Lys Arg Val Pro
            420                 425                 430

Lys Ile Ala Ser Val Val Gly Ile Leu Gly His Leu Ala Ser Arg His
        435                 440                 445

Gly Asp Ser Ile Arg Arg Glu Leu Leu Arg Met Phe His Asp Ser Leu
    450                 455                 460

Ala Gly Gly Ser Gly Gly Arg Ser Gly Asp Pro Ser Leu Gln Ala Thr
465                 470                 475                 480

Val Pro Phe Leu Leu Gln Leu Ala Val Met Ser Pro Ala Leu Leu Gly
            485                 490                 495

Thr Val Ser Gly Glu Leu Val Asp Cys Leu Lys Pro Pro Ala Val Leu
```

-continued

```
                500                 505                 510
Ser Gln Leu Gln Gln His Leu Gln Gly Phe Pro Arg Glu Leu Asp
        515                 520                 525

Asn Met Leu Asn Leu Ala Val His Leu Val Ser Gln Ala Ser Gly Ala
        530                 535                 540

Gly Ala Tyr Arg Leu Leu Gln Phe Leu Val Asp Thr Ala Met Pro Ala
545                 550                 555                 560

Ser Val Ile Thr Thr Gln Gly Leu Ala Val Pro Asp Thr Val Arg Glu
                565                 570                 575

Ala Cys Asp Arg Leu Ile Gln Leu Leu Leu His Leu Gln Lys Leu
            580                 585                 590

Val His His Arg Gly Gly Ser Pro Gly Glu Gly Val Leu Gly Pro Pro
            595                 600                 605

Pro Pro Pro Arg Leu Val Pro Phe Leu Asp Ala Leu Lys Asn His Val
        610                 615                 620

Gly Glu Leu Cys Gly Glu Thr Leu Arg Leu Glu Arg Lys Arg Phe Leu
625                 630                 635                 640

Trp Gln His Gln Leu Leu Gly Leu Leu Ser Val Tyr Thr Arg Pro Ser
            645                 650                 655

Cys Gly Pro Glu Ala Leu Gly His Leu Leu Ser Arg Ala Arg Ser Pro
            660                 665                 670

Glu Glu Leu Ser Leu Ala Thr Gln Leu Tyr Ala Gly Leu Val Val Ser
        675                 680                 685

Leu Ser Gly Leu Leu Pro Leu Ala Phe Arg Ser Cys Leu Ala Arg Val
        690                 695                 700

His Ala Gly Thr Leu Gln Pro Pro Phe Thr Ala Arg Phe Leu Arg Asn
705                 710                 715                 720

Leu Ala Leu Leu Val Gly Trp Glu Gln Gln Gly Gly Glu Gly Pro Ala
                725                 730                 735

Ala Leu Gly Ala His Phe Gly Glu Ser Ala Ser Ala His Leu Ser Asp
            740                 745                 750

Leu Ala Pro Leu Leu Leu His Pro Glu Glu Glu Val Ala Glu Ala Ala
        755                 760                 765

Ala Ser Leu Leu Ala Ile Cys Pro Phe Pro Ser Glu Ala Leu Ser Pro
770                 775                 780

Ser Gln Leu Leu Gly Leu Val Arg Ala Gly Val His Arg Phe Phe Ala
785                 790                 795                 800

Ser Leu Arg Leu His Gly Pro Pro Gly Val Ala Ser Ala Cys Gln Leu
                805                 810                 815

Leu Thr Arg Leu Ser Gln Thr Ser Pro Ala Gly Leu Lys Ala Val Leu
            820                 825                 830

Gln Leu Leu Val Glu Gly Ala Leu His Arg Gly Asn Thr Glu Leu Phe
        835                 840                 845

Gly Gly Gln Val Asp Gly Asp Asn Glu Ala Leu Ser Val Val Ser Ala
        850                 855                 860

Ser Leu Ala Ser Ala Ser Leu Leu Asp Thr Asn Arg Arg His Thr Ala
865                 870                 875                 880

Ala Val Pro Gly Pro Gly Gly Ile Trp Ser Val Phe His Ala Gly Val
                885                 890                 895

Ile Gly Arg Gly Leu Lys Pro Pro Lys Phe Val Gln Ser Arg Asn Gln
            900                 905                 910

Gln Glu Val Ile Tyr Asn Thr Gln Ser Leu Leu Ser Leu Leu Val His
        915                 920                 925
```

Cys Cys Ser Ala Pro Gly Gly Thr Glu Cys Gly Glu Cys Trp Gly Ala
    930                 935                 940

Pro Ile Leu Ser Pro Glu Ala Ala Lys Ala Val Ala Val Thr Leu Val
945                 950                 955                 960

Glu Ser Val Cys Pro Asp Ala Ala Gly Ala Glu Leu Ala Trp Pro Pro
                965                 970                 975

Glu Glu His Ala Arg Ala Thr Val Glu Arg Asp Leu Arg Ile Gly Arg
            980                 985                 990

Arg Phe Arg Glu Gln Pro Leu Leu Phe Glu Leu Leu Lys Leu Val Ala
        995                 1000                1005

Ala Ala Pro Pro Ala Leu Cys Tyr Cys Ser Val Leu Leu Arg Gly
    1010                1015                1020

Leu Leu Ala Ala Leu Leu Gly His Trp Glu Ala Ser Arg His Pro
    1025                1030                1035

Asp Thr Thr His Ser Pro Trp His Leu Glu Ala Ser Cys Thr Leu
    1040                1045                1050

Val Ala Val Met Ala Glu Gly Ser Leu Leu Pro Pro Ala Leu Gly
    1055                1060                1065

Asn Met His Glu Val Phe Ser Gln Leu Ala Pro Phe Glu Val Arg
    1070                1075                1080

Leu Leu Leu Ser Val Trp Gly Phe Leu Arg Glu His Gly Pro
    1085                1090                1095

Leu Pro Gln Lys Phe Ile Phe Gln Ser Glu Arg Gly Arg Phe Ile
    1100                1105                1110

Arg Asp Phe Ser Arg Glu Gly Gly Glu Gly Gly Pro His Leu
    1115                1120                1125

Ala Val Leu His Ser Val Leu His Arg Asn Ile Asp Arg Leu Gly
    1130                1135                1140

Leu Phe Ser Gly Arg Phe Gln Ala Pro Ser Pro Ser Thr Leu Leu
    1145                1150                1155

Arg Gln Gly Thr
    1160

<210> SEQ ID NO 12
<211> LENGTH: 1162
<212> TYPE: PRT
<213> ORGANISM: Artificial
<220> FEATURE:
<223> OTHER INFORMATION: A variant of the human BFLP1698 polypeptide

<400> SEQUENCE: 12

Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
                20                  25                  30

Pro Leu Trp Asp Arg Gly Lys Ile Gly Lys Val Glu Gly His Gln His
            35                  40                  45

Ile Gln Asp Phe Ser Gln Lys Ser His Leu Pro Ser Ile Val Val Glu
    50                  55                  60

Ser Ser Glu Val Asn Glu Glu Ser Gly Asp Leu His Leu Pro His Glu
65                  70                  75                  80

Glu Leu Leu Leu Leu Thr Asp Gly Glu Glu Glu Asp Ala Glu Ala Phe
                85                  90                  95

Phe Gln Asp Gln Ser Glu Glu Pro Gly Ala Ala Arg Pro His His Gln
                100                 105                 110

```
Ala Arg Gln Val Glu His Ser Thr Gln Arg Gly His Leu Glu Ile Arg
        115                 120                 125

Glu Leu Lys Lys Lys Leu Phe Lys Arg Arg Val Leu Asn Arg Glu
    130                 135                 140

Arg Arg Leu Arg His Arg Val Val Gly Ala Val Ile Asp Gln Gly Leu
145                 150                 155                 160

Ile Thr Arg His His Leu Lys Lys Arg Ala Ala Gln Glu Leu Ser Gln
                165                 170                 175

Glu Ile Lys Ala Phe Leu Thr Gly Val Asp Pro Ile Leu Gly His Gln
            180                 185                 190

Leu Ser Ala Arg Glu His Ala Arg Cys Gly Leu Leu Leu Leu Arg Ser
        195                 200                 205

Leu Pro Pro Ala Arg Ala Ala Val Leu Asp His Leu Arg Gly Val Phe
    210                 215                 220

Asp Glu Ser Val Arg Ala His Leu Ala Ala Leu Asp Glu Thr Pro Val
225                 230                 235                 240

Ala Gly Pro Pro His Leu Arg Pro Pro Pro Ser His Val Pro Ala
                245                 250                 255

Gly Gly Pro Gly Leu Glu Asp Val Val Gln Glu Val Gln Gln Val Leu
            260                 265                 270

Ser Glu Phe Ile Arg Ala Asn Pro Lys Ala Trp Ala Pro Val Ile Ser
        275                 280                 285

Ala Trp Ser Ile Asp Leu Met Gly Gln Leu Ser Ser Thr Tyr Ser Gly
    290                 295                 300

Gln His Gln Arg Val Pro His Ala Thr Gly Ala Leu Asn Glu Leu Leu
305                 310                 315                 320

Gln Leu Trp Met Gly Cys Arg Ala Thr Arg Thr Leu Met Asp Ile Tyr
                325                 330                 335

Val Gln Cys Leu Ser Ala Leu Ile Gly Ser Cys Pro Asp Ala Cys Val
            340                 345                 350

Asp Ala Leu Leu Asp Thr Ser Val Gln His Ser Pro His Phe Asp Trp
        355                 360                 365

Val Val Ala His Ile Gly Ser Ser Phe Pro Gly Thr Ile Ile Ser Arg
    370                 375                 380

Val Leu Ser Cys Gly Leu Lys Asp Phe Cys Val His Gly Gly Ala Gly
385                 390                 395                 400

Gly Gly Ala Gly Ser Ser Gly Gly Ser Ser Gln Thr Pro Ser Thr
                405                 410                 415

Asp Pro Phe Pro Gly Ser Pro Ala Ile Pro Ala Glu Lys Arg Val Pro
            420                 425                 430

Lys Ile Ala Ser Val Val Gly Ile Leu Gly His Leu Ala Ser Arg His
        435                 440                 445

Gly Asp Ser Ile Arg Arg Glu Leu Leu Arg Met Phe His Asp Ser Leu
    450                 455                 460

Ala Gly Gly Ser Gly Gly Arg Ser Gly Asp Pro Ser Leu Gln Ala Thr
465                 470                 475                 480

Val Pro Phe Leu Leu Gln Leu Ala Val Met Ser Pro Ala Leu Leu Gly
                485                 490                 495

Thr Val Ser Gly Glu Leu Val Asp Cys Leu Lys Pro Pro Ala Val Leu
            500                 505                 510

Ser Gln Leu Gln Gln His Leu Gln Gly Phe Pro Arg Glu Glu Leu Asp
        515                 520                 525
```

```
Asn Met Leu Asn Leu Ala Val His Leu Val Ser Gln Ala Ser Gly Ala
    530                 535                 540

Gly Ala Tyr Arg Leu Leu Gln Phe Leu Val Asp Thr Ala Met Pro Ala
545                 550                 555                 560

Ser Val Ile Thr Thr Gln Gly Leu Ala Val Pro Asp Thr Val Arg Glu
                565                 570                 575

Ala Cys Asp Arg Leu Ile Gln Leu Leu Leu His Leu Gln Lys Leu
                580                 585                 590

Val His His Arg Gly Gly Ser Pro Gly Glu Gly Val Leu Gly Pro Pro
            595                 600                 605

Pro Pro Pro Arg Leu Val Pro Phe Leu Asp Ala Leu Lys Asn His Val
    610                 615                 620

Gly Glu Leu Cys Gly Glu Thr Leu Arg Leu Glu Arg Lys Arg Phe Leu
625                 630                 635                 640

Trp Gln His Gln Leu Leu Gly Leu Leu Ser Val Tyr Thr Arg Pro Ser
                645                 650                 655

Cys Gly Pro Glu Ala Leu Gly His Leu Leu Ser Arg Ala Arg Ser Pro
                660                 665                 670

Glu Glu Leu Ser Leu Ala Thr Gln Leu Tyr Ala Gly Leu Val Val Ser
            675                 680                 685

Leu Ser Gly Leu Leu Pro Leu Ala Phe Arg Ser Cys Leu Ala Arg Val
    690                 695                 700

His Ala Gly Thr Leu Gln Pro Pro Phe Thr Ala Arg Phe Leu Arg Asn
705                 710                 715                 720

Leu Ala Leu Leu Val Gly Trp Glu Gln Gln Gly Gly Glu Gly Pro Ala
                725                 730                 735

Ala Leu Gly Ala His Phe Gly Ser Ala Ser Ala His Leu Ser Asp
                740                 745                 750

Leu Ala Pro Leu Leu Leu His Pro Glu Glu Val Ala Glu Ala Ala
            755                 760                 765

Ala Ser Leu Leu Ala Ile Cys Pro Phe Pro Ser Glu Ala Leu Ser Pro
    770                 775                 780

Ser Gln Leu Leu Gly Leu Val Arg Ala Gly Val His Arg Phe Phe Ala
785                 790                 795                 800

Ser Leu Arg Leu His Gly Pro Pro Gly Val Ala Ser Ala Cys Gln Leu
                805                 810                 815

Leu Thr Arg Leu Ser Gln Thr Ser Pro Ala Gly Leu Lys Ala Val Leu
                820                 825                 830

Gln Leu Leu Val Glu Gly Ala Leu His Arg Gly Asn Thr Glu Leu Phe
            835                 840                 845

Gly Gly Gln Val Asp Gly Asp Asn Glu Thr Leu Ser Val Val Ser Ala
    850                 855                 860

Ser Leu Ala Ser Ala Ser Leu Leu Asp Thr Asn Arg Arg His Thr Ala
865                 870                 875                 880

Ala Val Pro Gly Pro Gly Gly Ile Trp Ser Val Phe His Ala Gly Val
                885                 890                 895

Ile Gly Arg Gly Leu Lys Pro Pro Lys Phe Val Gln Ser Arg Asn Gln
                900                 905                 910

Gln Glu Val Ile Tyr Asn Thr Gln Ser Leu Leu Ser Leu Leu Val His
            915                 920                 925

Cys Cys Ser Ala Pro Gly Gly Thr Glu Cys Gly Glu Cys Trp Gly Ala
    930                 935                 940

Pro Ile Leu Ser Pro Glu Ala Ala Lys Ala Val Ala Val Thr Leu Val
```

-continued

```
              945                 950                 955                 960
Glu Ser Val Cys Pro Asp Ala Ala Gly Ala Glu Leu Ala His Pro Pro
                965                 970                 975
Glu Glu His Ala Arg Ala Thr Val Glu Arg Asp Leu Arg Ile Gly Arg
                980                 985                 990
Arg Phe Arg Glu Gln Pro Leu Leu  Phe Glu Leu Leu Lys  Leu Val Ala
            995                1000                1005
Ala Ala  Pro Pro Ala Leu Cys  Tyr Cys Ser Val Leu  Leu Arg Gly
           1010                1015                1020
Leu Leu  Ala Ala Leu Leu Gly  His Trp Glu Ala Ser  Arg His Pro
           1025                1030                1035
Asp Thr  Thr His Ser Pro Trp  His Leu Glu Ala Ser  Cys Thr Leu
           1040                1045                1050
Val Ala  Val Met Ala Glu Gly  Ser Leu Leu Pro Pro  Ala Leu Gly
           1055                1060                1065
Asn Met  His Glu Val Phe Ser  Gln Leu Ala Pro Phe  Glu Val Arg
           1070                1075                1080
Leu Leu  Leu Leu Ser Val Trp  Gly Phe Leu Arg Glu  His Gly Pro
           1085                1090                1095
Leu Pro  Gln Lys Phe Ile Phe  Gln Ser Glu Arg Gly  Arg Phe Ile
           1100                1105                1110
Arg Asp  Phe Ser Arg Glu Gly  Gly Gly Glu Gly Gly  Pro His Leu
           1115                1120                1125
Ala Val  Leu His Ser Val Leu  His Arg Asn Ile Asp  Arg Leu Gly
           1130                1135                1140
Leu Phe  Ser Gly Arg Phe Gln  Ala Pro Ser Pro Ser  Thr Leu Leu
           1145                1150                1155
Arg Gln  Gly Thr
           1160

<210> SEQ ID NO 13
<211> LENGTH: 1162
<212> TYPE: PRT
<213> ORGANISM: Artificial
<220> FEATURE:
<223> OTHER INFORMATION: A variant of the human BFLP1698 polypeptide

<400> SEQUENCE: 13

Met Ala Leu Val Pro Gly Arg Ser Lys Glu Asp Gly Leu Trp Thr Arg
1               5                  10                  15
Asn Ser Pro Gly Ser Ser Gln His Pro Glu Ser Pro Arg Leu Pro Asn
                20                  25                  30
Pro Leu Trp Asp Arg Gly Lys Ile Gly Lys Val Glu Gly His Gln His
            35                  40                  45
Ile Gln Asp Phe Ser Gln Lys Ser His Leu Pro Ser Ile Val Val Glu
        50                  55                  60
Ser Ser Glu Val Asn Glu Glu Ser Gly Asp Leu His Leu Pro His Glu
65                  70                  75                  80
Glu Leu Leu Leu Leu Thr Asp Gly Glu Glu Glu Asp Ala Glu Ala Phe
                85                  90                  95
Phe Gln Asp Gln Ser Glu Glu Pro Gly Ala Ala Arg Pro His His Gln
                100                 105                 110
Ala Arg Gln Val Glu His Ser Thr Gln Arg Gly His Leu Glu Ile Arg
            115                 120                 125
Glu Leu Lys Lys Lys Leu Phe Lys Arg Arg Arg Val Leu Asn Arg Glu
```

-continued

```
            130                 135                 140
Arg Arg Leu Arg His Arg Val Val Gly Ala Val Ile Asp Gln Gly Leu
145                 150                 155                 160

Ile Thr Arg His His Leu Lys Lys Arg Ala Ala Gln Glu Leu Ser Gln
                165                 170                 175

Glu Ile Lys Ala Phe Leu Thr Gly Val Asp Pro Ile Leu Gly His Gln
            180                 185                 190

Leu Ser Ala Arg Glu His Ala Arg Cys Gly Leu Leu Leu Leu Arg Ser
                195                 200                 205

Leu Pro Pro Ala Arg Ala Val Leu Asp His Leu Arg Gly Val Phe
210                 215                 220

Asp Glu Ser Val Arg Ala His Leu Ala Ala Leu Asp Glu Thr Pro Val
225                 230                 235                 240

Ala Gly Pro Pro His Leu Arg Pro Pro Pro Ser His Val Pro Ala
                245                 250                 255

Gly Gly Pro Gly Leu Glu Asp Val Val Gln Glu Val Gln Val Leu
                260                 265                 270

Ser Glu Phe Ile Arg Ala Asn Pro Lys Ala Trp Ala Pro Val Ile Ser
            275                 280                 285

Ala Trp Ser Ile Asp Leu Met Gly Gln Leu Ser Ser Thr Tyr Ser Gly
            290                 295                 300

Gln His Gln Arg Val Pro His Ala Thr Gly Ala Leu Asn Glu Leu Leu
305                 310                 315                 320

Gln Leu Trp Met Gly Cys Arg Ala Thr Arg Thr Leu Met Asp Ile Tyr
                325                 330                 335

Val Gln Cys Leu Ser Ala Leu Ile Gly Ser Cys Pro Asp Ala Cys Val
            340                 345                 350

Asp Ala Leu Leu Asp Thr Ser Val Gln His Ser Pro His Phe Asp Trp
                355                 360                 365

Val Val Ala His Ile Gly Ser Ser Phe Pro Gly Thr Ile Ile Ser Arg
            370                 375                 380

Val Leu Ser Cys Gly Leu Lys Asp Phe Cys Val His Gly Gly Ala Gly
385                 390                 395                 400

Gly Gly Ala Gly Ser Ser Gly Gly Ser Ser Gln Thr Pro Ser Thr
                405                 410                 415

Asp Pro Phe Pro Gly Ser Pro Ala Ile Pro Ala Glu Lys Arg Val Pro
            420                 425                 430

Lys Ile Ala Ser Val Val Gly Ile Leu Gly His Leu Ala Ser Arg His
                435                 440                 445

Gly Asp Ser Ile Arg Arg Glu Leu Leu Arg Met Phe His Asp Ser Leu
450                 455                 460

Ala Gly Gly Ser Gly Gly Arg Ser Gly Asp Pro Ser Leu Gln Ala Thr
465                 470                 475                 480

Val Pro Phe Leu Leu Gln Leu Ala Val Met Ser Pro Ala Leu Leu Gly
                485                 490                 495

Thr Val Ser Gly Glu Leu Val Asp Cys Leu Lys Pro Pro Ala Val Leu
                500                 505                 510

Ser Gln Leu Gln Gln His Leu Gln Gly Phe Pro Arg Glu Glu Leu Asp
                515                 520                 525

Asn Met Leu Asn Leu Ala Val His Leu Val Ser Gln Ala Ser Gly Ala
                530                 535                 540

Gly Ala Tyr Arg Leu Leu Gln Phe Leu Val Asp Thr Ala Met Pro Ala
545                 550                 555                 560
```

-continued

```
Ser Val Ile Thr Thr Gln Gly Leu Ala Val Pro Asp Thr Val Arg Glu
            565                 570                 575
Ala Cys Asp Arg Leu Ile Gln Leu Leu Leu His Leu Gln Lys Leu
        580                 585                 590
Val His His Arg Gly Gly Ser Pro Gly Glu Gly Val Leu Gly Pro Pro
        595                 600                 605
Pro Pro Pro Arg Leu Val Pro Phe Leu Asp Ala Leu Lys Asn His Val
        610                 615                 620
Gly Glu Leu Cys Gly Glu Thr Leu Arg Leu Glu Arg Lys Arg Phe Leu
625                 630                 635                 640
Trp Gln His Gln Leu Leu Gly Leu Leu Ser Val Tyr Thr Arg Pro Ser
                645                 650                 655
Cys Gly Pro Glu Ala Leu Gly His Leu Leu Ser Arg Ala Arg Ser Pro
                660                 665                 670
Glu Glu Leu Ser Leu Ala Thr Gln Leu Tyr Ala Gly Leu Val Val Ser
            675                 680                 685
Leu Ser Gly Leu Leu Pro Leu Ala Phe Arg Ser Cys Leu Ala Arg Val
    690                 695                 700
His Ala Gly Thr Leu Gln Pro Pro Phe Thr Ala Arg Phe Leu Arg Asn
705                 710                 715                 720
Leu Ala Leu Leu Val Gly Trp Glu Gln Gln Gly Gly Glu Gly Pro Ala
                725                 730                 735
Ala Leu Gly Ala His Phe Gly Glu Ser Ala Ser Ala His Leu Ser Asp
                740                 745                 750
Leu Ala Pro Leu Leu His Pro Glu Glu Val Ala Glu Ala Ala
            755                 760                 765
Ala Ser Leu Leu Ala Ile Cys Pro Phe Pro Ser Glu Ala Leu Ser Pro
        770                 775                 780
Ser Gln Leu Leu Gly Leu Val Arg Ala Gly Val His Arg Phe Phe Ala
785                 790                 795                 800
Ser Leu Arg Leu His Gly Pro Pro Gly Val Ala Ser Ala Cys Gln Leu
                805                 810                 815
Leu Thr Arg Leu Ser Gln Thr Ser Pro Ala Gly Leu Lys Ala Val Leu
                820                 825                 830
Gln Leu Leu Val Glu Gly Ala Leu His Arg Gly Asn Thr Glu Leu Phe
            835                 840                 845
Gly Gly Gln Val Asp Gly Asp Asn Glu Thr Leu Ser Val Val Ser Ala
850                 855                 860
Ser Leu Ala Ser Ala Ser Leu Leu Asp Thr Asn Arg Arg His Thr Ala
865                 870                 875                 880
Ala Val Pro Gly Pro Gly Gly Ile Trp Ser Val Phe His Ala Gly Val
                885                 890                 895
Ile Gly Arg Gly Leu Lys Pro Pro Lys Phe Val Gln Ser Arg Asn Gln
                900                 905                 910
Gln Glu Val Ile Tyr Asn Thr Gln Ser Leu Leu Ser Leu Leu Val His
            915                 920                 925
Cys Cys Ser Ala Pro Gly Gly Thr Glu Cys Gly Glu Cys Trp Gly Ala
        930                 935                 940
Pro Ile Leu Ser Pro Glu Ala Ala Lys Ala Val Ala Val Thr Leu Val
945                 950                 955                 960
Glu Ser Val Cys Pro Asp Ala Ala Gly Ala Glu Leu Ala Trp Pro Pro
                965                 970                 975
```

-continued

```
Glu Glu His Ala Arg Ala Thr Val Glu Arg Asp Leu Arg Ile Gly Arg
            980                 985                 990

Arg Phe Arg Glu Gln Pro Leu Leu Phe Glu Leu Leu Lys Leu Val Ala
        995                1000                1005

Ala Ala Pro Pro Ala Leu Cys Tyr Cys Ser Val Leu Leu Arg Gly
    1010                1015                1020

Leu Leu Ala Ala Leu Leu Gly His Trp Glu Ala Ser Arg His Thr
    1025                1030                1035

Asp Thr Thr His Ser Pro Trp His Leu Glu Ala Ser Cys Thr Leu
    1040                1045                1050

Val Ala Val Met Ala Glu Gly Ser Leu Pro Pro Ala Leu Gly
    1055                1060                1065

Asn Met His Glu Val Phe Ser Gln Leu Ala Pro Phe Glu Val Arg
    1070                1075                1080

Leu Leu Leu Leu Ser Val Trp Gly Phe Leu Arg Glu His Gly Pro
    1085                1090                1095

Leu Pro Gln Lys Phe Ile Phe Gln Ser Glu Arg Gly Arg Phe Ile
    1100                1105                1110

Arg Asp Phe Ser Arg Glu Gly Gly Glu Gly Gly Pro His Leu
    1115                1120                1125

Ala Val Leu His Ser Val Leu His Arg Asn Ile Asp Arg Leu Gly
    1130                1135                1140

Leu Phe Ser Gly Arg Phe Gln Ala Pro Ser Pro Ser Thr Leu Leu
    1145                1150                1155

Arg Gln Gly Thr
    1160

<210> SEQ ID NO 14
<211> LENGTH: 1162
<212> TYPE: PRT
<213> ORGANISM: Artificial
<220> FEATURE:
<223> OTHER INFORMATION: A variant of the human BFLP1698 polypeptide

<400> SEQUENCE: 14

Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
            20                  25                  30

Pro Leu Trp Asp Arg Gly Lys Ile Gly Lys Val Glu Gly His Gln His
        35                  40                  45

Ile Gln Asp Phe Ser Gln Lys Ser His Leu Pro Ser Ile Val Val Glu
    50                  55                  60

Ser Ser Glu Val Asn Glu Glu Ser Gly Asp Leu His Leu Pro His Glu
65                  70                  75                  80

Glu Leu Leu Leu Leu Thr Asp Gly Glu Glu Asp Ala Glu Ala Phe
            85                  90                  95

Phe Gln Asp Gln Ser Glu Glu Pro Gly Ala Ala Arg Pro His His Gln
            100                 105                 110

Ala Arg Gln Val Glu His Ser Thr Gln Arg Gly His Leu Glu Ile Arg
        115                 120                 125

Glu Leu Lys Lys Lys Leu Phe Lys Arg Arg Val Leu Asn Arg Glu
    130                 135                 140

Arg Arg Leu Arg His Arg Val Val Gly Ala Val Ile Asp Gln Gly Leu
145                 150                 155                 160
```

-continued

```
Ile Thr Arg His His Leu Lys Lys Arg Ala Ala Gln Glu Leu Ser Gln
                165                 170                 175

Glu Ile Lys Ala Phe Leu Thr Gly Val Asp Pro Ile Leu Gly His Gln
            180                 185                 190

Leu Ser Ala Arg Glu His Ala Arg Cys Gly Leu Leu Leu Arg Ser
        195                 200                 205

Leu Pro Pro Ala Arg Ala Ala Val Leu Asp His Leu Arg Gly Val Phe
    210                 215                 220

Asp Glu Ser Val Arg Ala His Leu Ala Ala Leu Asp Glu Thr Pro Val
225                 230                 235                 240

Ala Gly Pro Pro His Leu Arg Pro Pro Pro Ser His Val Pro Ala
                245                 250                 255

Gly Gly Pro Gly Leu Glu Asp Val Val Gln Glu Val Gln Gln Val Leu
            260                 265                 270

Ser Glu Phe Ile Arg Ala Asn Pro Lys Ala Trp Ala Pro Val Ile Ser
        275                 280                 285

Ala Trp Ser Ile Asp Leu Met Gly Gln Leu Ser Ser Thr Tyr Ser Gly
    290                 295                 300

Gln His Gln Arg Val Pro His Ala Thr Gly Ala Leu Asn Glu Leu Leu
305                 310                 315                 320

Gln Leu Trp Met Gly Cys Arg Ala Thr Arg Thr Leu Met Asp Ile Tyr
                325                 330                 335

Val Gln Cys Leu Ser Ala Leu Ile Gly Ser Cys Pro Asp Ala Cys Val
            340                 345                 350

Asp Ala Leu Leu Asp Thr Ser Val Gln His Ser Pro His Phe Asp Trp
        355                 360                 365

Val Val Ala His Ile Gly Ser Ser Phe Pro Gly Thr Ile Ile Ser Arg
    370                 375                 380

Val Leu Ser Cys Gly Leu Lys Asp Phe Cys Val His Gly Gly Ala Gly
385                 390                 395                 400

Gly Gly Ala Gly Ser Ser Gly Gly Ser Ser Ser Gln Thr Pro Ser Thr
                405                 410                 415

Asp Pro Phe Pro Gly Ser Pro Ala Ile Pro Ala Glu Lys Arg Val Pro
            420                 425                 430

Lys Ile Ala Ser Val Val Gly Ile Leu Gly His Leu Ala Ser Arg His
        435                 440                 445

Gly Asp Ser Ile Arg Arg Glu Leu Leu Arg Met Phe His Asp Ser Leu
    450                 455                 460

Ala Gly Gly Ser Gly Gly Arg Ser Gly Asp Pro Ser Leu Gln Ala Thr
465                 470                 475                 480

Val Pro Phe Leu Leu Gln Leu Ala Val Met Ser Pro Ala Leu Leu Gly
                485                 490                 495

Thr Val Ser Gly Glu Leu Val Asp Cys Leu Lys Pro Pro Ala Val Leu
            500                 505                 510

Ser Gln Leu Gln Gln His Leu Gln Gly Phe Pro Arg Glu Glu Leu Asp
        515                 520                 525

Asn Met Leu Asn Leu Ala Val His Leu Val Ser Gln Ala Ser Gly Ala
    530                 535                 540

Gly Ala Tyr Arg Leu Leu Gln Phe Leu Val Asp Thr Ala Met Pro Ala
545                 550                 555                 560

Ser Val Ile Thr Thr Gln Gly Leu Ala Val Pro Asp Thr Val Arg Glu
                565                 570                 575

Ala Cys Asp Arg Leu Ile Gln Leu Leu Leu Leu His Leu Gln Lys Leu
```

-continued

```
              580                 585                 590
Val His His Arg Gly Gly Ser Pro Gly Glu Gly Val Leu Gly Pro Pro
            595                 600                 605

Pro Pro Pro Arg Leu Val Pro Phe Leu Asp Ala Leu Lys Asn His Val
610                 615                 620

Gly Glu Leu Cys Gly Glu Thr Leu Arg Leu Glu Arg Lys Arg Phe Leu
625                 630                 635                 640

Trp Gln His Gln Leu Leu Gly Leu Leu Ser Val Tyr Thr Arg Pro Ser
                    645                 650                 655

Cys Gly Pro Glu Ala Leu Gly His Leu Leu Ser Arg Ala Arg Ser Pro
            660                 665                 670

Glu Glu Leu Ser Leu Ala Thr Gln Leu Tyr Ala Gly Leu Val Val Ser
            675                 680                 685

Leu Ser Gly Leu Leu Pro Leu Ala Phe Arg Ser Cys Leu Ala Arg Val
690                 695                 700

His Ala Gly Thr Leu Gln Pro Pro Phe Thr Arg Phe Leu Arg Asn
705                 710                 715                 720

Leu Ala Leu Leu Val Gly Trp Glu Gln Gln Gly Gly Glu Gly Pro Ala
                    725                 730                 735

Ala Leu Gly Ala His Phe Gly Glu Ser Ala Ser Ala His Leu Ser Asp
            740                 745                 750

Leu Ala Pro Leu Leu His Pro Glu Glu Val Ala Glu Ala Ala
            755                 760                 765

Ala Ser Leu Leu Ala Ile Cys Pro Phe Pro Ser Glu Ala Leu Ser Pro
770                 775                 780

Ser Gln Leu Leu Gly Leu Val Arg Ala Gly Val His Arg Phe Phe Ala
785                 790                 795                 800

Ser Leu Arg Leu His Gly Pro Pro Gly Val Ala Ser Ala Cys Gln Leu
                    805                 810                 815

Leu Thr Arg Leu Ser Gln Thr Ser Pro Ala Gly Leu Lys Ala Val Leu
            820                 825                 830

Gln Leu Leu Val Glu Gly Ala Leu His Arg Gly Asn Thr Glu Leu Phe
            835                 840                 845

Gly Gly Gln Val Asp Gly Asp Asn Glu Thr Leu Ser Val Val Ser Ala
850                 855                 860

Ser Leu Ala Ser Ala Ser Leu Leu Asp Thr Asn Arg Arg His Thr Ala
865                 870                 875                 880

Ala Val Pro Gly Pro Gly Gly Ile Trp Ser Val Phe His Ala Gly Val
                    885                 890                 895

Ile Gly Arg Gly Leu Lys Pro Pro Lys Phe Val Gln Ser Arg Asn Gln
            900                 905                 910

Gln Glu Val Ile Tyr Asn Thr Gln Ser Leu Leu Ser Leu Val His
            915                 920                 925

Cys Cys Ser Ala Pro Gly Gly Thr Glu Cys Gly Glu Cys Trp Gly Ala
930                 935                 940

Pro Ile Leu Ser Pro Glu Ala Lys Ala Val Ala Val Thr Leu Val
945                 950                 955                 960

Glu Ser Val Cys Pro Asp Ala Ala Gly Ala Glu Leu Ala Trp Pro Pro
                    965                 970                 975

Glu Glu His Ala Arg Ala Thr Val Glu Arg Asp Leu Arg Ile Gly Arg
            980                 985                 990

Arg Phe Arg Glu Gln Pro Leu Leu  Phe Glu Leu Leu Lys  Leu Val Ala
            995                 1000                1005
```

```
Ala Ala Pro Pro Ala Leu Cys Tyr Cys Ser Val Leu Leu Arg Gly
    1010                1015                1020

Leu Leu Ala Ala Leu Leu Gly His Trp Glu Ala Ser Arg His Thr
    1025                1030                1035

Asp Thr Thr His Ser Pro Trp His Leu Glu Ala Ser Cys Thr Leu
    1040                1045                1050

Val Ala Val Met Ala Glu Gly Ser Leu Leu Pro Pro Ala Leu Gly
    1055                1060                1065

Asn Met His Glu Val Phe Ser Gln Leu Ala Pro Phe Glu Val Arg
    1070                1075                1080

Leu Leu Leu Leu Ser Val Trp Gly Phe Leu Arg Glu His Gly Pro
    1085                1090                1095

Leu Pro Gln Lys Phe Ile Phe Gln Ser Glu Arg Gly Arg Phe Ile
    1100                1105                1110

Arg Asp Phe Ser Arg Glu Gly Gly Glu Gly Gly Pro His Leu
    1115                1120                1125

Ala Val Leu His Ser Val Leu His Arg Asn Leu Asp Arg Leu Gly
    1130                1135                1140

Leu Phe Ser Gly Arg Phe Gln Ala Pro Ser Pro Ser Thr Leu Leu
    1145                1150                1155

Arg Gln Gly Thr
    1160

<210> SEQ ID NO 15
<211> LENGTH: 170
<212> TYPE: PRT
<213> ORGANISM: Homo sapiens

<400> SEQUENCE: 15

Met Ala Leu Val Pro Gly Arg Ser Lys Glu Asp Gly Leu Trp Thr Arg
1               5                   10                  15

Asn Ser Pro Gly Ser Ser Gln His Pro Glu Ser Pro Arg Leu Pro Asn
            20                  25                  30

Pro Leu Trp Asp Arg Gly Lys Ile Gly Lys Val Glu Gly His Gln His
        35                  40                  45

Ile Gln Asp Phe Ser Gln Lys Ser His Leu Pro Ser Ile Val Val Glu
    50                  55                  60

Ser Ser Glu Val Asn Glu Glu Ser Gly Asp Leu His Leu Pro His Glu
65                  70                  75                  80

Glu Leu Leu Leu Leu Thr Asp Gly Glu Glu Glu Asp Ala Glu Ala Phe
                85                  90                  95

Phe Gln Asp Gln Ser Glu Glu Pro Gly Ala Ala Arg Pro His His Gln
            100                 105                 110

Ala Arg Gln Val Glu His Ser Thr Gln Arg Gly His Leu Glu Ile Arg
        115                 120                 125

Glu Leu Lys Lys Lys Leu Phe Lys Arg Arg Val Leu Asn Arg Glu
    130                 135                 140

Arg Arg Leu Arg His Arg Val Val Gly Ala Val Ile Asp Gln Gly Leu
145                 150                 155                 160

Ile Thr Arg His His Leu Lys Lys Arg Ala
                165                 170

<210> SEQ ID NO 16
<211> LENGTH: 1019
<212> TYPE: PRT
```

-continued

<213> ORGANISM: Homo sapiens

<400> SEQUENCE: 16

Met Ser Ala Leu Cys Asp Pro Pro Gly Ala Pro Gly Pro Pro Gly Pro
1               5                   10                  15

Ala Pro Ala Thr His Gly Pro Ala Pro Leu Ser Ala Gln Glu Leu Ser
            20                  25                  30

Gln Glu Ile Lys Ala Phe Leu Thr Gly Val Asp Pro Ile Leu Gly His
        35                  40                  45

Gln Leu Ser Ala Arg Glu His Ala Arg Cys Gly Leu Leu Leu Leu Arg
    50                  55                  60

Ser Leu Pro Pro Ala Arg Ala Ala Val Leu Asp His Leu Arg Gly Val
65                  70                  75                  80

Phe Asp Glu Ser Val Arg Ala His Leu Ala Leu Asp Glu Thr Pro
                85                  90                  95

Val Ala Gly Pro Pro His Leu Arg Pro Pro Pro Ser His Val Pro
            100                 105                 110

Ala Gly Gly Pro Gly Leu Glu Asp Val Val Gln Glu Val Gln Gln Val
            115                 120                 125

Leu Ser Glu Phe Ile Arg Ala Asn Pro Lys Ala Trp Ala Pro Val Ile
    130                 135                 140

Ser Ala Trp Ser Ile Asp Leu Met Gly Gln Leu Ser Ser Thr Tyr Ser
145                 150                 155                 160

Gly Gln His Gln Arg Val Pro His Ala Thr Gly Ala Leu Asn Glu Leu
                165                 170                 175

Leu Gln Leu Trp Met Gly Cys Arg Ala Thr Arg Thr Leu Met Asp Ile
            180                 185                 190

Tyr Val Gln Cys Leu Ser Ala Leu Ile Gly Ser Cys Pro Asp Ala Cys
        195                 200                 205

Val Asp Ala Leu Leu Asp Thr Ser Val Gln His Ser Pro His Phe Asp
    210                 215                 220

Trp Val Val Ala His Ile Gly Ser Ser Phe Pro Gly Thr Ile Ile Ser
225                 230                 235                 240

Arg Val Leu Ser Cys Gly Leu Lys Asp Phe Cys Val His Gly Gly Ala
                245                 250                 255

Gly Gly Gly Ala Gly Ser Ser Gly Ser Ser Ser Gln Thr Pro Ser
            260                 265                 270

Thr Asp Pro Phe Pro Gly Ser Pro Ala Ile Pro Ala Glu Lys Arg Val
        275                 280                 285

Pro Lys Ile Ala Ser Val Val Gly Ile Leu Gly His Leu Ala Ser Arg
    290                 295                 300

His Gly Asp Ser Ile Arg Arg Glu Leu Leu Arg Met Phe His Asp Ser
305                 310                 315                 320

Leu Ala Gly Gly Ser Gly Arg Ser Gly Asp Pro Ser Leu Gln Ala
                325                 330                 335

Thr Val Pro Phe Leu Leu Gln Leu Ala Val Met Ser Pro Ala Leu Leu
            340                 345                 350

Gly Thr Val Ser Gly Glu Leu Val Asp Cys Leu Lys Pro Pro Ala Val
        355                 360                 365

Leu Ser Gln Leu Gln Gln His Leu Gln Gly Phe Pro Arg Glu Glu Leu
    370                 375                 380

Asp Asn Met Leu Asn Leu Ala Val His Leu Val Ser Gln Ala Ser Gly
385                 390                 395                 400

-continued

```
Ala Gly Ala Tyr Arg Leu Leu Gln Phe Leu Val Asp Thr Ala Met Pro
                405                 410                 415

Ala Ser Val Ile Thr Thr Gln Gly Leu Ala Val Pro Asp Thr Val Arg
            420                 425                 430

Glu Ala Cys Asp Arg Leu Ile Gln Leu Leu Leu His Leu Gln Lys
            435                 440                 445

Leu Val His His Arg Gly Gly Ser Pro Gly Glu Gly Val Leu Gly Pro
        450                 455                 460

Pro Pro Pro Arg Leu Val Pro Phe Leu Asp Ala Leu Lys Asn His
465                 470                 475                 480

Val Gly Glu Leu Cys Gly Glu Thr Leu Arg Leu Glu Arg Lys Arg Phe
                485                 490                 495

Leu Trp Gln His Gln Leu Leu Gly Leu Leu Ser Val Tyr Thr Arg Pro
                500                 505                 510

Ser Cys Gly Pro Glu Ala Leu Gly His Leu Leu Ser Arg Ala Arg Ser
            515                 520                 525

Pro Glu Glu Leu Ser Leu Ala Thr Gln Leu Tyr Ala Gly Leu Val Val
        530                 535                 540

Ser Leu Ser Gly Leu Leu Pro Leu Ala Phe Arg Ser Cys Leu Ala Arg
545                 550                 555                 560

Val His Ala Gly Thr Leu Gln Pro Pro Phe Thr Ala Arg Phe Leu Arg
                565                 570                 575

Asn Leu Ala Leu Leu Val Gly Trp Glu Gln Gln Gly Gly Glu Gly Pro
            580                 585                 590

Ala Ala Leu Gly Ala His Phe Gly Glu Ser Ala Ser Ala His Leu Ser
        595                 600                 605

Asp Leu Ala Pro Leu Leu His Pro Glu Glu Val Ala Glu Ala
    610                 615                 620

Ala Ala Ser Leu Leu Ala Ile Cys Pro Phe Pro Ser Glu Ala Leu Ser
625                 630                 635                 640

Pro Ser Gln Leu Leu Gly Leu Val Arg Ala Gly Val His Arg Phe Phe
                645                 650                 655

Ala Ser Leu Arg Leu His Gly Pro Pro Gly Val Ala Ser Ala Cys Gln
            660                 665                 670

Leu Leu Thr Arg Leu Ser Gln Thr Ser Pro Ala Gly Leu Lys Ala Val
        675                 680                 685

Leu Gln Leu Leu Val Glu Gly Ala Leu His Arg Gly Asn Thr Glu Leu
    690                 695                 700

Phe Gly Gly Gln Val Asp Gly Asp Asn Glu Thr Leu Ser Val Val Ser
705                 710                 715                 720

Ala Ser Leu Ala Ser Ala Ser Leu Leu Asp Thr Asn Arg Arg His Thr
                725                 730                 735

Ala Ala Val Pro Gly Pro Gly Gly Ile Trp Ser Val Phe His Ala Gly
            740                 745                 750

Val Ile Gly Arg Gly Leu Lys Pro Pro Lys Phe Val Gln Ser Arg Asn
        755                 760                 765

Gln Gln Glu Val Ile Tyr Asn Thr Gln Ser Leu Leu Ser Leu Leu Val
    770                 775                 780

His Cys Cys Ser Ala Pro Gly Gly Thr Glu Cys Gly Glu Cys Trp Gly
785                 790                 795                 800

Ala Pro Ile Leu Ser Pro Glu Ala Ala Lys Ala Val Ala Val Thr Leu
                805                 810                 815

Val Glu Ser Val Cys Pro Asp Ala Ala Gly Ala Glu Leu Ala Trp Pro
```

-continued

```
                       820                 825                 830

Pro Glu Glu His Ala Arg Ala Thr Val Glu Arg Asp Leu Arg Ile Gly
            835                 840                 845

Arg Arg Phe Arg Glu Gln Pro Leu Leu Phe Glu Leu Leu Lys Leu Val
        850                 855                 860

Ala Ala Ala Pro Pro Ala Leu Cys Tyr Cys Ser Val Leu Leu Arg Gly
865                 870                 875                 880

Leu Leu Ala Ala Leu Leu Gly His Trp Glu Ala Ser Arg His Pro Asp
                885                 890                 895

Thr Thr His Ser Pro Trp His Leu Glu Ala Ser Cys Thr Leu Val Ala
            900                 905                 910

Val Met Ala Glu Gly Ser Leu Leu Pro Pro Ala Leu Gly Asn Met His
        915                 920                 925

Glu Val Phe Ser Gln Leu Ala Pro Phe Glu Val Arg Leu Leu Leu Leu
    930                 935                 940

Ser Val Trp Gly Phe Leu Arg Glu His Gly Pro Leu Pro Gln Lys Phe
945                 950                 955                 960

Ile Phe Gln Ser Glu Arg Gly Arg Phe Ile Arg Asp Phe Ser Arg Glu
                965                 970                 975

Gly Gly Gly Glu Gly Pro His Leu Ala Val Leu His Ser Val Leu
            980                 985                 990

His Arg Asn Ile Asp Arg Leu Gly  Leu Phe Ser Gly Arg  Phe Gln Ala
        995                 1000                1005

Pro Ser  Pro Ser Thr Leu Leu  Arg Gln Gly Thr
    1010                1015

<210> SEQ ID NO 17
<211> LENGTH: 908
<212> TYPE: PRT
<213> ORGANISM: Homo sapiens

<400> SEQUENCE: 17

Pro Ala Gly Gly Pro Gly Leu Glu Asp Val Val Gln Glu Val Gln Gln
1               5                   10                  15

Val Leu Ser Glu Phe Ile Arg Ala Asn Pro Lys Ala Trp Ala Pro Val
            20                  25                  30

Ile Ser Ala Trp Ser Ile Asp Leu Met Gly Gln Leu Ser Ser Thr Tyr
        35                  40                  45

Ser Gly Gln His Gln Arg Val Pro His Ala Thr Gly Ala Leu Asn Glu
    50                  55                  60

Leu Leu Gln Leu Trp Met Gly Cys Arg Ala Thr Arg Thr Leu Met Asp
65                  70                  75                  80

Ile Tyr Val Gln Cys Leu Ser Ala Leu Ile Gly Ser Cys Pro Asp Ala
                85                  90                  95

Cys Val Asp Ala Leu Leu Asp Thr Ser Val Gln His Ser Pro His Phe
            100                 105                 110

Asp Trp Val Val Ala His Ile Gly Ser Ser Phe Pro Gly Thr Ile Ile
        115                 120                 125

Ser Arg Val Leu Ser Cys Gly Leu Lys Asp Phe Cys Val His Gly Gly
    130                 135                 140

Ala Gly Gly Gly Ala Gly Ser Ser Gly Gly Ser Ser Ser Gln Thr Pro
145                 150                 155                 160

Ser Thr Asp Pro Phe Pro Gly Ser Pro Ala Ile Pro Ala Glu Lys Arg
                165                 170                 175
```

-continued

```
Val Pro Lys Ile Ala Ser Val Val Gly Ile Gly His Leu Ala Ser
            180                 185                 190

Arg His Gly Asp Ser Ile Arg Arg Glu Leu Leu Arg Met Phe His Asp
            195                 200                 205

Ser Leu Ala Gly Gly Ser Gly Gly Arg Ser Gly Asp Pro Ser Leu Gln
            210                 215                 220

Ala Thr Val Pro Phe Leu Leu Gln Leu Ala Val Met Ser Pro Ala Leu
225                 230                 235                 240

Leu Gly Thr Val Ser Gly Glu Leu Val Asp Cys Leu Lys Pro Pro Ala
                245                 250                 255

Val Leu Ser Gln Leu Gln Gln His Leu Gln Gly Phe Pro Arg Glu Glu
            260                 265                 270

Leu Asp Asn Met Leu Asn Leu Ala Val His Leu Val Ser Gln Ala Ser
            275                 280                 285

Gly Ala Gly Ala Tyr Arg Leu Leu Gln Phe Leu Val Asp Thr Ala Met
            290                 295                 300

Pro Ala Ser Val Ile Thr Thr Gln Gly Leu Ala Val Pro Asp Thr Val
305                 310                 315                 320

Arg Glu Ala Cys Asp Arg Leu Ile Gln Leu Leu Leu His Leu Gln
                325                 330                 335

Lys Leu Val His His Arg Gly Gly Ser Pro Gly Glu Gly Val Leu Gly
            340                 345                 350

Pro Pro Pro Pro Arg Leu Val Pro Phe Leu Asp Ala Leu Lys Asn
            355                 360                 365

His Val Gly Glu Leu Cys Gly Glu Thr Leu Arg Leu Glu Arg Lys Arg
            370                 375                 380

Phe Leu Trp Gln His Gln Leu Leu Gly Leu Leu Ser Val Tyr Thr Arg
385                 390                 395                 400

Pro Ser Cys Gly Pro Glu Ala Leu Gly His Leu Leu Ser Arg Ala Arg
                405                 410                 415

Ser Pro Glu Glu Leu Ser Leu Ala Thr Gln Leu Tyr Ala Gly Leu Val
            420                 425                 430

Val Ser Leu Ser Gly Leu Leu Pro Leu Ala Phe Arg Ser Cys Leu Ala
            435                 440                 445

Arg Val His Ala Gly Thr Leu Gln Pro Pro Phe Thr Ala Arg Phe Leu
            450                 455                 460

Arg Asn Leu Ala Leu Leu Val Gly Trp Glu Gln Gln Gly Gly Glu Gly
465                 470                 475                 480

Pro Ala Ala Leu Gly Ala His Phe Gly Glu Ser Ala Ser Ala His Leu
                485                 490                 495

Ser Asp Leu Ala Pro Leu Leu Leu His Pro Glu Glu Val Ala Glu
            500                 505                 510

Ala Ala Ala Ser Leu Leu Ala Ile Cys Pro Phe Pro Ser Glu Ala Leu
            515                 520                 525

Ser Pro Ser Gln Leu Leu Gly Leu Val Arg Ala Gly Val His Arg Phe
            530                 535                 540

Phe Ala Ser Leu Arg Leu His Gly Pro Pro Gly Val Ala Ser Ala Cys
545                 550                 555                 560

Gln Leu Leu Thr Arg Leu Ser Gln Thr Ser Pro Ala Gly Leu Lys Ala
                565                 570                 575

Val Leu Gln Leu Leu Val Glu Gly Ala Leu His Arg Gly Asn Thr Glu
            580                 585                 590

Leu Phe Gly Gly Gln Val Asp Gly Asp Asn Glu Thr Leu Ser Val Val
```

```
                595                 600                 605
Ser Ala Ser Leu Ala Ser Ala Ser Leu Leu Asp Thr Asn Arg Arg His
        610                 615                 620

Thr Ala Ala Val Pro Gly Pro Gly Gly Ile Trp Ser Val Phe His Ala
625                 630                 635                 640

Gly Val Ile Gly Arg Gly Leu Lys Pro Pro Lys Phe Val Gln Ser Arg
                645                 650                 655

Asn Gln Gln Glu Val Ile Tyr Asn Thr Gln Ser Leu Leu Ser Leu Leu
        660                 665                 670

Val His Cys Cys Ser Ala Pro Gly Gly Thr Glu Cys Gly Glu Cys Trp
            675                 680                 685

Gly Ala Pro Ile Leu Ser Pro Glu Ala Ala Lys Ala Val Ala Val Thr
690                 695                 700

Leu Val Glu Ser Val Cys Pro Asp Ala Ala Gly Ala Glu Leu Ala Trp
705                 710                 715                 720

Pro Pro Glu Glu His Ala Arg Ala Thr Val Glu Arg Asp Leu Arg Ile
                725                 730                 735

Gly Arg Arg Phe Arg Glu Gln Pro Leu Leu Phe Glu Leu Leu Lys Leu
            740                 745                 750

Val Ala Ala Pro Pro Ala Leu Cys Tyr Cys Ser Val Leu Leu Arg
755                 760                 765

Gly Leu Leu Ala Ala Leu Leu Gly His Trp Glu Ala Ser Arg His Pro
770                 775                 780

Asp Thr Thr His Ser Pro Trp His Leu Glu Ala Ser Cys Thr Leu Val
785                 790                 795                 800

Ala Val Met Ala Glu Gly Ser Leu Leu Pro Pro Ala Leu Gly Asn Met
                805                 810                 815

His Glu Val Phe Ser Gln Leu Ala Pro Phe Glu Val Arg Leu Leu Leu
            820                 825                 830

Leu Ser Val Trp Gly Phe Leu Arg Glu His Gly Pro Leu Pro Gln Lys
            835                 840                 845

Phe Ile Phe Gln Ser Glu Arg Gly Arg Phe Ile Arg Asp Phe Ser Arg
850                 855                 860

Glu Gly Gly Gly Glu Gly Gly Pro His Leu Ala Val Leu His Ser Val
865                 870                 875                 880

Leu His Arg Asn Ile Asp Arg Leu Gly Leu Phe Ser Gly Arg Phe Gln
                885                 890                 895

Ala Pro Ser Pro Ser Thr Leu Leu Arg Gln Gly Thr
            900                 905

<210> SEQ ID NO 18
<211> LENGTH: 833
<212> TYPE: PRT
<213> ORGANISM: Homo sapiens

<400> SEQUENCE: 18

Pro Arg Val Arg Asp Ile Tyr Val Gln Cys Leu Ser Ala Leu Ile Gly
1               5                   10                  15

Ser Cys Pro Asp Ala Cys Val Asp Ala Leu Leu Asp Thr Ser Val Gln
            20                  25                  30

His Ser Pro His Phe Asp Trp Val Ala His Ile Gly Ser Ser Phe
        35                  40                  45

Pro Gly Thr Ile Ile Ser Arg Val Leu Ser Cys Gly Leu Lys Asp Phe
    50                  55                  60
```

-continued

```
Cys Val His Gly Gly Ala Gly Gly Ala Gly Ser Ser Gly Gly Ser
 65                  70                  75                  80

Ser Ser Gln Thr Pro Ser Thr Asp Pro Phe Pro Gly Ser Pro Ala Ile
                 85                  90                  95

Pro Ala Glu Lys Arg Val Pro Lys Ile Ala Ser Val Val Gly Ile Leu
            100                 105                 110

Gly His Leu Ala Ser Arg His Gly Asp Ser Ile Arg Arg Glu Leu Leu
            115                 120                 125

Arg Met Phe His Asp Ser Leu Ala Gly Gly Ser Gly Gly Arg Ser Gly
130                 135                 140

Asp Pro Ser Leu Gln Ala Thr Val Pro Phe Leu Gln Leu Ala Val
145                 150                 155                 160

Met Ser Pro Ala Leu Leu Gly Thr Val Ser Gly Glu Leu Val Asp Cys
                165                 170                 175

Leu Lys Pro Pro Ala Val Leu Ser Gln Leu Gln Gln His Leu Gln Gly
                180                 185                 190

Phe Pro Arg Glu Glu Leu Asp Asn Met Leu Asn Leu Ala Val His Leu
            195                 200                 205

Val Ser Gln Ala Ser Gly Ala Gly Ala Tyr Arg Leu Leu Gln Phe Leu
    210                 215                 220

Val Asp Thr Ala Met Pro Ala Ser Val Ile Thr Thr Gln Gly Leu Ala
225                 230                 235                 240

Val Pro Asp Thr Val Arg Glu Ala Cys Asp Arg Leu Ile Gln Leu Leu
                245                 250                 255

Leu Leu His Leu Gln Lys Leu Val His His Arg Gly Gly Ser Pro Gly
                260                 265                 270

Glu Gly Val Leu Gly Pro Pro Pro Pro Arg Leu Val Pro Phe Leu
            275                 280                 285

Asp Ala Leu Lys Asn His Val Gly Glu Leu Cys Gly Glu Thr Leu Arg
    290                 295                 300

Leu Glu Arg Lys Arg Phe Leu Trp Gln His Gln Leu Leu Gly Leu Leu
305                 310                 315                 320

Ser Val Tyr Thr Arg Pro Ser Cys Gly Pro Glu Ala Leu Gly His Leu
                325                 330                 335

Leu Ser Arg Ala Arg Ser Pro Glu Glu Leu Ser Leu Ala Thr Gln Leu
                340                 345                 350

Tyr Ala Gly Leu Val Val Ser Leu Ser Gly Leu Leu Pro Leu Ala Phe
            355                 360                 365

Arg Ser Cys Leu Ala Arg Val His Ala Gly Thr Leu Gln Pro Pro Phe
            370                 375                 380

Thr Ala Arg Phe Leu Arg Asn Leu Ala Leu Leu Val Gly Trp Glu Gln
385                 390                 395                 400

Gln Gly Gly Glu Gly Pro Ala Ala Leu Gly Ala His Phe Gly Glu Ser
                405                 410                 415

Ala Ser Ala His Leu Ser Asp Leu Ala Pro Leu Leu Leu His Pro Glu
            420                 425                 430

Glu Glu Val Ala Glu Ala Ala Ala Ser Leu Leu Ala Ile Cys Pro Phe
            435                 440                 445

Pro Ser Glu Ala Leu Ser Pro Ser Gln Leu Leu Gly Leu Val Arg Ala
            450                 455                 460

Gly Val His Arg Phe Phe Ala Ser Leu Arg Leu His Gly Pro Pro Gly
465                 470                 475                 480

Val Ala Ser Ala Cys Gln Leu Leu Thr Arg Leu Ser Gln Thr Ser Pro
```

```
                    485                 490                 495
Ala Gly Leu Lys Ala Val Leu Gln Leu Val Glu Gly Ala Leu His
                500                 505                 510

Arg Gly Asn Thr Glu Leu Phe Gly Gly Gln Val Asp Gly Asn Glu
                515                 520                 525

Thr Leu Ser Val Val Ser Ala Ser Leu Ala Ser Ala Ser Leu Leu Asp
                530                 535                 540

Thr Asn Arg Arg His Thr Ala Ala Val Pro Gly Pro Gly Gly Ile Trp
545                 550                 555                 560

Ser Val Phe His Ala Gly Val Ile Gly Arg Gly Leu Lys Pro Pro Lys
                565                 570                 575

Phe Val Gln Ser Arg Asn Gln Gln Glu Val Ile Tyr Asn Thr Gln Ser
                580                 585                 590

Leu Leu Ser Leu Leu Val His Cys Cys Ser Ala Pro Gly Gly Thr Glu
                595                 600                 605

Cys Gly Glu Cys Trp Gly Ala Pro Ile Leu Ser Pro Glu Ala Ala Lys
                610                 615                 620

Ala Val Ala Val Thr Leu Val Glu Ser Val Cys Pro Asp Ala Ala Gly
625                 630                 635                 640

Ala Glu Leu Ala Trp Pro Pro Glu Glu His Ala Arg Ala Thr Val Glu
                645                 650                 655

Arg Asp Leu Arg Ile Gly Arg Arg Phe Arg Glu Gln Pro Leu Leu Phe
                660                 665                 670

Glu Leu Leu Lys Leu Val Ala Ala Pro Pro Ala Leu Cys Tyr Cys
                675                 680                 685

Ser Val Leu Leu Arg Gly Leu Leu Ala Ala Leu Leu Gly His Trp Glu
                690                 695                 700

Ala Ser Arg His Pro Asp Thr Thr His Ser Pro Trp His Leu Glu Ala
705                 710                 715                 720

Ser Cys Thr Leu Val Ala Val Met Ala Glu Gly Ser Leu Leu Pro Pro
                725                 730                 735

Ala Leu Gly Asn Met His Glu Val Phe Ser Gln Leu Ala Pro Phe Glu
                740                 745                 750

Val Arg Leu Leu Leu Leu Ser Val Trp Gly Phe Leu Arg Glu His Gly
                755                 760                 765

Pro Leu Pro Gln Lys Phe Ile Phe Gln Ser Glu Arg Gly Arg Phe Ile
                770                 775                 780

Arg Asp Phe Ser Arg Glu Gly Gly Glu Gly Gly Pro His Leu Ala
785                 790                 795                 800

Val Leu His Ser Val Leu His Arg Asn Ile Asp Arg Leu Gly Leu Phe
                805                 810                 815

Ser Gly Arg Phe Gln Ala Pro Ser Pro Ser Thr Leu Leu Arg Gln Gly
                820                 825                 830

Thr

<210> SEQ ID NO 19
<211> LENGTH: 963
<212> TYPE: PRT
<213> ORGANISM: Mus musculus

<400> SEQUENCE: 19

Met Ile Leu Met Ile Thr Leu Phe Thr Thr Ala Thr Phe Leu Val Leu
1               5                   10                  15

Gly Val Ser Val Trp Val Leu Ile Lys Glu Ile Leu Thr Val His Val
```

-continued

```
                20                  25                  30
Pro Pro Pro Ile Pro Gln Arg Val Lys Phe His Met Leu His Tyr Phe
            35                  40                  45
Phe Gln Leu Thr Ile Ala Leu Gly Asn Val Leu Glu Lys Met Lys Ile
        50                  55                  60
Cys Pro Met Pro Arg Phe Phe Cys Phe Ile Gln Asp Leu Leu Val Ser
65                  70                  75                  80
Lys Asn Asn Phe Gly Val Leu Val Lys Asn Met His Phe Gly Thr Ile
                85                  90                  95
Pro Val Arg Leu Phe Gln Pro Lys Ala Thr Ser Ser Gly Pro Arg Lys
            100                 105                 110
Gly Ile Ile Phe Tyr His Gly Gly Gly Val Phe Gly Ser Leu Asp
            115                 120                 125
Ser Tyr His Asn Thr Cys Ser Tyr Leu Ala His Glu Thr Asp Ser Val
        130                 135                 140
Val Met Ala Val Gly Tyr Arg Lys Leu Pro Asp His His His Pro Thr
145                 150                 155                 160
Ala Tyr His Asp Cys Leu Asn Ala Thr Val His Phe Leu Lys Glu Leu
                165                 170                 175
Lys Thr Tyr Gly Val Asp Pro Ala Arg Val Val Val Ser Gly Glu Ser
            180                 185                 190
Ile Gly Ala Gly Ala Ala Ala Ile Ile Ala Gln Val Leu Ala Arg
            195                 200                 205
Lys Asp Leu Pro Gln Phe Arg Ala Gln Val Leu Ile Asn Pro Val Val
        210                 215                 220
Gln Gly Val Asn Phe Gln Leu Pro Ser Tyr Gln Gln Tyr Ser Asp Val
225                 230                 235                 240
Pro Phe Leu Ser Arg Lys Phe Leu Met Thr Cys Ala Cys Lys Tyr Leu
                245                 250                 255
Ala Ile Asp Gln Ser Trp Lys Asp Ala Met Leu Lys Gly Thr Phe Ile
            260                 265                 270
Pro Pro Asp His Trp Lys Lys Tyr Ala Lys Trp Leu Ser Ser Asp Asn
            275                 280                 285
Ile Pro Gln Arg Phe Lys Ser Gln Gly Arg Gln Pro Glu Phe Pro Gly
        290                 295                 300
Pro Phe Asn Glu Ser Ala Tyr Leu Glu Thr Asn His Ile Phe Ser Leu
305                 310                 315                 320
Glu Thr Ser Pro Leu Leu Ala Asp Asp Lys Ile Ile Ala Gln Leu Pro
                325                 330                 335
Glu Thr Phe Leu Val Ser Ser Glu Tyr Asp Val Leu Arg Asp Asp Thr
            340                 345                 350
Leu Leu Tyr Lys Lys Arg Leu Glu Glu Gln Gly Val Pro Val Thr Trp
            355                 360                 365
Leu Trp Val Gly Leu Pro Asp Val Arg Val Val Pro Leu Ser Gln Gly
        370                 375                 380
Pro Arg Ala Pro Gly Pro Pro Gly Pro Ala Pro Ala Thr His Gly Pro
385                 390                 395                 400
Val Pro Leu Ser Ala Gln Glu Leu Ser Gln Glu Ile Lys Ala Phe Leu
                405                 410                 415
Thr Gly Val Asp Pro Ile Leu Gly His Gln Leu Ser Ala Arg Glu His
            420                 425                 430
Ala Gln Cys Gly Leu Leu Leu Leu Arg Ser Leu Pro Pro Ala Gln Ala
            435                 440                 445
```

```
Ala Val Leu Asp His Leu Arg Gly Val Phe Asp Glu Ser Val Gln Ala
    450                 455                 460
His Leu Ala Ala Leu Glu Glu Ser Pro Val Ala Gly Pro Pro His Leu
465                 470                 475                 480
Arg Pro Pro Ser Pro Ser His Val Pro Thr Gly Pro Gly Leu Glu
            485                 490                 495
Asp Val Val His Glu Val Gln Gln Val Leu Cys Glu Phe Ile Arg Ala
            500                 505                 510
Asn Pro Lys Val Trp Ala Pro Val Ile Ser Ala Trp Ser Ile Asp Leu
        515                 520                 525
Met Gly Gln Leu Ser Ser Thr Tyr Ser Gly Gln His Gln Arg Val Pro
    530                 535                 540
His Ala Thr Gly Ser Arg Asn Glu Leu Leu Gln Leu Trp Met Ser Cys
545                 550                 555                 560
Arg Asp Thr Arg Thr Leu Met Asp Ile Tyr Val Gln Cys Leu Ser Ala
                565                 570                 575
Leu Ile Gly Ser Cys Pro Asp Ala Tyr Ser Phe Pro Gly Phe Pro Ala
            580                 585                 590
Ile Pro Gly Glu Lys Arg Val Pro Lys Ile Ala Ser Ala Val Gly Ile
        595                 600                 605
Gln Val Thr Trp Leu Ser Ala Met Glu Thr Ala Ser Asp Gly Asn Cys
    610                 615                 620
Cys Ala Cys Phe Met Ile Val Trp Gln Arg Phe Leu Val Asp Thr Ala
625                 630                 635                 640
Met Pro Ala Ala Val Ile Thr Thr Gln Gly Leu Ala Val Pro Asp Thr
                645                 650                 655
Met Arg Glu Ala Tyr Asp Arg Leu Ile Gln Leu Leu Leu His Leu
                660                 665                 670
Gln Lys Leu Val His His Arg Gly Gly Ala Pro Gly Glu Gly Val Leu
        675                 680                 685
Gly Pro Pro Ser Pro Pro Leu Pro Val Pro Phe Leu Asp Ala Leu Arg
    690                 695                 700
Asn His Val Gly Glu Leu Cys Gly Lys Thr Leu Arg Leu Glu Arg Lys
705                 710                 715                 720
Arg Phe Leu Trp Gln His Gln Leu Leu Ala Tyr Ser Trp Phe Leu Arg
                725                 730                 735
Lys Leu Ala Leu Leu Val Gly Trp Glu Gln Gln Gly Asp Glu Gly Pro
            740                 745                 750
Ser Ala Leu Gly Ala Arg Phe Gly Glu Ser Ala Ser Ala His Leu Ser
        755                 760                 765
Asp Leu Ala Pro Leu Leu His Pro Glu Glu Val Ala Glu Ala
    770                 775                 780
Ala Ala Ser Leu Leu Ala Val Cys Pro Phe Pro Ser Glu Ala Leu Ser
785                 790                 795                 800
Pro Ser Gln Leu Leu Gly Leu Val Arg Ala Gly Val His His Phe Phe
                805                 810                 815
Asn Ser Leu Arg Leu His Gly Pro Pro Gly Val Ala Ser Ala Ser Gln
            820                 825                 830
Leu Leu Thr Arg Leu Ser Gln Thr Ser Pro Ala Gly Leu Lys Ala Val
        835                 840                 845
Leu Gln Leu Leu Val Glu Val Ala Leu His Arg Gly Asn Thr Glu Leu
    850                 855                 860
```

```
Phe Gly Glu Glu Met Val Gly Asp Asn Glu Thr Leu Ser Ile Val Ser
865                 870                 875                 880

Thr Pro Leu Ala Ser Ala Ser Leu Leu Asp Ile Asn Arg Arg His Thr
            885                 890                 895

Ala Ala Val Pro Gly Pro Gly Ile Trp Ser Val Phe His Ala Gly
        900                 905                 910

Val Ile Gly Arg Gly Leu Lys Ser Pro Lys Ile Val Gln Ser Arg Asn
        915                 920                 925

His Gln Glu Val Ile Tyr Asn Thr Gln Ser Leu Ile Ser Leu Leu Val
        930                 935                 940

His Cys Cys Ser Ala Ser Gly Ser Ser Glu His Lys Gly Tyr Trp Gly
945                 950                 955                 960

Ala Pro Thr

<210> SEQ ID NO 20
<211> LENGTH: 900
<212> TYPE: PRT
<213> ORGANISM: Anopheles gambiae

<400> SEQUENCE: 20

Lys Asn Leu Pro Asp Pro Ser Val Asp Asp Glu Ala Val Gln Glu Ile
1               5                   10                  15

His Glu Ala Leu Glu Arg Leu Val Thr Val Gly Pro Thr Ala Trp Cys
            20                  25                  30

Pro Val Ile Ser Ser Trp Cys Leu Lys Leu Leu Gly Glu Val Cys Lys
        35                  40                  45

Lys His Cys Arg Arg Arg Pro Pro Asp Ile Arg Gly Ala Cys Asn Leu
    50                  55                  60

Trp Leu Gly Cys Ser Ala Ile Arg Tyr Leu Leu Ser Leu Ser Ala Leu
65                  70                  75                  80

Cys Phe Glu Lys Leu Asp Gln Arg Glu Met Asp Glu Cys Ile Asn Glu
                85                  90                  95

Met Leu Val Ile Tyr Gly Thr His Thr Pro Phe Phe Asp Trp Val Val
            100                 105                 110

Ala Arg Leu Gly Gly Cys Phe Pro Leu Arg Val Met Ser Ser Met Leu
        115                 120                 125

Ser Met Gly Val Ala Arg Phe Thr Gly Asp Phe Asp Gln Pro Ser Glu
    130                 135                 140

Ser Glu Val Glu Val Leu Ser Tyr Leu Gly Leu Ala His Glu Ser Asp
145                 150                 155                 160

Leu Arg Lys Ala Leu Lys Ser Thr Leu Glu His Val Ala Ser Tyr Lys
                165                 170                 175

Gln Pro Ile Pro Tyr Leu Leu Met Leu Ala Lys Ala Ser Glu Thr Ile
            180                 185                 190

Ser Gln Ala Leu Val Ala Val Phe Leu Glu Leu His Asp Glu Asn Arg
        195                 200                 205

Leu Pro Thr Leu Thr Val Leu Pro Lys Asn Trp Pro Ala Asn Ile Gly
    210                 215                 220

Leu Pro Tyr Val Leu His Thr Val Ala Gly Leu Leu Leu Lys Met Lys
225                 230                 235                 240

Lys His Ala Ile Arg Val Thr Leu Ile Leu Ala Lys Met Ser Thr Gln
                245                 250                 255

His Ser Trp Cys Gln Glu Leu Leu Glu Met Met Phe Ile Glu Leu Glu
            260                 265                 270
```

-continued

```
Thr Leu Val Leu Asp Lys His Thr Ala Ala Leu Leu Glu Asp Ile Ile
            275                 280                 285
Arg Asp Gly Met Arg Glu Met Leu Trp Asn Ser Cys Thr Ser Asp Val
        290                 295                 300
Pro Tyr Leu Gln Gln Val Ala Val Arg Leu Ile Leu Leu Ala Ser Phe
305                 310                 315                 320
Lys Ser Asn Ser Val Phe His Gln Thr Ile Val Tyr Leu Leu Ser Val
                325                 330                 335
Ser Glu Pro Ala Leu Ala Val Ser Thr Lys Pro His Leu Asn Ala Leu
            340                 345                 350
Val Arg Val Leu Gly Gly Pro His Gly Thr Val Asp Val Pro Lys Val
        355                 360                 365
Lys Pro Ala Phe Glu Thr Ala Phe Glu Lys Ile Leu Ile Ser Pro Cys
370                 375                 380
Lys Arg Val Glu Cys Trp Asn Ile Leu His Asn Leu Val Glu Leu Leu
385                 390                 395                 400
Lys Leu Glu Arg Thr Ala Ile Leu Gly Ser Thr Leu Arg Lys Val Asn
                405                 410                 415
Cys Thr Gly Met Met His Glu Leu Leu Asp Arg Val Leu Lys Ile Trp
            420                 425                 430
Glu Asn Phe Met Ser Arg Glu Arg Gln Asp Asp Thr Gln Gly Gly Gly
        435                 440                 445
Cys Thr Val Arg Ala Thr Gln Glu Val Gln Glu Asn Ala Asn Glu Pro
450                 455                 460
Gly Lys Arg Val Lys Asn Glu Arg Pro Glu Pro Met Glu Thr Asp Glu
465                 470                 475                 480
Gln His Arg Leu Gly Thr Gly Ser Arg Thr Val Thr Tyr Lys Asp Leu
                485                 490                 495
Ile His Glu Thr Val Arg Leu Ile Glu Cys Met Asp Leu Gly Lys Ser
            500                 505                 510
Val Thr Ile Gly Thr Ala Gln Thr Leu Lys Leu Ser Gln Leu Leu Val
        515                 520                 525
Lys Tyr Phe Phe Tyr Cys Leu Lys Leu Ser Thr Ala Gly Thr Ser Val
530                 535                 540
Pro Ser Gly Thr Val Pro Glu Ser Leu Asp Glu Ser Leu Asn Arg Val
545                 550                 555                 560
Tyr Ser Leu Leu Ser Lys His Cys Gly His Arg Lys Ala Ala Arg Thr
                565                 570                 575
Ala Ala Leu Arg Glu Leu Leu Glu Gly Ala Leu Phe Leu Tyr Gly Asp
            580                 585                 590
Leu Phe Gly Ser Gln Ala Glu Ser Gln Ala Tyr Ser Phe Asp Lys Pro
        595                 600                 605
Asp Asp Leu Leu Ile Arg Leu Asn Gln Lys Gln Gly Ile Ala Leu Asn
610                 615                 620
Ala Ser Arg Ala Thr Val Leu His Ala Gly Ile Ile Gly Gln Gly Pro
625                 630                 635                 640
Lys Ile Pro Ser Lys Lys Ala Val Gly Pro Ala Ser Glu Met Gln Asn
                645                 650                 655
His Leu Leu Asn Ala Ile Val Ala Cys Cys Gln Asp Val Asn Asp His
            660                 665                 670
Gln Ala Thr Ile Asp Gly Phe Ser Tyr Val Ser Leu Leu Leu Val Glu
        675                 680                 685
Met Ile Ser Pro Asp Val Met Tyr Asn Gly Leu Pro Trp Pro Glu Glu
```

-continued

```
                690                 695                 700
Asp Phe Ile Arg Val Thr Met Glu Arg Asp Leu Gln Ile Gln Arg Thr
705                 710                 715                 720

Phe Arg His Ser Pro Ile Leu Trp Ser Ile Leu Gly Leu Val Ala Cys
                725                 730                 735

Tyr Arg Pro Ser Leu Cys Tyr Cys Ser Val Leu Leu Arg Ala Leu Cys
                740                 745                 750

Ala Ser Ala Leu His Gln Trp Arg Ser Lys Thr Ala Glu Thr Leu Asn
                755                 760                 765

Gly Gln Lys Thr Asp Leu Leu Tyr Met Thr Thr Lys Leu Leu Glu Leu
        770                 775                 780

Met Ala Leu Ala Gln Leu Leu Pro Pro Pro Leu Ser Tyr Leu His Ile
785                 790                 795                 800

Val Leu Glu Tyr Phe Asp Gly Pro Glu Ile Ala Tyr Val Leu Lys Glu
                805                 810                 815

Cys Val Trp Asn Tyr Met Lys Asp His Val Pro Ser Pro Val Leu Phe
                820                 825                 830

Val Cys Asp Pro Thr Gly Phe His Trp Arg Asp Pro Leu Thr Ser Arg
                835                 840                 845

Pro Pro Leu Gln Tyr Thr Asn Pro Leu Arg Asn Thr Met Gln Lys Lys
                850                 855                 860

Leu Thr Lys Val Gly His Leu Tyr His Gln Met Phe Val Gly Pro Glu
865                 870                 875                 880

Leu Arg Asn Pro Ser Ala Ser Asn Ser Gly Gln Pro Thr Gln Gln Pro
                885                 890                 895

Leu Val Gln Gly
            900

<210> SEQ ID NO 21
<211> LENGTH: 27
<212> TYPE: PRT
<213> ORGANISM: Homo sapiens

<400> SEQUENCE: 21

Met Ser Ala Leu Cys Asp Pro Pro Gly Ala Pro Gly Pro Pro Gly Pro
1               5                   10                  15

Ala Pro Ala Thr His Gly Pro Ala Pro Leu Ser
            20                  25
```